United States Patent [19]

Laine et al.

[11] Patent Number: 6,090,573
[45] Date of Patent: Jul. 18, 2000

[54] DETECTING EUBACTERIA AND FUNGUS AND DETERMINING THEIR ANTIBIOTIC SENSITIVITY BY USING CATALYTICALLY INACTIVE MUREIN BINDING ENZYMES

[76] Inventors: Roger A. Laine, 298 Cornell Ave.; Wai Chun Jennifer Lo, 1517 Chippenham Dr., both of Baton Rouge, La. 70808

[21] Appl. No.: 09/261,664

[22] Filed: Mar. 3, 1999

Related U.S. Application Data

[63] Continuation of application No. 08/823,293, Mar. 21, 1997, Pat. No. 5,935,804.

[51] Int. Cl.[7] ............... C12Q 1/18; C12Q 1/34; C12Q 1/02; C12Q 1/04; C12N 9/36
[52] U.S. Cl. ............... 435/32; 435/18; 435/29; 435/34; 435/206
[58] Field of Search ............... 435/18, 29, 206, 435/188, 32, 34

[56] References Cited

U.S. PATENT DOCUMENTS

| | | | |
|---|---|---|---|
| 4,065,354 | 12/1977 | Ullman et al. | 195/63 |
| 4,473,652 | 9/1984 | Okazaki et al. | 435/536 |
| 5,128,240 | 7/1992 | Shah | 435/7.1 |
| 5,187,066 | 2/1993 | Becker et al. | 435/7.36 |
| 5,314,816 | 5/1994 | Uerrmann et al. | 435/188 |
| 5,340,736 | 8/1994 | Goldberg | 435/226 |
| 5,514,554 | 5/1996 | Bacus | 435/7.23 |
| 5,514,774 | 5/1996 | Olivera et al. | 530/324 |

FOREIGN PATENT DOCUMENTS

92/17786  10/1992  WIPO.

*Primary Examiner*—Jon P. Weber
*Attorney, Agent, or Firm*—John S. Sundsmo; BioMed Patent. com

[57] ABSTRACT

A method is presented for detecting eubacteria and fungus in biological samples, and, if present, determining their antibiotic sensitivity, where the presence and amount of eubacteria or fungus is measured by means of catalytically inactive murein binding enzymes in both parts of the method. The sensitivity of eubacteria or fungus to a test antibiotic is obtained by comparing the amount of eubacteria or fungus in the sample after culturing the sample in the presence and absence of the test antibiotic. The biological sample may be chemically treated with alkali to cleave peptide bonds in the sample before incubating the sample with the catalytically inactive murein binding enzyme.

34 Claims, 11 Drawing Sheets

FSC-H\FSC-HEIGHT →

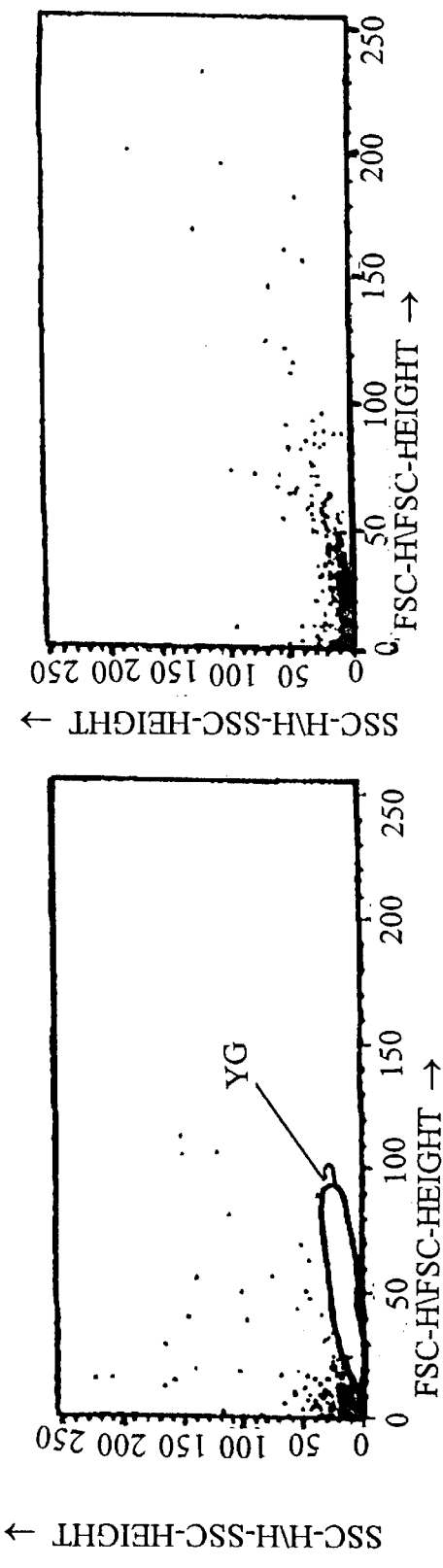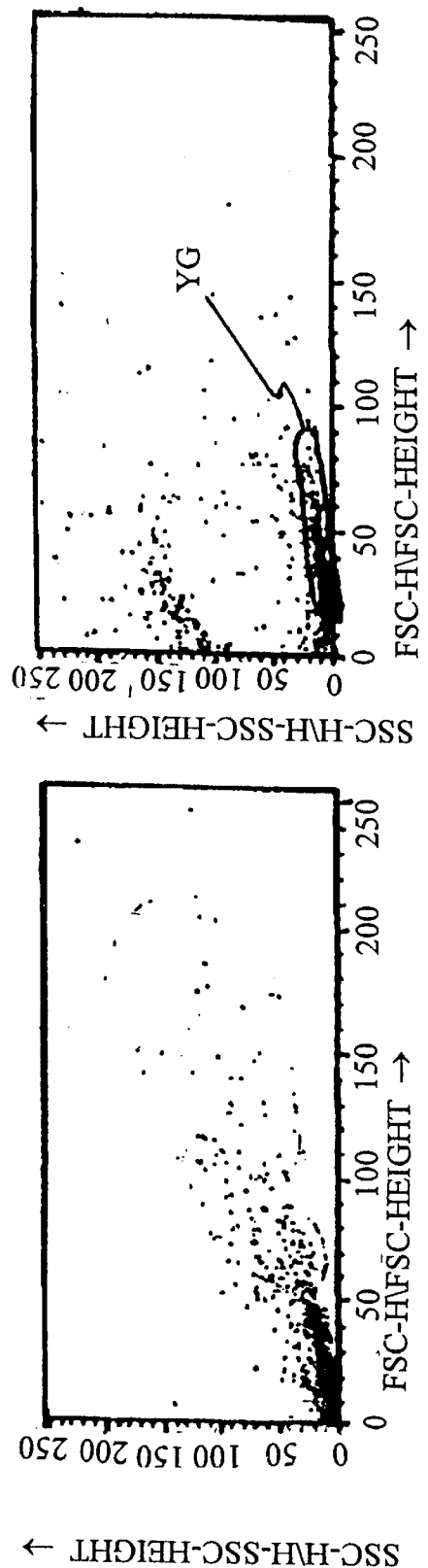
FIGURE 2C
FIGURE 2D
FIGURE 2E
FIGURE 2F

FSC-H\FSC-HEIGHT →

FSC-H\FSC-HEIGHT →

DETECTING EUBACTERIA AND FUNGUS AND DETERMINING THEIR ANTIBIOTIC SENSITIVITY BY USING CATALYTICALLY INACTIVE MUREIN BINDING ENZYMES

This application is a continuation of U.S. patent application Ser. No. 08/823,293, filed Mar. 21, 1997, now U.S. Pat. No. 5,935,804.

FIELD OF THE INVENTION

The invention generally relates to microbiology and reagents and methods for identifying fungi and bacteria in samples of biological fluids, foods, water, air, solutions and the like; and, specifically, to diagnostic reagents and methods for detecting and quantifying fungi and bacteria, as well as, for distinguishing between bacteria and fungi in a sample.

BACKGROUND OF THE INVENTION

Rapid tests for identification of pathogenic bacteria, fungi and their products are becoming increasingly important to health care professionals, as well as individuals responsible for water and food safety. Timely identification and generic classification of etiologic agents is a key to preventing spread of disease, and is also effective to expedite patient treatment and thereby reduce costs associated with disease management.

Microbiological stains are diagnostic reagents capable of identifying bacteria and fungi from cultures, but they commonly are not useful as rapid diagnostic tests with patient samples because of cross-reactivity with natural mammalian and plant products and with other non-pathogenic microorganisms. While gram-staining for bacteria remains a most useful diagnostic criteria in evaluation of isolated bacterial cultures, the reagents and methods generally lacks sensitivity because many groups of bacteria stain either poorly or not at all. Similarly, histological staining of polysaccharides using Grocott methenamine silver nitrate as a test for fungi lacks sensitivity and is subject to confusing non-specific cross-reactions with e.g. connective tissue proteoglycans, glycosaminoglycans and mucins. Commonly, definitive identification and confirmation of infection, or contamination, requires multiple tedious steps of culture and multiple different testing methods and often these procedures are not suitable for use in smaller clinical test laboratories.

Bacterial envelopes are composed of an inner phospholipid bilayer with membrane proteins surrounded by a rigid shell of covalently linked peptidoglycan that is reactive with crystal violet and iodine, i.e., the envelope in gram positive bacteria. Gram-negative bacteria have the latter structure, but with lesser amounts of peptidoglycan, and their envelope includes an additional outer membrane characterized by lipopolysaccharide (LPS), porins and transport proteins. Peptidoglycan structures vary in different bacteria. In *E. coli* peptidoglycan, N-acetylglucosamine alternates with N-acetylmuramic acid in $\beta(1,4)$-glycosidic bonds to form complex polymers with tetrapeptide side chains. The latter side chains are composed of L-Ala-D-Glu-mesodiaminopimelic acid-D-Ala. Cross-linking between peptidoglycan chains forms a gel that varies in consistency dependent upon the degree of cross-linking.

In contrast, most pathogenic fungi contain chitin in their cell walls, septa and spores, both in hyphal and yeast forms. Chitin is a $\beta 1 \rightarrow 4$ linked polymer of only 2-deoxy-2-acetamindoglucose (N-acetyl glucosamine, abbreviated GlcNAc). Chitin is also found in tissues of insects and crustaceans. Certain classes of fungi have cell walls that contain both chitins and murein-like compounds. However, the murein-like compounds are commonly hidden within thick protective cell wall structures, and/or expressed only in low levels. Fungi, as eukaryotes, also have many similarities with mammalian cells, often making it more difficult to distinguish between patient cellular materials and fungal products.

Immunoassays used in clinical microbiology commonly rely on antibodies that, while highly specific, are also narrowly reactive, e.g., with a single defined epitope in a complex carbohydrate structure of a particular serotype of bacteria. Cross-reactivity of reagents with more than one different type of bacteria is often viewed as an undesirable performance attribute. Antibody reagents also frequently are unable to distinguish between a whole bacteria and the degradative products of a bacteria, and as a result breakdown products can act as 'confounding', or 'interfering, substances' in diagnostic assays. Where enzymes are used in immunoassays, they are commonly used to generate a detectable signal. For example, enzyme-linked immunosorbent assays (ELISA) such as those disclosed in U.S. Pat. Nos. 4,233,402 and 4,486,530, involve labeling an antibody (or antigen) by covalently linking it to a catalytically active enzyme. The presence (or amount) of the labeled compound may be determined in an assay by adding an enzyme substrate that produces a measurable signal (e.g., a colored product or fluorescence.) While certain assay formats rely upon re-activation of an inactivated-enzyme (e.g., U.S. Pat. No. 4,043,872), generation of a signal in an ELISA commonly requires a catalytically active enzyme, and preferably one having giving a rapid production of product (i.e., a high turnover number.) Catalytically active enzymes considered for possible use in diagnostic immunoassays include those hydrolyzing glycosidic bonds (e.g., U.S. Pat. No. 4,208,479 at column 17; U.S. Pat. No. 4,299,916 at column 33.)

Enzymes are given names indicating both the principal substrate and the reaction catalyzed. However, few enzymes are absolutely specific to the structure of a particular substrate and most can act on closely related structural analogues of their physiological substrates, although usually at reduced rates. The Commission on Enzymes of the International Union of Biochemistry has evolved a systematic nomenclature for enzymes based on the reactions catalyzed. Lysozyme, classified as a glycoside hydrolase in IUB class EC3.2.1 (i.e., IUB class EC3.2.1.17), has specificity for compounds containing N-acetylmuramic acid and a peptide side chain (i.e., mureins.) Lysozymes from different species catalyze hydrolysis of $\beta(1,4)$ bonds between N-acetylmuramic acid and adjacent sugar residues in mureins and chitins, but chitins more slowly. Chitinase, classified as an N-glycosyl hydrolase (i.e., IUB class EC3.2.1.14), binds and degrades chitin and murein, but murein much more slowly than chitin.

It would be highly desirable for clinical test laboratories to have access to reagents that, while specifically reactive with many genera of bacteria and fungi, are also useful as reagents in assays that distinguish between bacterial and fungal infection or contamination. However, the array of different antigens in bacteria and fungi that are available as potential targets for development of immunoassays is somewhat bewildering. Also, increasingly laboratory personnel are being placed at a potential risk of exposure to debilitating or life threatening diseases by contact with infected patient samples. While it is commonly an aim to conduct all assays with non-infectious materials, the resultant fixed and killed bacterial samples often contain denatured antigens that are poorly reactive with assay reagents. Diagnostic reagents reactive with fixed, and/or killed and dead bacterial and fungal products are highly desirable.

Bacteria, fungi and their products are often present in samples in vanishingly small amounts. Recently, attempts have been made to develop sensitive alternatives to immunoassays by using polymerase chain reaction (PCR) and enzyme-linked oligonucleotide probe methods. (InfectioDiagnostics Corporation of Quebec, Canada has disclosed a PCR test method for detection of bacteria.) Unfortunately, these test methods are often time-consuming, e.g. requiring repetitive thermal cycling for amplification, and also requiring highly trained personnel and special laboratory conditions to insure optimal performance. Reagents and methods capable of rapidly detecting very small numbers of bacteria and fungi in samples would be of great importance in clinical testing of patient materials, as well as in monitoring food, air and water.

Objects of the invention provide reagents and assays for detecting small numbers of killed and treated bacteria and fungi from a wide range of different genera. The reagents and assays are unreactive with any products in normal mammalian tissues and are also capable, in certain objects, of distinguishing between bacterial and fungal infection or contamination. Other objects provide a variety of methods for detecting eubacteria which do not require any special personnel training or facilities for optimizing their use.

SUMMARY OF THE INVENTION

Disclosed herein are reagents and methods for identifying eubacteria, fungi and their products in a wide range of different biological tissues and fluids including patient and veterinary samples, food, air and water. The diagnostic reagents of the invention contain non-antibody murein-binding polypeptides that are substantially purified and preferably modified from their native structure or amino acid sequence, e.g. through genetic or chemical modification(s), to render them most effective in the disclosed methods. Murein-binding polypeptides have amino acid sequences capable of binding to denatured bacterial murein ligands and fungal murein-like ligands as they appear in fixed and denatured bacterial and fungal particles. Murein-binding polypeptides are reactive with the latter murein ligands as they appear in alcohol fixed (e.g., 80% ethanol), or alkaline denatured (e.g., 2M NaOH, 60° C. for 30 minutes) and/or protease treated (e.g., 0.25% trypsin, 37° C., 30 minutes), and/or periodate-treated, and/or acetic anhydride-treated dead bacterial and fungal particles. Binding of the murein binding polypeptides to the murein ligands is high affinity and specific with little or no detectable cross-reactivity with mammalian or plant products. Non-antibody murein-binding proteins include native and catalytically disabled enzymes selected from among murein biosynthetic and hydrolytic enzymes produced by mammals, insects, bacteria, bacteriophage and fungi.

Murein-binding polypeptides are preferably purified substantially for use and may be chemically conjugated to a signal generating compound such as a fluorophore, a magnetic particle, a latex bead or an enzyme, and may also be linked to biotin or avidin. In-situ binding, enzyme-substrate (ISBES) assay methods, disclosed herein, employ the murein-binding polypeptide reagents to detect and quantify bacteria and fungi in-situ, i.e. without isolation and culture. The assay methods include steps for detection of bacteria and fungi in fixed tissue samples by histochemistry; in samples of bodily fluids such as urine by flow cytometry or by enzyme-linked solid phase methods; in blood by machine assay methods or latex dipstick methods; and, in food, air, water samples by dot-blot methods. ISBES sample preparation methods include the step of treating a biological sample to simultaneously effect the following: namely, (i) killing infectious bacterial, fungal or viral agents in the sample to produce dead bacterial and fungal particles; (ii) lysing mammalian cells such as erythrocytes and leukocytes; (iii) disaggregating bacterial and fungal rafts into uniform single cell/particle suspensions; (iv) dissociating bacterial and fungal particles from other possible particulate materials in the samples such as, plant cellulosic and lignin materials; (v) removing exterior fungal cell wall surface layers to expose murein-like compounds in the dead particles; (vi) removing/denaturing mammalian cellular materials that might cross-react in the assay and contribute to nonspecific background; (vii) denaturing bacterial and fungal cell surface polypeptides to increase susceptibility to protease treatments and/or to increase accessibility of murein-like ligands for binding to murein binding polypeptides; and, while (viii) retaining the ability of the dead denatured bacterial and fungal particles to react with natural and modified murein binding polypeptides.

Murein binding polypeptide reagents and ISBES assay methods offer cost-savings and other commercial advantages (e.g., shelf life stability) for manufacturers and users of diagnostic test reagents, kits and reagent packages marketed for detecting bacterial and fungal infections. In addition, quantitative and qualitative flow cytometry and cytofluorimetric ISBES methods are disclosed for determining the presence, severity and type of microbial infection in a patient by detecting and quantifying the number of bacterial and/or fungi in a biological sample which are reactive with a murein binding polypeptide reagent. The latter particle size and light scattering ISBES methods allow rapid quantification and/or discrimination between bacteria and fungi in patient samples, and are not effected by the presence of cell wall fragments. Kits are also disclosed for identifying eubacteria and fungi in samples of air, water and biological samples.

BRIEF DESCRIPTION OF THE DRAWINGS

FIG. 2C shows a plot of fluorescence intensity (x axis; FSC-H/FSC-Height) against particle size (y axis: SSC-H/SSC-Height) for unstained negative control urine sediment residue particles in a normal human urine sample that was subject to chemical treatments and fluorescent staining with an MBP-conjugate according to the invention, as disclosed further below and illustrated in EXAMPLE 8. The circle labeled "YG", yeast gate, denotes the data point region where killed and denatured fungal particles, if present, would be recorded.

FIG. 2D shows a plot of fluorescence intensity (x axis) versus particle size (y axis) for a negative control urine sediment sample prior to any chemical treatments; as disclosed further in EXAMPLE 8, below.

FIG. 2E shows a plot of fluorescence intensity (x axis) versus particle size (y axis) for a biological sample containing fungal particles which are indistinguishable in this analysis from normal human urine sediment particles; as disclosed further in EXAMPLE 8, below.

FIG. 2F shows a plot of fluorescence intensity (x axis) versus particle size (y axis) for the fungal sample of FIG. 2E, above, after chemical treatments and fluorescence staining with an MBP-conjugate according to the methods of the invention, and as disclosed below and illustrated in EXAMPLE 8. The circle labeled "YG" contains data points recorded primarily from killed and denatured singlet and doublet fungal particles and is separated from the majority of the other urine sediment particles.

FIG. 9A shows all of the data points while FIG. 9B shows only those data points corresponding with a particle size and particle fluorescence intensity that was appropriate for yeast, i.e., 'yeast gate' data, as disclosed further below in EXAMPLE 8.

FIG. 10A shows all of the data points while FIG. 10B shows only those data points corresponding with a particle size and particle fluorescence intensity that was appropriate for yeast, i.e., 'yeast gate' data, as disclosed further below in EXAMPLE 8.

FIGS. 11A and 11C show all of the data points collected on day 1 or day 2, respectively, while FIGS. 11B and 11D shows only those data points corresponding with a particle size and particle fluorescence intensity that was appropriate for yeast, i.e., 'yeast gate' data, as disclosed further below in EXAMPLE 8.

DETAILED DESCRIPTION OF THE PREFERRED EMBODIMENT

Figure 1A:
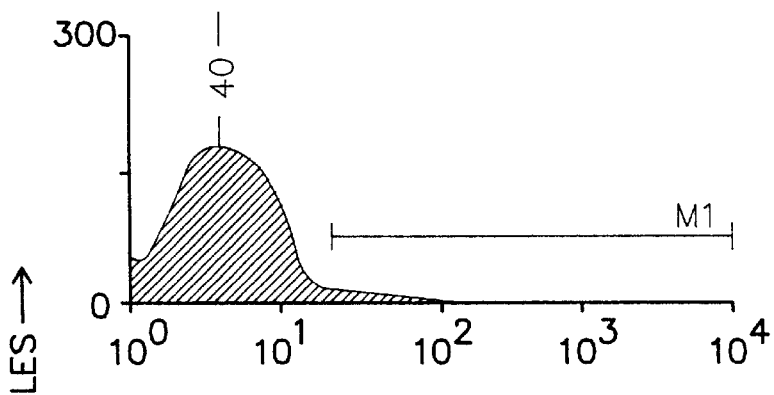
FIG. 1A shows the background auto-fluorescence of bacteria as measured by flow fluorimetry.

Documents cited herein by identification number, e.g. (1), are listed in the Citations section which follows the Examples section, below.

In retrospect, few aspects of the present invention could have been expected based on the experience in the art at the time of the invention. For instance, $K_a$'s for binding of native lysozyme to chitotriose are in the range of $1.1 \times 10^5$ L/mol (3), $0.9–1.7 \times 10^5$ L/mol (4); and for binding of catalytically inactivated lysozymes to chitotriose are in the range of $4.4 \times 10^5$ L/mol ($Gln^{35}$), $4.0 \times 10^5$ L/mol ($Asp^{52}$) (4). While chemically inactivated and mutant lysozymes, their methods of preparation, and their binding affinities had been disclosed previously, the compositions in the art were generally not suitable for preparation of a diagnostic reagents for the following reasons: namely, 1. Catalytically active lysozymes degrade murein compounds;
2. Chemically inactivated lysozyme enzyme preparations were, in many cases, not of sufficient purity for use, and if pure, often contained active enzyme as a contaminant and/or were not stable because they underwent regeneration of enzyme activity (5);
3. Catalytically inactive lysozyme reportedly binds nonspecifically to human rbc, mouse rbc, chicken rbc, and Hep G2 cells as strongly as the lectin wheat germ agglutinin (6) creating an unacceptably high background;
4. Normal human serum, lymphocytes, monocytes and PMNs reportedly contain endogenous chitinases (7) that could constitute confounding or interfering substances in a diagnostic assay;
5. Lysozyme known to be present in biological samples, e.g., secretions, at high levels and is also a major cationic protein in the azurophil and specific granules of PMN (7,11) which are released into inflammatory secretions;
6. Bacterial and fungal cell wall components such as $(GlcNAc-MurNAc)_2$ are known inhibitors of lysozymes (5; Ka $4.2 \times 10^3$) and capable of inhibiting these enzymes in a diagnostic assay format; and,
7. Bacterial LPS is a reported non-competitive inhibitor of lysozyme which has a Ka for binding in the range of $10^8$ L/mol (11).

In consideration of these factors, mammalian cell debris in biological samples would be expected to constitute an unacceptable high background preventing use of lysozymes and chitinases in diagnostic assays. In addition, bodily fluids would be expected to contain endogenous lysozymes and chitinases capable of acting as both potential interfering substances in diagnostic assay; and as hydrolases cleaving the analytes in a murein-binding diagnostic assay. Bacterial and/or fungal cell wall materials and biosynthetic products would also be expected to inhibit the binding of a murein binding polypeptide to bacterial and/or fungal cell wall analyte. Thus, in retrospect, the disclosure in PCT/US92/02593 (Tuse et al.; filed first in April of 1991 and without benefit of present day understanding) was not justified in its prophetic assumptions that chitinase (or lysozyme) could be used in diagnostic assays without significant and undue experimentation. Similarly, while Benjaminson (9) and Chamberlain (8), which disclosed use of F-NHS-chitinase for detecting chitin in histologic sections of plant tissues, is not helpful in determining how one might proceed from a plant histochemical assay to a non-histologic diagnostic assay useful with biological samples of air, water, food, or bodily fluids. The Tuse international patent application (supra) did not apparently disclose catalytically inactive murein binding proteins.

Binding of lysozyme and other murein binding polypeptides to denatured, fixed and killed bacterial and fungal particles is also believed to have been unknown at the time of the invention, including binding to bacterial murein compounds, or fungal murein-like compounds in dead bacterial and fungal particles after alcohol fixation (e.g., 80% ethanol), alkaline denaturation (e.g., 2M NaOH at 60° C. for 30 minutes), and/or protease treatment (e.g., 0.25% trypsin at 37° C. for 30 minutes), and/or treatment with periodate, N- or O-glycosidases and/or treatment with acetic anhydride (as disclosed further below); or, that the subject binding with these denatured particles would be of sufficient affinity (e.g., greater than nanomolar binding) and with little or no detectable cross-reactivity (e.g., with mammalian and plant food substances), so as to enable use of the reagents prepared from these murein binding polypeptides in diagnostic assay formats.

The following properties of the instant in-situ binding enzyme-substrate (ISBES) methods were also believed to be unknown: namely, that treating certain types of biological samples could simultaneously effect the following: namely, (i) killing infectious bacterial, fungal or viral agents in the sample to produce dead bacterial and fungal particles; (ii) lysing mammalian cells such as erythrocytes and leukocytes; (iii) disaggregating bacterial and fungal rafts into uniform single cell/particle suspensions; (iv) dissociating bacterial and fungal particles from other possible particulate materials in the samples such as, plant cellulosic and lignin materials; (v) removing exterior fungal cell wall surface layers to expose murein-like compounds in the dead particles; (vi) removing/denaturing mammalian cellular materials that might cross-react in the assay and contribute to nonspecific background; (vii) denaturing bacterial and fungal cell surface polypeptides to increase susceptibility to protease treatments and/or to increase accessibility of murein-like ligands for binding to murein binding polypeptides; and, while (viii) retaining the ability of the dead denatured bacterial and fungal particles to react with natural and modified murein binding polypeptides.

Embodiments of the invention provide murein-binding polypeptides and peptides (inclusively abbreviated MBP) that are capable of binding to a wide variety of different bacterial mureins and fungal murein-like compounds in a highly specific and saturable manner. While mureins are present in higher concentrations in gram-positive bacterial cell walls, they are also present (at lower concentrations) in gram-negative, other eubacteria and murein-like compounds are present in certain fungi. The highly sensitive and specific reagents and ISBES assay methods disclosed herein allow detection of bacterial murein compounds and murein-like fungal compounds even when present at relatively low concentrations. Preferably, the subject MBP have a binding affinity for diose, triose and tetraose bacterial and fungal cell wall compounds that is in the range of about $10^{-3}$ L/mol to about $10^{-5}$ L/mol; and, the subject compounds are effective to bind the subject murein or murein-like compound with a association constant ($K_a$) in the range of about $5 \times 10^{-5}$ L/mol to about $10^{-9}$ L/mol, preferably $5 \times 10^{-7}$ L/mol to $10^{-9}$ L/mol, and most preferably greater than $10^{-9}$ L/mol. The subject pan-reactive murein-binding proteins are used in a substantially purified form to formulate reagent preparations for use in diagnostic assays. Substantial purity may be achieved e.g. by biochemical purification from natural sources, or from selected bacterial, fungal, mammalian, avian, or insect sources; or, from the product of a genetically engineered expression system. Preferably, the instant murein-binding polypeptides (or peptides) are synthetic, modified, mutated, chemically inactivated and/or genetically re-engineered non-antibody polypeptides (or peptides) that take their origin from a variety of different wild-type polypeptides exhibiting an intrinsic binding affinities and specificities for bacterial mureins. The subject wild type murein-binding polypeptides suffer from certain disadvantages that may discourage their use in diagnostic assay formats, i.e. they may have a binding affinity for murein that are too low to encourage their use as a pan-bacterial reagent; or, they may be cross-reactivity with other bacterial carbohydrates and lack specificity; or, they may have a large and cumbersome molecular size that discourages their use because of the cost of materials required to run an assay ; or, they may be catalytically active and degrade mureins into soluble peptidoglycan products that are not longer detected in a diagnostic assay format. Representative examples of wild type catalytically active polypeptides that bind and cleave mureins include, but are not limited to, bacterial, fungal, mammalian, insect and avian bacterial cell wall degrading enzymes: e.g., muramidases, lysozymes, chitinases, β-glucosidases as well as murein biosynthetic and degradative enzymes, (e.g. catalyzing the reverse reaction.) Other representative examples of wild type precursors for the subject murein-binding proteins include lectins, and hybrid molecules, e.g., derived by recombinant or protein cross-linking methods. In general, wild-type (i.e., natural) murein-binding polypeptides are tested to determine whether their binding affinity falls within the range requisite for use in an assay according to the instant invention; in particular the subject wild-type murein binding polypeptides are tested to determine whether they will bind to killed and denatured bacteria and fungal particles according to the steps of the instant ISBES method (supra); and, whether the subject wild-type polypeptides contain enzymatic activity and whether that activity can be tolerated in an assay according to the instant ISBES methods (supra.) Preferably, the subject murein-binding polypeptides have less than 10% of the catalytic activity of a wild-type murein parental polypeptide. Most preferably, the subject murein-binding polypeptides have less than 5% of the catalytic activity of a wild-type polypeptide. However, as illustrated in the Examples section below, the chemical treatment steps (supra) of the instant ISBES assay methods allowed the detection of killed and denatured bacterial and fungal particles in urine sediments using a fluorescent conjugate of wild-type catalytically active hen egg white lysozyme.

Binding affinity (supra), choice of MBP (supra) and the steps of the instant ISBES assay method (supra) are considered key factors in achieving success in the commercial diagnostic assays provided by the embodiments of the invention. Most preferably, embodiments of the invention provide MBP compositions having binding affinities ($K_a$) in excess than $10^{-9}$ L/mol, and most preferably MBP compositions that are substantially pure preparations consisting of MBP that have a binding site capable of binding several sugar residues constituting the polysaccharide backbone (i.e., a spatial motif) of a murein ligand. The subject spatial motif preferably has about 4 to about 8 sugar residues, most preferably about 4 to about 6, with at least 2 of the residues selected from among N-acetylglucosamine and N-acetylmuramic acid. Most preferably, the subject spatial motif has about 6 sugar residues, with at least 2 of the residues selected from among N-acetylglucosamine and N-acetylmuramic acid. Natural or catalytically inactivated hen egg white lysozyme is a representative example of a murein binding composition having a binding site that recognizes a 6 sugar spatial binding motif in murein, and related compounds, and recognizes murein and murein-like compounds in killed and denatured bacterial and fungal particles prepared according to the instant ISBES assay methods. Catalytically inactive chitinase is one representative example of a murein binding composition having a binding site that recognizes a 4 sugar spatial binding motif in chitin and related compounds.

Embodiments of the invention provide, uniformity of compositions capable of conferring specificity and sensitivity on diagnostic assay. The subject compositions enable preparation of diagnostics reagents within the precise bounds necessary for regulatory compliance according to quality control and quality assurance protocols. The subject compositions have high binding affinity and advantageous stability at different temperatures and on a storage shelf-life (i.e., shelf-life stability.) In one presently preferred embodiment, catalytically inactive lysozyme is stable at acid pH (i.e., pH 4) and resists heating at 100° C. at pH 4.5 for about 3 minutes. The subject high binding affinity and physical stability enables rapid commercially viable assay formats, i.e., requiring less than about 15 minutes to accomplish binding between an MBP and an analyte in a biological sample, preferably less than about 2 minutes to about 40 seconds, and most preferably about 6 seconds to about 1 second. The subject high binding affinity MBP also provides a favorable cost of goods, and lower cost-per-assay since only small amounts of reagents and time are necessary to obtain an assay result. Shelf-life stability of the subject liquid and powdered compositions of the invention, often problematic in the diagnostics industry, was found to be excellent.

Embodiments of the invention provide diagnostic reagent solutions useful for detecting a murein compound in a biological sample according to one or more of the instant assays. Reagent solutions are optimized to facilitate specific binding interactions between the subject MBP and a murein ligand by choice of additives, buffers, stabilizers and the like. In one presently preferred embodiment, the subject reagent solutions were optimized for use in the instant assays by adding (i) non-polar solvents; and/or (ii) agents displacing water (e.g., polyethylene glycol, sucrose, and the like); and/or (iii) detergents (e.g., NP 40) to a pH balanced buffer salt solution (e.g., $Na^+$, $K^+$, $Li^+$ and the like) of a MBP or MBP-SGC compound. MBP compounds having hydrophobic residues inserted into the MBP protein, or having ionically, hydrophobically, and covalently linked polyethylene (PEGylated) may exhibit increased murein binding activity.

Embodiments of the invention provide highly sensitive and specific non-antibody diagnostic MBP reagents reactive with a wide range of different bacteria and fungi. The subject reagents consist of one or more MBP, each capable of binding a murein compound present in a eubacteria, or a murein-like compound present in fungi and as the subject compounds are present in a killed, fixed and treated biological samples.

Other embodiments provide pan-reactive non-antibody MBP diagnostic assays useful for detecting bacteria and fungi in a biological sample that has been fixed (e.g., in an organic solvent such as alcohol) or chemically treated (e.g., with an acid or base) to kill infectious materials and thereby to reduce the risk to laboratory personnel.

Other embodiments provide non-antibody diagnostic reagents and assay methods for: (i) distinguishing between bacteria and fungi in a biological sample that may contain plant and/or mammalian cellular materials; (ii) discriminating between fragments of bacteria or fungi and whole bacterial or fungal cells in a biological sample (i.e., based on size); and, (iii) identifying and/or quantifying fungal cells in a biological sample containing bacterial cells, bacterial spores, fungal spores, or plant or mammalian cellular materials or fragments of any thereof. Representative assay methods for distinguishing, discriminating and quantifying according to the instant assays methods are illustrated in the Examples section, below, and include use of flow cytometry.

In other embodiments, the invention provides reagents and methods useful for (i) treating a fluid biological sample to increase the single cell content of a suspension of fungal cells; and, (ii) rendering the cell suspension suitable for detecting and/or quantifying the extent of contamination of the sample, or the presence or severity of an infection in a patient through the process of identifying and/or quantifying a number of fungal cells in a defined volume of the subject biological sample. The instant reagents and methods are useful for treating fluid biological samples that contain one or more of the following: namely, (i) fungal hyphae, (ii) rafts, aggregates or clumps of yeast cells, (iii) fungal cells in combination with bacterial cells or their products, (iv) fungal cells in combination with plant cells or their products, including plant cell wall materials, (v) fungal cells in combination with mammalian cells or their products, including mucins, lipids, lipopolysaccharides, glycolipids, proteoglycans and the like. Representative diagnostic reagents and assay methods are illustrated in the Examples section, below.

In yet other embodiments, the invention provides a relatively inexpensive source of MBP diagnostic reagents that are constitutively expressed at high levels in relatively inexpensive bacterial, fungal, insect, mammalian and/or plant tissues, cells or cell cultures.

In other aspects, the invention provides simple diagnostic tests that do not require specialized personnel training or facilities, and use equipment that is commonly available in a clinical test laboratory, e.g., a clinical centrifuge, components supplied in the instant kit (below) with accompanying instruction.

Embodiments of the invention also provide pan-bacterial and pan-fungal diagnostic reagents referred to herein as MBP-SGC conjugates, consisting of an MBP compound, preferably having a molecular size of about 55 kilodaltons (KD) to about 12 KD, most preferably about 35 KD to about 12 KD, that is linked through ionic, hydrophobic and covalent bonds to a signal generating compound (SGC.) The subject MBP-SGC conjugates have a high binding affinity for bacteria and fungi; a low catalytic activity for murein substrates as they appear in killed and denatured bacterial and fungal particles according to the instant ISBES methods; and, have a low binding affinity for degraded soluble bacterial and fungal cell wall products. The subject MBP-SGC conjugates, contain a non-antibody MBP that, unlike antibody reagents, does not contain an Fc portion capable of binding complement C1q, nor an antigen binding site capable of cross-reacting with related antigens, nor a molecular size of 135–150 KD, nor an antibody structure or charge distribution that can contribute to nonspecific electrostatic or hydrophobic binding interactions.

Embodiments of the invention provide in-situ binding enzyme-substrate (ISBES) assay methods for detecting and/or quantifying bacteria and fungi in biological samples. The instant methods include a step of killing bacteria and/or fungi in a biological sample by treatment with a fixative, or alternatively, a chemical. The instant chemical treatment preferably is an alkaline treatment conducted at a temperature of about 20° C. to about 100° C., preferably about 37° C. to about 100° C. and most preferably at about 60° C. to about 70° C. The instant alkaline treatment is conducted using a solution of a base at a concentration and for a time effective to denature a bacterial or a fungal polypeptide. Representative examples of the instant fixatives include alcohol solutions such as ethanol, methanol and isopropanol, as well as aldehyde solutions such as formaldehyde, paraformaldehyde and glutaraldehyde. Representative examples of the instant chemical base solutions so useful include strong inorganic and organic bases such as about 0.5 M to about 5 M sodium hydroxide; about 0.5 M to about 3 M potassium hydroxide; 1 M to about 2.5 M ammonium hydroxide and the like. Preferably the chemical base solution is about 1 M to about 5 M sodium hydroxide, and most preferably about 2 M sodium hydroxide for use at the preferred and most treatment temperature and time (supra.) Illustrative concentrations and treatment times effective to denature a fungal or bacterial polypeptide are disclosed in the Examples section below. "Denature" is intended to mean disrupting secondary and tertiary polypeptide structure involved e.g. in protein folding. Methods for determining protein denaturation are known in the art and include at least comparative scanning spectrophotometry e.g., in the UV and near UV, molecular sieve chromatography, sucrose density gradient ultracentifugation, SDS-PAGE under non-denaturing conditions (e.g., Osborne gels) and the like. Times effective to denature a fungal or bacterial polypeptide are dependent upon the temperature, determinable by one or more of the subject methods, and will generally be in the range of about 2 minutes to about 30 minutes. The instant ISBES assay methods include assay formats in which detection or quantification of bacteria or fungi is conducted in-situ in fixed tissue samples by histochemistry; in samples of bodily fluids such as urine and blood by flow cytometry or by enzyme-linked solid phase methods, machine assay methods or latex dipstick methods; and, in food, air, water samples by dot-blot methods. It has been found that the instant step of using a fixative or a chemical base to effect denaturation of a bacterial or a fungal polypeptide, enables the optional use of either a natural murein-binding polypeptide (i.e., catalytically active and not genetically or chemically inactivated), or a catalytically disabled murein-binding polypeptide in the subject ISBES assay. Apparently, murein ligands in killed and denatured bacterial and fungal particles function as ligands for enzymatically active natural polypeptides but turnover of the subject substrates in the denatured particles is sufficiently slow to allow their use in certain ISBES assay formats. Those skilled in the art will recognize that comparative determinations can be made of natural and catalytically inactive murein-binding polypeptides in a test ISBES assay format, and that a determination can be made of whether the subject natural polypeptides has performance characteristics allowing its use in an assay, e.g. performance including specificity, sensitivity, precision, background, cross-reactivity with non-murein compounds and reproducibility. Catalytically disabled murein binding polypeptides are preferred for use in ISBES assay formats, as disclosed further below.

In optional embodiments, the instant ISBES assay methods include a step, i.e., conducted after the fixative or alkaline treatment, of washing the denatured biological sample to remove the fixative or chemical base, or neutralizing the base e.g. with HCl, and then treating with a solution of a protease, a glycosidase, a sialidase or a periodate. The subject second treatment step is effective to further reduce background non-specific signal generated in an ISBES assay and to increase accessibility of murein and murein-like compounds in bacterial and fungal cell wall for binding to the instant murein binding polypeptide reagents. One or more protease treatments hydrolyze bacterial and fungal cell surface proteins exposing murein and murein-like compounds, and at the same time degrade mammalian and plant compounds which might constitute background reactivity in an assay. Representative proteases solutions include trypsin at about 0.1% w/v to about 1% w/v, pronase at about 0.25% to about 2% w/v, subtilisin at about 0.05% to about 1% and the like. Preferably the protease solution is about 0.25% to about 1% trypsin. Glycosidases remove cell surface carbohydrates from bacterial and fungal cells, exposing mureins and murein-like compounds and degrading potential mammalian and plant cross-reacting materials which might contribute to background in an assay. Representative glycosidase solutions include both N- and O-glycosidases at concentrations of about 50 µg/ml to about 10mg/ml. Sialidases remove charged sialic acid from cell surface carbohydrates in mammalian and eubacterial and fungal cells. The resultant reduction in cell-surface charge may decrease non-specific background in an assay. Representative sialidases include commercially available N-acetyl neuraminidases from several sources (Sigma Chemical Co., St. Louis, Mo.) Periodate removes sugar residues at vicinal hydroxylgroups, increases availability of murein-like compounds in fungi for binding to MBP, and decreases background reactivity with complex carbohydrates synthesized by mammalian cells, e.g., erythrocytes, leukocytes, tissue cells, tumor cells and the like. Representative periodate solutions include sodium periodate at a concentration of about 0.1% to about 1%. In yet other optional embodiments, the instant second treatment step may include sequential treatments with one or more chemical base, one or more protease, one or more glycosidase and/or the periodate, e.g., 1M KOH treatment followed by an optional protease treatment to expose murein and murein-like compounds in bacteria and fungi in histopathologic tissue sections collected from infected animals (i.e., man and domestic animals), as well as, for solubilizing potentially cross-reactive mammalian tissue materials.

In yet other optional embodiments, the instant ISBES assay methods include a step, i.e., conducted after the fixative or alkaline treatment or after the instant second step, of washing the denatured biological sample to remove any fixative, chemical base or second treatment step compound, and then treating with a solution of an anhydride effective to accomplish N-acetylation of carbohydrate compounds in the denatured bacterial or fungal particles. The subject N-acetylation step is effective to increase the sensitivity, e.g., number of bacteria or fungi required for identification or quantification, of an instant ISBES assay probably by increasing the binding of a murein-binding polypeptide with the a murein or murein-like compound in the subject killed and denatured fungal or bacterial particle. Most preferably, the means for N-acetylation consists of conditions suitable for N-acetylation of polysaccharides, e.g., in a suitable buffer pH 8. Representative examples of anhydride solutions so useful include about 2% (v/v) to about 5% (v/v) acetic anhydride in sodium bicarbonate buffer at pH 8, and about 0.2 M to about 0.5 M acetyl chloride in sodium bicarbonate buffer at pH 8.

In other embodiments the invention provides reagents and methods for conducting rapid high through-put continuous-flow cytometric assays. In one presently preferred embodiment, the subject cytometry assay is a cytofluorimetric assay, and most preferably the subject cytofluorimetric assay is capable of quantifying a number of bacterial or fungal cells in a biological sample collected from a subject in need thereof, thereby to determine the presence and/or severity of an infection in the subject. In another presently preferred embodiment, the subject cytometry assay is a cytofluorimetric assay, and most preferably the subject cytofluorimetric assay is capable of quantifying a number of bacterial or fungal cells in a biological sample collected from food, water or air, thereby to determine the presence and/or amount of contamination in the sample. In an alternative preferred embodiment, the subject cytofluorimetric assay consists of a simultaneous assay format having the steps of (i) binding a non-antibody MBP-SGC conjugate to a bacterial or a fungal cell; (ii) discriminating between the bacterial and the fungal cell, or degradative products of these cells, (e.g. by size or fluorescence intensity), thereby to identify the microbial source (bacterial or fungal) of an infection in a subject in need thereof. In yet another alternative preferred embodiment, the subject cytofluorimetric assay provides a rapid method for determining the antibiotic sensitivity of a bacteria or a fungi in a biological sample. The subject assay involves the steps of (i) quantifying the number of bacterial or fungal cells in a biological sample; (ii) culturing an aliquot of the biological sample for a period of time and under conditions suitable for growth of the bacteria or the fungus in the presence or absence of an antibiotic; and, (iii) determining the bacteria or fungi to be antibiotic sensitive if growth occurs in the absence of antibiotic but not in the presence of antibiotic. Representative times for culture of biological samples containing bacteria are about 2 to about 6 hours, preferably about 2 to about 4 hours, and most preferably about 2 hours. Representative times for culture of biological samples containing fungi are about 2 hours to about 20 hours, preferably about 2 hours to about 8 hours and most preferably about 3 hours to about 6 hours.

Yet other embodiments of the invention provide murein binding polypeptide reagents and ISBES assay methods that offer cost-savings and other commercial advantages (e.g., shelf life stability) for manufacturers and users of diagnostic test reagents, kits and reagent packages marketed for detection of bacterial and fungal infections. Representative examples of the subject assay methods are provided below in the Examples section below.

Embodiments of the invention provide murein-binding polypeptides prepared for use as pan-bacterial and pan-fungal diagnostic reagents by chemically conjugating the subject MB-polypeptide to a signal generating compound. Representative signal generating compounds are disclosed below, and illustrated in the Examples section. The subject murein binding polypeptide as it is conjugated with a particular signal generating compound may optionally be linked through an additional chemical linking group to a magnetic particle, or to capture compounds such as biotin and avidin.

Embodiments of the invention provide in-situ binding, enzyme-substrate (abbreviated herein ISBES) assay methods, disclosed herein, employ murein-binding polypeptide reagents to identify bacteria and fungi in-situ, i.e. without isolation and culture. For example, the reagents may be used to detect bacteria or fungi in-situ in fixed tissue samples by histochemistry; in samples of bodily fluids such as urine and blood by flow cytometry or by enzyme-linked solid phase methods, machine assay methods or latex dip-stick methods; and, in food, air, water samples by dot-blot methods. ISBES sample preparation methods include chemically treating certain types of biological samples to simultaneously effect the following: namely, (i) killing infectious bacterial, fungal or viral agents in the sample to produce dead bacterial and fungal particles; (ii) lysing mammalian cells such as erythrocytes and leukocytes; (iii) disaggregating bacterial and fungal rafts into uniform single cell/particle suspensions; (iv) dissociating bacterial and fungal particles from other possible particulate materials in the samples such as, plant cellulosic and lignin materials; (v) removing exterior fungal cell wall surface layers to expose murein-like compounds in the dead particles; (vi) removing/denaturing mammalian cellular materials that might cross-react in the assay and contribute to nonspecific background; (vii) denaturing bacterial and fungal cell surface polypeptides to increase susceptibility to protease treatments and/or to increase accessibility of murein-like ligands for binding to murein binding polypeptides; and, while (viii) retaining the ability of the dead denatured bacterial and fungal particles to react with natural and modified murein binding polypeptides.

Embodiments of the invention also provide quantitative and qualitative flow cytometric and cytofluorimetric ISBES methods for determining the presence, severity and type of microbial infection in a patient by detecting and quantifying the number of bacterial and/or fungi in a biological sample which are reactive with a murein binding polypeptide reagent. The latter particle size and light scattering ISBES methods allow rapid quantification and/or discrimination between bacteria and fungi in patient samples, and are not effected by the presence of cell wall fragments.

Embodiments of the invention provide kits for identifying eubacteria and fungi in samples of air, water and biological samples. Representative examples of the subject kits are contained within a box that has a set of instructions and an opening for one or more containers (e.g. bottles, reagent packages and the like) for holding the following solutions or powders: namely, (i) a solution or powder comprising a murein binding polypeptide conjugate having a signal generating compound and a buffer; (ii) an optional solution for resuspending the subject conjugate; (iii) a solution of a chemical base compound, for killing bacteria and fungi and denaturing a bacterial or a fungal polypeptide; (iv) an optional solution for neutralizing the base; (v) an N-acetylation buffer and reagent; (vi) an optional solid phase MBP-capture (as disclosed further below and illustrated in the Examples section); wherein, all of the subject reagents are present in the kit in a form suitable for use in an ISBES assay method conducted according to the steps of the instructions included within the kit.

As used herein the symbols for amino acids are according to the IUPAC-IUB recommendations published in *Arch. Biochem. Biophys.* 115:1–12, 1966 with the following single letter symbols for the amino acids: namely,

---

L, Leu, Leucine
I, Ileu, Isoleucine
M, Met, Methionine
T, Thr, Threonine
F, Phe, Phenylalanine
V, Val, Valine
P, Pro, Proline
G, Gly, Glycine
A, Ala, Alanine
S, Ser, Serine
Y, Tyr, Tyrosine
W, Trp, Tryptophan
N, Asn, Asparagine
Q, Gln, Glutamine
C, Cys, Cysteine
D, Asp, Aspartic Acid
E, Glu, Glutamic Acid
K, Lys, Lysine
R, Arg, Arginine
H, His, Histidine

---

The symbols for protective groups used in the synthetic process are described in Schrödex and Lüibke, "The Peptides", Academic Press, N.Y. 1965, e.g., Boc, t-butyloxycarbonyl and Bzl, benzyl. Other abbreviations include: e.g., HPLC, high pressure liquid chromatography; TFA, trifluoroacetic acid; $K_D$, dissociation constant; Ka, association constant; Keq, equilibrium constant; kcat, enzyme catalytic constant; Km, Michaelis Menten enzyme constant; $V_{max}$ maximal theoretical enzyme velocity; FITC, fluorescein isothiocyanate; RITC, rhodamine isothiocyanate; F-NHS, N-hydroxy-succinimidyl-fluorescein; HRP, horse radish peroxidase; AP, alkaline phosphatase; Ac, for an acetyl group; Gal, for a galactosyl group; Glu, for a glucosyl group; GlcNAc, N-acetylglucosamine; Glu, glucose; MB, murein binding; MBP, for murein binding polypeptide (or peptide); kD, kilodaltons molecular size; kcat/Km, a measure of enzyme catalytic efficiency expressed as the catalytic constant divided by the Km; PBS, phosphate buffered saline; ELMBA, enzyme-linked murein binding assay; ELISA, enzyme-linked immunosorbent assay (not an object of the invention); and, FMBA, fluorescent murein binding assay; SGC, signal generating compound.

Terms used herein are intended to have meaning as follows: namely, "Eubacteria" is intended to mean a bacteria having a murein compound detectable using the reagents and/or methods of the invention as disclosed further below, and as relying in particular upon a diagnostic reagent containing a murein binding polypeptide (or peptide)-conjugate according to the instant definitions and accompanying disclosure. Representative eubacteria include: gram negative bacteria, gram positive bacteria, mycobacteria, spores from bacteria, and the like. Representative eubacteria in biological fluids (as defined below) include: chlamydia, toxoplasma, staphylococci, streptococci, gonococci, pneumococci, and the like. Representative eubacteria in biological samples of air (as defined below) include Legionella, spores of anthrax, and the like. Representative eubacteria in food samples include staphylococci, *E. coli*, Clostridium and the like.

"Fungi" is intended to mean a eukaryotic cell having a nuclear membrane and cell wall. The subject fungi may grow as single cells (e.g., yeasts), chains (e.g., hyphae), aggregates, rafts and the like, and are not plant or mammalian cells. The subject fungi contain a murein-like compound capable of binding an MB polypeptide or peptide as e.g. detectable using the reagents and/or methods of the invention (disclosed further below.) Representative examples of murein-like compounds that may be detected by the subject diagnostic reagents include fungal compounds containing N-acetyl-glucosaminoglucans. Representative fungi include: Aspergillus sp., Candida sp., Cryptococcus sp., Histoplasma sp., Coccidiomycosis sp., Sacchromyces sp., Blastomyces sp., Actinomycetes sp. and the like.

"Murein" is intended to mean a macromolecular cross-linked cell wall assembled by eubacteria from several individual linear unbranched muropolysaccharide backbones each consisting of both of the amino sugars N-acetylglucosamine and N-acetylmuramic acid. The subject several muropolysaccharide backbones are cross-linked together by amide bonds formed between carboxylic acid groups in muramic acids and short oligopeptide side chains and peptide bonds formed between adjacent oligopeptide side chains. The subject cross-linked compounds form 2- or 3-dimensional networks. The subject murein compounds are not small polysaccharide chains such as dioses, trioses or tetraoses. Representative mureins are commonly found in higher concentrations in gram-positive bacteria, but are also present (albeit in somewhat lesser amounts) in gram-negative bacteria, mycobateria, bacterial spores, fungi and the like. The subject murein compounds, when present in biological samples under measurement in the instant assays are referred to herein as "analytes".

"Murein-like" compounds is intended to mean a macromolecular cross-linked cell wall compound assembled by a eubacteria or a fungi from several individual unbranched glycosyl backbones consisting of either N-acetylglucosamine or N-acetylmuramic acid. The subject murein-like compounds are not small polysaccharide chains such as dioses, trioses or tetraoses. Further, the subject compounds are distinguished by their ability to bind a murein-binding polypeptide and to function as an analyte in an assay according to the instant invention.

"Analyte" is used herein to refer to a compound present in a biological sample whose determination is of interest to a user of the instant methods, wherein the subject analyte contains at least one murein compound (supra) or one murein-like compound (supra.) Representative examples of analytes include intact fungal and eubacterial cells, secreted bacterial and fungal cell wall murein compounds (supra), degradative products thereof such as cell wall fragments, peptidoglycans complexes in solution, and the like.

"Chitin" is used herein to refer to cross-linked unbranched chains composed of only β-(1,4)-2-acetamido-2-deoxyglucose, also known as N-acetyl-D-glucosamine.

"Murein binding polypeptide" is used interchangeably with the abbreviation

"MB-polypeptide" to refer to a polypeptide that is composed of about greater than about 5000 molecular weight and consisting of amino acids arranged in a serial array with each amino acid peptide bonded to its neighboring amino acid in a secondary structure. Preferably, the subject MBP have a binding affinity for diose, triose and tetraose bacterial and fungal cell wall compounds that is in the range of about $10^{-3}$ L/mol to about $10^{-5}$ L/mol and are effective to bind the subject murein or murein-like compound with a association constant ($K_a$) in the range of about $5 \times 10^{-5}$ L/mol to about $10^{-9}$ L/mol, preferably $5 \times 10^{-7}$ L/mol to $10^{-9}$ L/mol, and most preferably greater than $10^{-9}$ L/mol. Representative examples of murein-binding wild-type polypeptides that may prove suitable for preparing murein-binding polypeptide non-antibody diagnostic reagents include, e.g.: (i) enzymes capable of hydrolyzing a murein substrate, e.g. selected from among lysozymes (as disclosed in EXAMPLE 1, below); (ii) lectins binding to a murein; (iii) bacterial enzymes involved in bacterial cell wall synthesis, turnover and/or degradation; (iv) fungal or viral enzymes involved in murein degradation (e.g., Pseudomonas autolysins, bacteriophage T4 lysozyme); and (v) peptidases having specificity for murein (e.g., an alanyl amidase). Preferably, the subject enzymes are catalytically disabled to decrease hydrolysis of the instant murein compound bound thereto. Most preferably, the subject enzymes are either chemically altered (e.g., EXAMPLE 3, below) or catalytically disabled mutant enzymes, (e.g., recombinantly derived enzymes such as in EXAMPLE 1, below.) The subject most preferred chemically altered or mutant enzymes retain murein binding ability but lack more than about 70% to about 95%, preferably more than about 85% to about 90%, and most preferably more than about 90%, of their catalytic activity. Representative examples of enzymes that may be so-modified according to the instant invention include those disclosed in TABLE 1, below: e.g., acetyl-muramoyl-D,L-Alanyl amidases, bacterial cell wall penicillin binding proteins, Alanyl D,D- or D,L-endopeptidases, D,D- or D,L-carboxypeptidases, transglycosyl transferases, peptidyl transferases, muramoyl isomerases; muramoyl transglycosylases, murein autolysins, murein hydrolases, β-glucosidases, lysozymes and the like. Preferably, the subject murein-binding polypeptides have amino acid sequences capable of ligand binding (as defined below), wherein the presently most preferred ligand is a murein ligand as isolated from a killed and denatured bacterial or fungal particle following any of the following treatments: namely, (i) fixation with 80% ethanol, (ii) alkaline treatment with 2M NaOH at 60° C. for about 15 minutes to about 30 minutes, (iii) the subject alkaline treatment followed by an optional protease treatment with 0.25% trypsin at 37° C. for minutes, and/or (iv) the subject alkaline treatment followed by an optional periodate-treatment, and/or (v) the subject alkaline treatment followed by a treatment with acetic anhydride (i.e., wherein the subject treatment conditions are in accord with the instant disclosure and illustrations.) Most preferably, the binding interaction between the preferred MBP and a denatured ligand, i.e., according to any of the subject treatments, occurs with high affinity and specificity, and with a binding affinity that is greater than nanomolar (as defined and illustrated further below.) Most preferably, the binding interaction between the most preferred murein binding polypeptides and one of the subject denatured bacterial or fungal ligands, is not inhibited by 100-fold molar excess of a mammalian or plant ligand such as might be present in a food substance.

Representative examples of non-antibody proteins having amino acid sequences and functional properties rendering them suitable candidate murein binding polypeptides include murein biosynthetic and hydrolytic enzymes produced by mammals, insects, bacteria, bacteriophage and fungi, some representative examples of which are set forth in TABLE 1, below.

TABLE 1

Representative Candidate Murein Binding Polypeptides

| Murein Binding Polypeptide | Source | Illustrative Characteristics | Enzyme Activity | Doc. ID No.*/b |
|---|---|---|---|---|
| Autolysins | P. aeruginosa | 26kD membrane vesicle hydrolase | N-Ac-muramoyl-L-Ala amidase | 14 |
| | P. aeruginosa | 15–19kD extracellular hydrolase | amidase | 32 |
| Cell wall metabolic enzymes; e.g., penicillin binding proteins | Bacterial cell walls | membrane proteins binding beta lactam antibiotics; enzymes involved in synthesis of murein: | | |
| | Strep. pneumoniae | penicillin binding protein 2 (PBP2) | transpeptidase | 15 |
| | E. coli | PBP2 | transpeptidase | 25 |
| | E. coli | penicillin binding protein 7/8 (PBP7/8) | Ala DD-endopeptidase | 21 |
| | | PBP3 | transferase | 34 |
| | E. coli | PBP4: 477 amino acids | DD-carboxypeptidase | 29 |
| | E. coli | Membrane lytic transglycosylase, 38 kD | transglycosylase | 19$^r$,22 |
| | several | muramidases | | 19$^r$ |
| | several | chitinases | | 19$^r$ |
| | several | glycosyltransferases | | |
| | Sal. typhi | lipoprot. glyceryl transferase 1gt, 291 aa | glyceryl transferase | 23 |
| | E. coli | 70.5 kD Slt transglycosylase (EC3.2.1-) | transglycosylase | 28 |
| | E. coli | mepA penicillin-insensitive | endopeptidase | 30 |
| | E. coli | EC3.5.1.28 amidase | N-Ac-mur-Ala | 35 |
| | E. coli | gene product mltB, 37 kD protein | amidase | 18 |
| | L. monocytogenes | 60 murein hydrolase murein hydrolase | murein hydrolase | 20 |
| Cell wall recycling enzymes | bacteria with cell walls, esp. species with penicillin resistant serotypes | Enzymes required for induction of penicillin resistance | several | 16$^r$ |
| | | Amp C beta-lactamase | LD-endopeptidase | 26 |
| | | 32 kD norcardicin A sensitive peptidase | LD-carboxypeptidase | 27 |
| bacteriophage | T4 in E. coli | protein T, 18 kD | lysozyme | 17, 33–40 |
| | HB-3 in Strep. | 36 kD hbl gene product murein hydrolase | amidase | 24,36 |
| | Dp-1 in Strep. | endo-N-Ac-muramyl-L-Ala amidase | endopeptidase | 31 32 |
| Commercially available enzymes | Sigma Chem. Co., St. Louis, MO | EC3.2.1.17 carboxymethylated-maleylated reduced | hen lysozyme lysozyme-cat.inactive$^a$ | #L6876 #L1526 #C7809 |
| | | EC3.2.1.21 | | #C6137 |
| | | EC3.5.1.11 | β-glucosidase penicillin amidase | #G4511 #P3319 |

* $^r$= review; kD, kilodalton molecular size, Doc. ID No., see citation list following the examples section;
$^{a.)}$cat. inactive,
$^{b.)}$catalycally inactive It is believe that prior to the instant invention the value of murein binding proteins as diagnostic reagents was not appreciated nor adequately disclosed because many exhibit hydrolytic activity considered incompatible with performance in a diagnostic assay, and/or low binding affinity, and/or apparent lack of specificity for murein compounds (supra). The subject murein binding polypeptides are distinguished from chitinases in the manner set forth in TABLE 2, below.

TABLE 2

| | Ligand | |
|---|---|---|
| Polypeptide | Murein Compound | Chitin Compound |
| MB-Polypeptide | + | + |
| Chitinase | – | + |

+, represents a association constant for binding that is less than about 5 × $10^{-5}$ L/mol;
–, represents a association constant for binding that is greater than about 5 × $10^{-5}$ L/mol, e.g., $10^{-4}$ L/mol.

"Lysozyme" is intended to mean a muramidase capable of catalyzing hydrolysis of a bond in an N-acetyl-muramoly compound. Representative lysozymes include those in IUB class E.C.3.2.1.17, e.g., hen egg white lysozyme, human lysozyme, bacteriophage lysozymes, and other mammalian, animal, plant, fungal, bacterial, protist, viral or bacteriophage lysozymes.

"β-glucosidase" is intended to mean a β-D-glucosidase glucohydrolase. Representative examples of glucosidases may be found in IUB class EC3.2.1 .21.

"Murein binding peptide", abbreviated "MB peptide" is used to refer to a peptide that is composed of about 50 to about 20 amino acids, preferably less than about 20 amino acids, that are arranged in a serial array with each amino acid peptide bonded to its neighboring amino acid in a secondary structure. The constituent amino acids are linked in serial array to form a stable secondary structure that may be further stabilized by chemical modifications designed to create a stable tertiary structure. The subject modified stable MB peptide retains the three dimensional array of amino acids contained in the active site of an enzyme capable of hydrolyzing a murein, but the subject MB peptide while retaining the capacity for binding is catalytically inactive, i.e. according to the definition appearing below. In one representative example, the subject stable secondary structure of the MB peptide consists of a stable alpha helical tertiary structure, and in this case the amino acids utilized for the modification are preferably selected from among the group of amino acids previously termed "helix-formers" by Chou and Fasman (12; at Table 1, page 51), the list of amino acids standing as modified and subject to the limitations discussed in O'Neil and DeGrado (13; at Table 2, page 650), the disclosures of both documents being incorporated herein by reference. As referred to herein, helix formers is intended to mean both weak ("$h_\alpha$") and strong ("$H_\alpha$") helix formers as set forth in Chou and Fasman, supra, and as also conforming with amino acids having $P_\alpha$ values >1.0 at set forth in O'Neil and DeGrado (13; at Table 2, page 650). Representative helix-formers are Ala (A) and Leu (L) which are recognized in the art as strong helix formers. A comparative ranking of helix forming amino acids from Chou and Fasman, supra and O'Neil and DeGrado (13), supra is provided in TABLE 3, below.

TABLE 3

Helix-Forming Amino Acids

| Rank order of Chou and Fasman ($H_\alpha$ and $h_\alpha$) | Rank order of O'Neil and DeGrado ($P_\alpha$ > 1.0) |
| --- | --- |
| E ($H_\alpha$) | A (1.6) |
| A ($H_\alpha$) | L (1.5) |
| L ($H_\alpha$) | F (1.45) |
| H ($h_\alpha$) | M (1.44) |
| M ($h_\alpha$) | W (1.34) |
| Q ($h_\alpha$) | I (1.31) |
| W ($h_\alpha$) | R (1.25) |
| V ($h_\alpha$) | Q (1.22) |
| F ($h_\alpha$) | E (1.18) |
| — | V (1.09) |
| — | K (1.05) |
| — | D (1.03) |

Representative examples of non-helix forming amino acids include Pro (P), Gly (G), Tyr (Y), referred to in the art as helix-breaking amino acids, and these residues are commonly found in helix side-caps adjacent to, but not in, regions of alpha helical structure. Representative regions of helical sequence motifs in murein binding polypeptides include those the substrate binding sites and catalytic sites of muramidases, and transglucosylases including those disclosed previously in Dijkstra et al. (2). The subject MB peptides may be synthesized, e.g. by organic synthesis (below) of a murein binding site motif, or alternatively, molecular mimetics may constructed using branched and straight hydrocarbon (olefin) chains to achieve spacing between organic residues capable of mediating murein binding.

"MBP" is used herein as an interchangeable, and inclusive, as an abbreviation for a murein binding polypeptide or a murein binding peptide.

"Endogenous MBP" is used herein to mean that the subject MBP compound is bound to a murein compound (i.e., an analyte) in a biological sample (defined below) as the subject sample is collected from a source, e.g., air, biological fluid and the like. As such, an endogenous MBP could conceivably constitute a confounding substance in an assay according to the invention.

"Murein binding diagnostic reagents" is intended to mean a reagent suitable for use in a test assay for identifying a eubacteria or a fungi (e.g., a yeast) in a biological sample, e.g. a patient sample or a sample of a sample of food, water or air. The subject murein-binding reagent is provided in a reagent suitable for binding an analyte under conditions maximizing the subject binding interaction while minimizing cross-reactivity with any plant, mammalian, or avian tissue that may be present in the biological sample. The latter specific binding interaction is of course of considerably value when the subject biological sample is collected from a food substance, e.g., plant, animal or avian tissues. The subject murein binding diagnostic reagent commonly contains: (i) an MBP linked to a "signal generating compound", i.e., a "conjugate" (as defined supra); (ii) one or more buffers, additives, excipients and the like for stabilizing and preserving the subject MBP-conjugate during storage; and/or, one or more substances for promoting the binding activity of the subject MBP-conjugate to a murein in a test assay.

"Signal generating compound", abbreviated "SGC", is intended to mean a molecule that can be linked to a MBP (e.g. using a chemical linking method as disclosed further below and is capable of reacting to form a chemical or physical entity (i.e., a reaction product) detectable in an assay according to the instant disclosure. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds, radioisotopes (e.g., $^{125}$I, $^{14}$C, $^{3}$H and the like), enzymes (e.g., below), binding proteins (e.g., biotin, avidin, streptavidin and the like), magnetic particles, chemically reactive compounds (e.g., colored stains), labeled-oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative SGC useful in an MBP-conjugate include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); IUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); IUB Class 4 (e.g., lyases); IUB Class 5 especially 5.3 and 5.4 (e.g., phosphoglucose isomerase, trios phosphatase isomerase, phosphoglucose mutase and the like.) The subject signal generating enzymes may be coupled to a non-antibody MBP, e.g., lysozyme, or to a second binding partner used in combination with a MBP, e.g., a different MBP (i.e., MBP #2; as disclosed further, below.) The subject SGC share the common property of allowing detection and/or quantification of a murein analyte in a test sample. Preferably, the subject signal generating compounds are detectable using a visual method, a spectrophotometric method, an electrical method (e.g., a change in conductance, impedance, resistance and the like), or, a fluorescent detection method.

"Solid phase", as used herein, is intended to mean a surface to which one or more reactants may be attached electrostatically, hydrophobically, or covalently. Representative solid phases include e.g.: nylon 6; nylon 66; polystyrene; latex beads; magnetic beads; glass beads; polyethylene; polypropylene; polybutylene; butadiene-styrene copolymers; silastic rubber; polyesters; polyamides; cellulose and derivatives; acrylates; methacrylates; polyvinyl; vinyl chloride; polyvinyl chloride; polyvinyl fluoride; copolymers of polystyrene; silica gel; silica wafers glass; agarose; dextrans; liposomes; insoluble protein metals; and, nitrocellulose. Representative solid phases include those formed as beads, tubes, strips, disks, filter papers, plates and the like. Filters may serve to capture analyte e.g. as a filtrate, or act by entrapment, or act by covalently-binding MBP onto the filter (e.g., EXAMPLE 3, below). According to certain embodiments of the invention, a solid phase capture reagent for distribution to a user may consist of a solid phase (supra) coated with a "capture reagent" (below), and packaged (e.g., under a nitrogen atmosphere) to preserve and/or maximize binding of the capture reagent to a murein analyte in a biological sample.

"Capture reagent" is intended to mean an immobilized murein binding polypeptide (or peptide) capable of binding a murein compound or murein-like compound. The subject capture reagent may consist of a solution or MBP modified so as to promote its binding to a solid phase, or as an MBP already immobilized on a solid phase, e.g., immobilized by attaching the MBP to a solid phase (supra) through electrostatic forces, van Der Waals forces, hydrophobic forces, covalent chemical bonds, and the like (as disclosed further below.) Representative examples of MBP-capture reagents are disclosed (EXAMPLE 1, below) and include mobile solid phase MBP-capture reagents such as MBP immobilized on movable latex beads e.g. in a latex bead dipstick assay.

"Detect reagent" is intended to mean a conjugate containing an SGC linked to a murein binding polypeptide (or MB peptide). Representative examples of the instant detect reagents include SGC-MBP; complexes of antibiotic compounds with MBP, i.e., at a site distinct from the murein binding site, thereby forming a sandwich; antibodies (Ab) capable of specifically binding to an MBP and conjugated with a SGC, e.g., SGC-Ab, and the like. The subject detect reagents include mobile solid-phase detect reagents such as movable latex beads in latex bead dipstick assays.

"Biological sample" is intended to mean a sample obtained from a living (or dead) organism, e.g., a mammal, fish, bird, reptile, marsupial and the like. Biological samples include tissue fluids, tissue sections, biological materials carried in the air or in water (e.g., bacteria, fungi, spores and the like) and collectable therefrom e.g., by filtration, centrifugation, and the like. Representative biological fluids include, e.g. urine, blood, plasma, serum, cerebrospinal fluid, semen, lung lavage fluid, feces, sputum, mucus, water carrying biological materials and the like. Representative biological samples also include foodstuffs, e.g., samples of meats, processed foods, fishes, cereal grains and the like. Biological samples also include contaminated solutions (e.g., contact lens solution, irrigation solutions, intravenous solutions and the like), contaminated human healthcare products (e.g., shampoos, toiletries, contact lenses, and the like), swab samples from food preparation facilities (e.g., restaurants, slaughter-houses, cold storage facilities, supermarket packaging and the like). Biological samples may also include in-situ tissues and bodily fluids (i.e., samples not collected for testing), for example, the instant ISBES methods may be useful in detecting the presence or severity or bacterial infection in eyes (e.g., using MB-polypeptide-latex eye drops); or, the presence or extent of contamination of carcasses e.g. in a packing plant. Thus, embodiments of the invention provide ISBES methods useful in testing a variety of different types of biological samples for the presence or amount of a bacterial or fungal contamination or infection.

"Ligand" as used herein refers to a murein compound capable of binding to an MBP binding site. Representative examples of ligands include murein-containing complex cell wall compounds (supra) as found in a variety of gram positive and gram negative bacteria and murein-like compounds found in fungi (defined supra.) The subject ligand is capable of filling a three-dimensional space in binding site of a MBP so that electrostatic repulsive forces are minimized, electrostatic attractive forces are maximized, and hydrophobic and hydrogen bonding forces are maximized. Ligands bind to MBP in a specific and saturable manner, and binding affinities may be measured according to ligand binding assays known to those skilled in the art, e.g. as disclosed further below.

"Ligand binding" between a murein binding polypeptide (or MB peptide) and a murein-, or murein-like, ligand is specific and saturable, and may e.g. be determined by incubating labeled ligand (e.g., radiolabeled or biotin-labeled) at a concentration of about 0.1 fM to 10 mM (e.g., at room temperature, 37° C., or 4° C.) with an aliquot of the MBP at a concentration of about $10^{-4}$ to $10^{-12}$ M. At lower binding affinities (e.g., $10^{-3}$ to $10^{-5}$), "bound" ligand is separated from "free", (e.g., by centrifugation, filtration, column chromatography and the like) and the amount of labeled murein ligand is determined (e.g., by quantifying radioactivity or reacting the sample with enzymatically-labeled avidin, washing to remove unbound avidin, and then adding substrate to visualize the enzyme-bound-avidin-biotin receptor complex). At binding affinities greater than $10^{-10}$ it may be difficult to measure binding by solid phase techniques since binding becomes relative irreversible, but alternative measurement methods such as equilibrium dialysis, or sucrose density gradient ultracentrifugation, i.e., using CsCl banded and sized cell wall fragments. Data obtained in these binding assays may be used to construct a Scatchard binding curve allowing determination of an association constant (Ka) that reflects the relative binding affinity of a MBP for a ligand. Preferably, the subject MBP have a binding affinity for diose, triose and tetraose bacterial and fungal cell wall compounds (e.g., chitatriose, (NAc-glucosamine)$_3$, and the like) that is in the range of about $10^{-3}$ L/mol to about $10^{-5}$ L/mol; and, the subject compounds are effective to bind the subject murein or murein-like compound with a association constant ($K_a$) in the range of about $5 \times 10^{-5}$ L/mol to about $10^{-9}$ L/mol, preferably $5 \times 10^{-7}$ L/mol to $10^{-9}$ L/mol, and most preferably greater than $10^{-9}$ L/mol. The binding affinity of radiolabeled catalytically disable lysozyme to bacterial mureins covalently bound to CNBr-Sepharose-4B (Pharmacia) was greater than about $10^{-10}$ L/mol, i.e., the radiolabled MBP was not easily removed from the resin.

"Catalytically inactive" murein binding polypeptide (or peptide) is intended to mean that the subject MBP is capable of binding a murein compound or a murein-like compound and it either completely lacks the ability to catalyze cleavage of any bond in the subject murein compound, or it has only about 5% to about 30% of the activity of a corresponding wild-type enzyme, preferably only about 10% to about 15% of wild-type enzyme activity, and most preferably less than about 10% of wild-type enzyme activity. Most preferably, the subject catalytically inactive MBP exhibits a catalytic turnover rate of less than about 0.5 mmol to about 3 mmole of the subject murein compound per mole enzyme per minute, preferably less than about 1 mmol to about 1.5 mmol substrate per mole enzyme, and most preferably less than about 1 mmol substrate cleaved per mol MB polypeptide per minute. Representative examples of catalytically inactive murein binding polypeptides are disclosed in EXAMPLE 1, below, and include at least recombinant, mutant, chemically modified, and chemically inactivated polypeptides that have murein binding capability but are catalytically inactive (as defined supra.) Examples include enzymes having catalytic active sites with one or more amino acid residues modified, inactivated, swapped/exchanged, mutated, chemically modified, derivatized, cross-linked and the like. Preferably, the subject catalytic site amino acid residues, so modified, are those which are capable in a wild-type enzyme of participating in a catalytic exchange mechanism. Illustrative assays for determining catalytic activity are disclosed below (e.g., EXAMPLE 1.) In alternative embodiments, ISBES methods (supra) are provided for producing killed and denatured bacteria and fungal particles having murein ligands that may constitute good ligands but poor substrates. The subject ligands are properly reactive with certain wild-type enzymes, i.e., lysozyme and chitinase, so that these wild-type enzymes may be used according to the methods of the ISBES methods described supra and illustrated in the Examples section, below.

"Non-interfering amino acid", as used herein, is intended to mean any amino acid that when introduced into an MBP does not interfere with binding of a murein ligand, but is effective to render the subject enzyme catalytically inactive. For example, non-interfering amino acids may be useful to alter the spacing between adjacent or distant chemical residues, or to change the electrostatic charge distribution, or hydrophobic properties of an enzyme catalytic active site. Non-interfering amino acids may also be useful for terminal extension (N-terminal or C-terminal) of MB peptides to stabilize the subject peptides. Disclosed below are methods for altering enzyme active sites (e.g., by site directed mutagenesis, chemical modification, and the like; EXAMPLES 1 and 3) and to render them catalytically inactive and suitable for use according to the instant invention.

"MB polypeptide fragments" is used to mean those portions of an MBP that are smaller in size than a wild-type MBP, i.e., isolated from a natural source (supra). Fragments may be prepared from a substantially purified MBP (i.e., preferably greater than 90%, and most preferably greater than 95% pure, by SDS-PAGE) by proteolytic degradation (e.g., with trypsin, chymotrypsin, pronase, papain, subtilisin, and the like), or alternatively, by treating the subject polypeptide with a chemical hydrolyzing peptide bonds (e.g., cyanogen bromide.) In the latter case, the fragments of the MBP are also preferably purified substantially before use in the instant diagnostic reagents and assays, e.g., by reverse-phase HPLC or ligand-affinity chromatography, e.g. on a resin containing one or more covalently bound murein compounds. Alternatively, fragments of an MBP may be prepared by expressing e.g. in a recombinant host cell, a portion of a nucleotide sequence of a wild type (or mutant) genomic or cDNA clone capable of expressing the subject MBP. Host cells are e.g. produced by introducing a nucleotide sequence, e.g., DNA or RNA introduced by transfection, transduction or infection using e.g. in an expression plasmid (or vector). Recombinant host cells include bacterial cells, insect cells, yeast cells and mammalian cells. The subject host cell manufactures the subject MBP fragment which may be purified prior to use. Following purification, the subject MBP fragment may be tested to confirm murein binding activity.

"Specificity", when used in the context of an assay according to an embodiment of the invention, is intended to mean that the subject assay, as performed according to the steps of the invention, is capable of properly identifying an "indicated" percentage of samples from within a panel of biological samples (e.g., a panel of 100 samples). The subject panel of samples all contain one or more murein analytes (e.g., positive control samples contaminated with bacteria or fungi.) Preferably the subject "indicated" specificity is greater than 85%, (e.g., the assay is capable of indicating that more than 85 of the 100 samples contain one or more murein analyte), and most preferably, the subject assay has an indicated specificity that is greater than 90%.

"Sensitivity", when used in the context of an assay according to an embodiment of the invention, is intended to mean that the subject assay, as performed according to the steps of the invention, is capable of identifying at an "indicated" percentage those samples which contain a murein analyte from within a panel of samples containing both positive controls (supra) and negative controls (i.e., lacking murein analyte.) Preferably the subject "indicated" sensitivity is greater than 85% and most preferably greater than 90%.

"Background", when used in the context of an assay according to an embodiment of the invention, is intended to mean the uncertainty in a test result, (sometime expressed as a percentage of false-positive or false-negative test results or by a measurement of a degree of confidence in a test result), occasioned by substances which may interfere with the proper performance of the assay when they are present in the assay. Representative examples of substances which may so interfere (i.e., interfering substances, confounding substances, and the like) in the assay include materials present in biological samples such as di- and trisaccharide cell wall components of bacteria and fungi, endogenous murein binding polypeptides (defined supra), inhibitors or substrates for signal generating compounds (e.g., enzyme inhibitors, free radical reactive compounds, endogenous peroxides and the like.)

MBP suitable for use in the instant invention may also be prepared by chemical modification of an enzyme (e.g., TABLE 1). For example, a subject enzyme may be treated with a chemical selected for its ability to render the subject enzyme catalytically inactive while preserving murein binding activity. Esterification and methylation of lysozyme are representative examples of a chemical treatments that destroy catalytic activity (according to the invention, supra) while preserving murein binding activity. Another representative example is chemical cross-linking to form enzyme-dimers wherein the tertiary structure of enzyme is rendered rigid and/or entry and exit of substrates from a catalytic site is obstructed. Representative examples of enzyme active site inhibitors that may be useful in preparing MBP include Allosamidin (7) and the like.

"Substantially purified" is used herein to refer to a preparation that contains a MB polypeptide, a MB polypeptide fragment, or a MB peptide that is enriched greater than about 10-fold to about 25-fold, preferably greater than about 26-fold to about 50-fold and most preferably greater than about 100-fold from the levels present in a source material. The subject preparation also preferably contains less than about 10% impurities, and most preferably less than about 5% impurities detectable e.g. by either SDS-PAGE or reverse-phase HPLC.

An MB peptide may be synthesized by any of a number of automated techniques that are now commonly available. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the peptides, i.e., by racemization or by hydrolysis of the formed peptide bonds. Amino acids with carboxyl- groups (e.g., Asp, Glu) or hydroxyl- groups (e.g., Ser, homoserine, and tyrosine) also require blocking prior to condensation. A wide variety of procedures exist for synthesis of MB peptides, solid-phase synthesis usually being preferred. In this procedure an amino acid is bound to a resin particle, and the MB peptide generated in a stepwise manner by successive additions of protected amino acids to the growing chain. Modifications of the technique described by Merrifield are commonly used (Merrifield, R. B., J. Am. Chem. Soc., 96: 2989–2993, 1964.) In an exemplary automated solid-phase method, peptides are synthesized by loading the carboxy-terminal amino acid onto an organic linker (e.g., PAM, 4-oxymethyl phenylacetamidomethyl) covalently attached to an insoluble polystyrene resin that is cross-linked with divinyl benzene. Blocking with t-Boc is used to protect the terminal amine, and O-benzyl groups are used to block hydroxyl- and carboxyl-groups. Synthesis is preferably accomplished in an automated peptide synthesizer (Applied Biosystems, Foster City, Calif.). Following synthesis, the product may be removed from the resin and blocking groups removed using hydrofluoric acid or trifluoromethyl sulfonic acid according to established methods (Bergot, B. J. and S. N. McCurdy, Applied Biosystems Bulletin, 1987.) A routine synthesis can produce 0.5 mmole of MB peptide-resin. Yield following cleavage and purification is approximately 60 to 70%. Purification of the product MB peptide is accomplished for example by (i) crystallizing the MB peptide from an organic solvent such as methyl-butyl ether, followed by dissolving in distilled water, and dialysis (if greater than about 500 molecular weight); or, by (ii) reverse HPLC (e.g., using a C18 column with 0.1% trifluoroacetic acid and acetonitrile as solvents) if less than 500 molecular weight. Purified MB peptide is commonly lyophilized and stored in a dry state until use.

Knowledge of the amino acid sequence of a MB polypeptide (or MB peptide) (i.e., the sequence of amino acids and spatial distribution of amino acids in a sequence motif involved in murein binding permits construction of recombinant host cell expression systems (supra) wherein a cDNA (or genomic DNA) capable of encoding a wild type parental MBP (e.g., an enzyme) is modified (e.g., chemically or by site-directed mutagenesis) to produce a nucleotide sequence capable of encoding a recombinant catalytically inactive MBP. A representative example of the subject modification of a cDNA is disclosed in EXAMPLE 1, below. For site-directed mutagenesis complementary oligonucleotides may be synthesized, or restriction fragments may be produced and chemically modified, in either case, the methods are available in the art. Incorporation of modified cDNAs (or gDNAs) into bacteria, yeast, and insect plasmid DNAs, as well as into mammalian cell viral vectors (e.g., retroviral vectors) may also be accomplished using techniques available in the art. Host cell expression systems that may be useful for producing MBP compounds include at least prokaryotic, eukaryotic, yeast, and insect cells. In one presently preferred embodiment, the cellular expression system contains a tandem repeat from a sequence capable of coding for the subject MBP and 1 mole of the expressed protein product of the coding sequence is cleavable by cyanogen to yield about 2 mole of the subject MBP protein.

The present invention also provides that MBP may also be produced by chemical means, e.g., by derivatizing and covalently modifying a wild-type MBP (e.g., an enzyme selected from Table 1), thereby rendering the subject enzyme catalytically inactive and suitable for use in an MBP diagnostic reagent. For example, modification of an MBP may include: (a) covalently modification, e.g. by adenylation, methylation, esterification, acylation, acetylation, phosphorylation, uridylation, fatty-acylation, glycosylation, and the like; (b) stereoisomerization, e.g., replacing a D-amino acid with an L-stereoisomer e.g. during solid phase synthesis; (c) derivatization, wherein one amino acid is substituted for another of like properties by a series of chemical modifications or during solid phase synthesis, i.e., substitution of one neutral polar amino acid for another neutral polar amino acid (e.g., G, A, V, I, L, F, P, or M); or, substitution of a neutral nonpolar amino acid for another neutral nonpolar amino acid (e.g., S, T, Y, W, N, Q, or C); or, substitution of an acidic amino acid for another acid (e.g., D or E), or a basic amino acid for another (e.g., K, R, or H); or, (d) chemically modification, e.g., converting an active site carboxyl group to a carbonyl or aldehyde, or converting an amine to an amide, or introducing a side chain at an active site residue e.g. Sar or gamma-amino butyric acid (GABA); or, (e) chemical coupling, e.g., covalently coupling one active site residue to another residue using e.g. a heterobifunctional cross-linking reagent (Pierce Chemical Co.); (f) or, chemical coupling to accomplish an N- or C-terminal extension (e.g. for an MB peptide); or, (g) replacing one amino acid with another of slightly different properties e.g., to change hydrophobicity of a peptide. In one presently preferred embodiment the MBP lysozyme was catalytically inactivated by methylation or esterification.

Embodiments of the invention also provide increased binding affinity through use of multimeric MBP compounds and chimeric MBP compounds. Multimeric MBP compounds containing multiple copies of the same MBP may be synthesized, or produced through genetic recombination, or chemically coupled the one to the other. Chimeric MBP compounds containing multiple copies of two or more different MBP may combine advantageous properties of two different MBP molecules into a single molecule (e.g., combining MBPs having two different anomeric or stereo specificities; or, combining an MBP having specificity for a murein oligopeptide side chain with an MBP having specificity for sugar residues in a glycosyl chain); or, to increase the binding affinity of the subject MB-polypeptides to a ligand through cooperative binding interaction between the respective different respective binding sites within the resultant chimeric molecule. In one representative example, lysozyme is coupled to a chitinase to increase MBP binding affinity and broaden ligand binding specificity, as well as, to improve biochemical properties such as hydrophobicity and/or thermal stability. In another representative example, a bifunctional murein binding polypeptide consists of a portion of a lysozyme covalently coupled to a portion of a transglycosylase. In yet another representative example, a bifunctional murein binding polypeptide consists of an enzyme (e.g., lysozyme) coupled to a murein binding lectin (e.g., neolectin.) In another representative example a bifunctional murein binding polypeptide consists of an enzyme (e.g., an N-Acetyl-gluanase) coupled to a murein binding antibiotic (e.g., vancomycin.)

Embodiments of the invention provide diagnostic reagents useful in assay formats for identifying bacteria and fungi and their cell wall products in a variety of different types of biological samples. Representative assay formats useful for detecting mureins include enzyme-linked murein-binding solid-phase absorbent assays (ELMBSA), radiolabeled murein-binding assays (RMBA), fluorescence murein-binding assays (FMBA), time-resolved MB fluorescence assays (TRMBF), as well as, sandwich- and enzyme-cascade assay formats. Illustrative methods, as may be adaptable from the immunoassay art for use in the subject murein-binding assays include: homogeneous assay formats; heterogeneous assay formats; competitive assay formats; non-competitive assay formats, enzyme-linked solid phase assay formats, fluorescence assay formats, time resolved fluorescence assay formats, bioluminescent assay formats, and the like, examples of which are provided in the Appendix following the Examples section, below. The instant murein-binding assay formats differ from the former assays in their use of a non-antibody MBP, and the sample pretreatment and assay conditions necessary and effective to detect a murein compound (or murein-like compound) in a biological sample. Illustrative different MB assay formats are summarized in TABLE 4, below.

TABLE 4

Representative Murein Binding Assay Formats*

| Solid Phase | Capture Reagent | Separation of Bound Murein from Free | Detect Reagent First Partner | Detect Reagent Second Partner |
|---|---|---|---|---|
| Whole bacteria in test sample, filter or c'fuge to collect | None | filter, centrifuge and/or wash | MBP-SGC | None |
| | None | filter, centrifuge and/or wash | MBP#1 | BP#1 |
| | None | filter, centrifuge and/or wash | None | BP#1 |
| Plastic: polystyrene, PVDF, nylon 6.6, plates, filters, beads | MBP#1 | filter, centrifuge and/or wash | MBP#2-SGC | None |
| | MBP#2 | filter, centrifuge and/or wash | MBP#1 | BP#1-SGC |
| | MBP#1 | filter, centrifuge and/or wash | BP#1-SGC | None |
| Glass: amidated | MBP#1 | filter, centrifuge and/or wash | MBP#3 | BP#3-SGC |
| | MBP#3 | filter, centrifuge and/or wash | BP#3 | None |
| Magnetic particles | MBP#1 | filter, centrifuge, 1xg settle, pass over magnet, and/or wash | MBP-SGC | None |
| Dipstick | MBP#1 region on dipstick | occurs during movement of mobile phase along dipstick | MBP-SGC | None |
| Dipstick | MBP#1 region on dipstick | occurs during movement of mobile phase along dipstick | MBP-SGC bound to latex beads mobile on dipstick | None |
| Dipstick | MBP#1-SGC on dipstick (e.g. SGC = fluorophore); MBP#2-latex bead bound in mobile phase) | occurs during movement of mobile phase along dipstick | None (e.g., UV fluorescence quench by binding of bead-MBP-analyte to MBP#1-SGC) | None |

*SGC, signal generating compound; MBP, murein binding polypeptide; First partner, first binding partner; Second partner, second binding partner; MBP#1, specificity #1 of binding to a murein compound (e.g., specificity for β-1,4 linked glycosyl compounds); BP#1, specificity for binding to MBP#1 (e.g., an antibiotic binding an MBP such as vancomycin); MBP#2, specificity #2 of binding to a murein compound(e.g., specificity for N-acetyl glucosamine); BP#2, specificity of binding to MBP#2; MBP#3, specificity #3 of binding to a murein compound (e.g., specificity for alanyl containing peptides); BP#3, specificity for binding MBP#3 (e.g., monoclonal antibody to MBP#3).

The instant diagnostic assay formats and diagnostic reagents include those useful for detecting endogenous and exogenous murein binding polypeptides at they are found in situ after binding to murein compounds in the cell walls of eubacteria and fungi. "Endogenous murein binding polypeptides" is intended to mean MBP that are synthesized by bacteria and fungi and become incorporated into the cell wall of these organisms. Representative examples of endogenous murein binding polypeptides include bacterial peptidyl transferases which covalently crosslink peptidoglycan chains, and themselves become covalently bound in the bacterial cell wall. "Exogenous MBP" is intended to mean MBP that are added to the bacteria or fungi; where they become bound to murein compounds in the cell wall; then subsequently, they are detectable through use of an antibiotic-SGC conjugate that specifically binds to the subject MBP. Embodiments of the invention provide reagents and methods for detecting murein binding polypeptides in situ, i.e., as they are bound in the cell walls of bacteria and fungi. Preferably, a diagnostic reagent for identifying a murein binding polypeptide in situ includes an antibiotic compound chemically conjugated to a signal generating compound, i.e., an antibiotic-SGC. An illustrative example is provided in the Examples section below, wherein ampicillin was chemically bonded through its free amino group to NHS-fluorescein and is useful in detect endogenous MBP in bacterial cells, i.e., endogenous peptidyl transferases.

Representative antibiotic compounds that may be conjugated to a signal generating compound for detecting an endogenous or exogenous murein binding protein in situ in a bacterial or fungal cell wall, include antibiotic selected from among the groups of penicillins, ampicillins, amoxycillins, vancomycins, streptomycins, erythromycins, bacitracins, tetracyclines, polymyxins, novobiocins, colistins, kanamycins, neomycins, ristocetins, gramicidins, spiramycins, cephalosporins, capreomycins, rifamycins and gentamycins.

The instant murein-binding assay methods include those having a step effective to simultaneously accomplish binding and signal generation as an analyte binds to an MBP, i.e., a "simultaneous" or "homogeneous" assay format. The instant methods also include "heterogeneous" murein-binding assay formats, including one or more steps for separating a "bound" from a free analyte and then generating a signal. The instant methods also include those having a step in which analyte is added to compete with the binding of a labeled ligand to an MBP, i.e., a competitive binding (or indirect) assay format, or alternatively, in which binding of an analyte to a MBP is detected by adding a second MBP having signal generating compound, i.e., a non-competitive (or direct) assay format. Illustrative methods for separating "bound" analyte, ligand or MBP from "free" include filtration, and column separation, magnetic separation, as well as attaching one or more of the reactants to a solid phase. Illustrative murein-binding assay methods for detecting a signal generating compound commonly include: using an enzyme as a SGC that converts a substrate to a visually or spectrophotometrically identifiable product), or alternatively, exciting a fluorescent SGC coupled to an MBP so that a detectable signal is emitted, e.g. at a different wavelength, e.g. fluorimetric analysis.

Commonly, coating polystyrene (e.g., 96-well Dynatech-Immulon II, Nunc, or similar plates) with a murein binding polypeptide at a concentration of about 1 mg/ml in a carbonate buffer at pH 8 for about 16 hours results in binding of about 20 to about 150 μg/well to the solid phase.

Embodiments of the invention provide flow cytometric assays using an MBP-SGC conjugate as a bacterial or fungal identification reagent. In one presently preferred embodiment, the cytometric assay is a fluorimetric assay and the SGC is a fluorophore. The instant flow cytometric assays may be conducted with or without size discrimination (e.g., based on light scatter measurements); with or without a second dye indicator (e.g., propitium iodide, FITC, F-NHS, RITC, and the like); and, with or without quantification (e.g., counting the number of particles positive in the assay for binding of the subject murein binding polypeptide (peptide) conjugates. Additionally, size gating may be adjusted to discriminate between bacterial and/or fungal analytes in a biological sample, and/or to reduce background. Particle counting may be used to quantify the number analyte particles binding an MBP-conjugate. Quantification of the number of analyte particles in a biological sample may be used to determine the severity of an infection in a host in need thereof, e.g., a human patient or an animal.

Embodiments of the invention include, murein-binding solid-phase assay formats having at least the following two steps: namely, In a first step, a murein analyte present in a biological sample is 'captured', by binding to a MBP compound that is attached electrostatically (or covalently) to a solid phase; and, In the second step, bound bacterial murein analyte is detected by reacting it with a MBP "detect reagent" having a signal generating compound.

Other steps in the instant murein-binding diagnostic assay formats may include one or more steps for pretreating a fresh, frozen or stored biological sample (e.g., stored at 4° C., –20° C., –70° C. and the like). The instant pretreatment step may involve adding (i.e., before step 1, above) an acid, a base, a mucosidase, a detergent (e.g., TWEEN-20), and/or a protease or DNAase, and the like. The preferred pretreatment step decreases the viscosity in a sample; or, to increases the solubility of the sample (e.g. a lung lavage, sputum or urine sample); or, to denature endogenous lysozymes or chitinases that can constitute confounding or interfering substances in an assay; or, to inactivate bacterial and fungal cell wall compounds that can constitute background interfering substances in an assay; or, to increase exposure and accessibility of a murein- or murein-like compound in a biological sample for binding by an MBP. A preferred step in the ISBES assay methods described supra, is effective to accomplish the subject decrease in viscosity and increase in viscosity, in addition to the other aspects described supra. In one preferred embodiment, fungal murein-like analytes in a urine sample are collected by centrifugation or ultrafiltration; the urine sediment is washed and then treated with a chemical base solution at about 25° C. to about 100 C, preferably about 25° to about 65° C., and most preferably about 55° C. to about 65° C. The subject treatment is preferably conducted for about 2 minutes to about 20 minutes, preferably about 10 minutes to about 30 minutes, and most preferably about 20 minutes to about 30 minutes. Preferably, the shorter incubation times, i.e., about 2 minutes to about 9 minutes, and/or lower temperatures, i.e., less than 45° C., are conducted with about 2M to about 5 M of a strong base solution, e.g. sodium hydroxide, potassium hydroxide, ammonium hydroxide, barium hydroxide, calcium hydroxide, potassium carbonate, sodium carbonate, potassium acetate and sodium barbital and like. Preferably, the pH of the chemical base solution is greater than about pH 9 and most preferably greater than about pH 10. Preferably, intermediate incubation times, i.e., about 10 minutes to about 14 minutes, are conducted with about 0.2 M to about 3.5 M concentrations of a strong base, e.g., KOH, NaOH and the like. Preferably, the longer incubation times, i.e., about 15 minutes to about 30 minutes, are conducted with about 0.2M to about 2M concentrations of a strong base, e.g., KOH, NaOH and the like. In all cases, the subject treatment is capable of killing bacteria and fungi, hydrolyzing a test bacterial or fungal polypeptide (supra), and producing killed and denatured bacterial and/or fungal particles containing ligands reactive with the instant MBP compounds. Following alkaline treatment(s), a subject urine sediment sample is then optionally washed, neutralized (e.g., using an HCl solution), and/or optionally treated with one or more of a protease, a glycosidase, a sialidase and/or a periodate. Most preferably, following alkaline treatment and/or any optional treatment, the subject urine sediment sample is treated with an acetylation solution capable of effecting N-acetylation of sugar residues in the sample. Representative N-acetylation solutions so capable, include solutions of pure acetic anhydride at final concentrations of about 0.8% (v/v) to about 5% (v/v), preferably about 1% (v/v) to about 4% (v/v), and most preferably about 2% (v/v) to about 5% (v/v); also, solutions of acetyl chloride at about 2M to about 5M; and solutions of acetylation reagents capable of achieving like effects without destroying the integrity of a killed and denatured yeast particle. The combined subject treatments were effective to produce single particle suspensions of killed and denatured fungal cells suitable for use with lysozyme-fluorophore conjugates wherein the presence and number of the particles were determined by counting in a flourescence flow cytometer. Other features of the instant murein-binding assay formats are disclosed below.

"Uniform assay format" is intended to mean that the molecule capable of capturing (e.g., MBP #1) a bacterial murein, e.g., on a solid phase, and the molecule capable of detecting the captured bacterial murein (i.e., MBP #2) are the same non-antibody MBP, e.g., MBP #1 and MBP #2 (TABLE 4, above, are both lysozyme.) It is intended within this definition that different forms of the non-antibody MBP (as defined by MBP #1, MBP #2, and MBP #3, supra) may be used for the capture reagent and the detect reagent, i.e., lysozyme polypeptide as MBP #1 and a lysozyme fragment-SGC as MBP #2.

"Mixed assay format" is intended to mean that in a first step of the assay the molecule capable of capturing a murein compound is different than the molecule capable of detecting the captured murein in a second step, e.g., non-antibody MBP in the first step, (e.g., MBP #1–3, TABLE 4) and a lectin- or antibiotic-MBP (i.e., capable of binding the respective MBP) in the second step (e.g., BP #1–3, TABLE 4.)

In other alternative embodiments the invention provides mixed assay formats in which a MBP is used as a 'capture' (e.g., MBP #3; TABLE 4) and an antibody-conjugate specific for the MBP or for the captured murein compound is used as a 'detect' (e.g., BP #3, TABLE 4.) The capture reagent may alternatively consist of an antibody and the detect reagent an MBP-SGC conjugate. Polyclonal and monoclonal antibody reagents specific for a murein, or MBP, may be prepared by standard methods, including (if necessary) conjugating the subject murein to a carrier (e.g., KLH or BSA) to increase its immunogenicity.

In one presently most preferably mixed assay format embodiment antibodies are specifically reactive with an MBP, rather than with a murein compound. Monoclonal antibodies to bacterial cell wall compounds disclosed by Shockman in U.S. Pat. No. 4,596,769, (resulting from immunization of mice with bacteria and bacterial cell wall fractions; column 4, lines 39–42), were tested and not found useful in the instant assays because of high background binding to non-bacterial and fungal materials in biological samples. In the latter case, background nonspecific binding may perhaps result from cross-reactivity (i.e., at the antigen binding site); or, binding of compounds to the Fc portion of the antibody (e.g., the C1q complement collagen-motif binding site); or, nonspecific binding to immunoglobulins involving e.g. electrostatic or hydrophobic forces.

In certain other embodiments, the invention provides diagnostic reagents containing MBP that are detect reagents. The instant detect reagents contain one or more signal generating compounds conjugated to an MBP. Representative methods for covalently linking SGC to MBP include those using hetero-bifunctional cross-linking reagents that are reactive with carbonyl, aldehyde, carboxyl, amino, disulfide and thiol groups of amino acids, e.g., carbodiimide, N-hydroxy succinimide, N-succinimidyl-3-(2-pyridyldithio) propionate (SPDP), maleimide, succinimidyl-pyridylthioproprionate, m-maleimidobenzoyl N-hydroxysuccinimide ester, succinimidyl pyridylthiopropionate, and the like. Methods for linking SGC fluorophores to MBP include, e.g., encouraging electrostatic interactions of the subject MBP with the fluorophore by placing the MBP in a buffer having a pH below its isoelectric point (e.g., pH 2.5–3). An illustrative method for linking a fluorophore to MBP is disclosed (EXAMPLE 2, below.). Methods suitable for linking phycobiliproteins to MBP are disclosed in Stryer et al. (U.S. Pat. No. 5,055,556).

The instant MBP-SGC conjugates (supra) are prepared for commercial distribution as detect reagents, preferably by solubilizing them in one or more buffer solutions and then dispensing them into reagent bottles, packages and the like; or, alternatively, by lyophilizing them and dispensing them as powders into reagent packages. The subject buffer solutions may include additives (e.g., stabilizers), emulsifiers (e.g., detergents), and the like for preserving the activity of the instant MBP-conjugate during storage; or, for promoting the binding activity of the instant MBP for a murein ligand or analyte in a murein-binding assay of the invention. Examples of agents that may be used to promote the subject binding interactions include additives that decrease total fluid volume in an assay (e.g., polyethylene glycol, sucrose and the like); and, agents that promote interactions by provide an electrostatic surface in solution (e.g., dextran, polystyrene beads, polyacrylate beads, and the like.).

Embodiments of the invention provide assay formats including competitive and non-competitive, direct and indirect, quantitative and non-quantitative assays including ELMBSA, RMBA, FMBA, TRMBF, and cascade assay formats (supra). "Cascade assay formats" is intended to mean detecting a murein (or murein-like) compound through a process: wherein, a first signal generating compound (i.e., SGC #1) produces a product that can be utilized by a second SGC #2 to produce a product which e.g. can be utilized by a third SGC #3. The subject cascade of products from SGC #1–3 results in amplification which results in a greater overall signal that could be achieved by any single SGC.

As a first representative example of a murein binding assay according to the instant invention, an ELMBSA is conducted using MBP-SGC as both a 'detect reagent' (supra) and MBP in a "capture reagent". In the subject MBP-SGC the SGC is an enzyme. Steps in a ELMBSA include: (i) coating the surface of an assay plate, e.g., a 96 well Immulon-II™ microtiter plate (Dynatech, Inc.), with the MBP-capture reagent (supra); (ii) adding an aliquot of a biological sample for a period of time sufficient to accomplish binding between an analyte in the biological sample and the MBP 'capture reagent', i.e., about 2 to about 60 minutes, preferably about 2 to about 30 minutes, and most preferably about 2 to about 15 minutes; (iii) washing to remove unbound materials in the biological sample from the wells in the microtiter plate; (vi) adding the MBP-SGC 'detect reagent', i.e., MBP-enzyme conjugate and incubating for a time sufficient to allow for binding of the MBP-SGC to any analyte bound to the capture reagent; (v) washing to remove unbound MBP-SGC detect reagent; (vi) adding a substrate for the enzyme signal generating compound; and, then (vii) incubating with the substrate for a period of time sufficient to convert the substrate to a product that is detectable in the assay, e.g., spectrophotometrically or visually.

In a second representative example of a murein-binding assay according to the instant invention, a quantitative simultaneous competitive ELMBSA includes the steps of: (i) coating a solid phase with one or more murein compounds (e.g. bacterial or fungal cell wall fragments); (ii) in a separate container mixing a predetermined amount of an MBP-SGC conjugate with an aliquot of a biological sample for a time sufficient to establish a binding interaction between the MBP-SGC (i.e., an enzyme SGC) and any analyte that may be present in the sample; (iii) adding the analyte/MBP-SGC mixture to the murein-coated solid phase; (iv) determining the amount of MBP-SGC conjugate available for binding to the solid-phase murein coating by separating the analyte/MBP-SGC mixture from the solid phase, e.g. washing to remove unbound analyte-MBP-SGC; and then, (v) incubating the separated solid phase with an enzyme substrate to detect the presence and/or amount of the MBP-SGC-enzyme bound to the murein-solid phase. The signal generated in the subject competitive assay is inversely related to the amount of analyte in the biological sample.

In a third representative example of a murein binding assay according to the invention, a murein-binding fluorescence histochemical assay includes the steps of: (i) collecting and fixing a biological sample (e.g., a tissue sample); (ii) incubating the sample with MBP-SGC (i.e., SGC is a fluorophore); (iv) washing the sample to remove unbound MBP-SGC conjugate; and, (v) detecting the bound MBP-SGC conjugate by fluorescence microscopy.

In a fourth representative example of a murein-binding assay according to the invention, a murein-binding cytometric assay (i.e., a cytofluorimetric assay), for diagnosing severity of fungal infection in a subject in need thereof commonly includes the steps of: (i) collecting a biological sample (e.g., a urine sample); and aliquoting the subject sample for testing; (ii) concentrating any bacterial or fungal analytes in the sample (i.e., by centrifugation, filtration and the like); (iii) treating the subject aliquot by means effective to simultaneously kill any pathogens, to eliminate interfering or confounding enzymes or compounds present in the sample, to disrupt any aggregated fungal cell clusters, chains, strands and the like, and to obtain a suspension of single fungal cells (e.g., treating with a solution of about 2 M NaOH and then, optionally, with a solution of protease, e.g., trypsin, supra); (iv) incubating the treated aliquot with MBP-SGC conjugate (e.g., SGC consisting of a fluorophore); (v) separating bound MBP-SGC conjugate from free/unbound MBP-SGC (e.g., by centrifugation as disclosed in EXAMPLE 5, below); and (vi) quantifying by cytofluorimetry the number of fluorescent particles present in the treated aliquot of the biological sample thereby to determine the severity of the infection in the patient.

Embodiments of the invention also provide kits useful for identifying eubacteria and fungi in a biological sample, e.g. a patient sample, or a sample of water or air. A representative kit contains the following: namely, one or more reagent packages at least one of which contains a MBP-conjugate; an assay buffer; an optional assay surface, e.g., a tray, a vessel, or dipstick; a set of instructions; and one or more optional assay calibrators or reference compounds (e.g., a positive and negative control). In one presently preferred embodiment, a kit contains reagent packages containing: (i) one or more pre-treatment solutions for exposing murein compounds in a bacterial or fungal cell wall (e.g., NaOH, protease, glycosidases or periodates (supra), and as illustrated in EXAMPLE 8, below); (ii) one or more reference calibrator solutions (e.g., 0.25% glutaraldehyde fixed single cell yeast suspensions, cell wall materials coated on latex beads (i.e., polystyrene and polyvinyltoluene homopolymers, and copolymers of these compounds with styrenes), and the like); (ii) one or more sensitivity enhancing solutions (e.g., acetylation reagent to increase the binding activity of a murein compound, e.g., EXAMPLE 8, below); (iv) one or more murein binding conjugates (e.g., MBP-FITC, MBP-enzyme, and the like); (v) one or more assay buffers or wash buffers (e.g., assay buffer containing PEG and/or detergents that promote binding between MBP and a murein compound); (vi) one or more periodate solutions for oxidizing carbohydrates and increasing the number of groups available for acetylation; (vii) one or more blocking buffers for reducing nonspecific background (e.g., solutions containing BSA or milk proteins); and (viii) one or more solid phase reaction surfaces upon which, or in which, the assay may be conducted (e.g., microtiter plates, dipsticks, strips, and the like.)

EXAMPLE 1

Preparations of Catalytically Inactive Murein Binding Polypeptides

Preparations #1: Mutant Catalytically Inactive Avian Lysozymes: Malcolm, B. A. et al. disclose (45) putative roles of the respective residues residing within the active-site of chicken lysozyme (EC 3.2.1.17) using a technique of site directed mutagenesis in a yeast shuttle vector derived from pBR322 and pJDB219, and also using two synthetic primers: one designed to effect a G to A change at base 237 and a second to effect a G to C conversion at 186. Two resultant mutant lysozyme enzymes were identified, i.e., one having Asp converted to Asn, i.e., D52N, and the second having Glu converted to Gln, i.e., E35Q. The D52N mutant enzyme reportedly exhibited less than 5% of the wild-type catalytic activity against *Micrococcus luteus* cell wall substrate while retaining some binding affinity for chitotriose $(GlcNAc)_3$. E35Q exhibited no measurable enzyme activity (i.e., less than 0.1%±0.1% of wild type) but also still bound substrate. Dissociate constants for enzyme-chitotriose complexes were reported: namely, 4.1 $\mu$M for D52N-chitotriose complexes and 13.4 $\mu$M for E35Q-chitotriose. The two mutant lysozymes were reportedly expressed and secreted by yeast transformants at levels of about 5 mg/L and purified by affinity absorption to, and high salt elution from, *Micrococcus luteus* cell walls, or alternatively, by affinity chromatography on chitin-coated Celite A and elution with a concave gradient from 1 liter of 0.15 M acetate buffer (pH 5.5) containing 0.5 M NaCl to 250 ml of 1 M acetic acid followed by isocratic elution with 1 M acetic acid according to methods described by Kuroki et al. (4.).

Since binding to simple di- and trisaccharides is not indicative of binding to cell wall compounds, experiments were conducted to determine (i) whether D52N, E35Q, or catalytically active lysozymes could bind bacterial cell wall fragments; (ii) whether substrates for any of the three lysozymes were exposed at the surface of the cell wall of intact bacteria and available for binding either of these lysozymes; (iii) whether intact bacteria and/or their fragments, as present in biological samples, contained intact substrates available for binding to any of the three lysozymes; (iv) whether potentially infectious samples could be treated to kill pathogens without destroying the ability of any bacteria to bind with a lysozyme; (v) whether a conjugate could be prepared with any of the three lysozymes; (vi) whether sufficient conjugate could be bound to the available bacterial cell wall materials in a biological sample to allow their detection in an assay; (vii) whether the binding between any of the lysozymes and the substrate in a biological sample would be of sufficient sensitivity or specificity to allow detection of bacteria in a biological sample; (viii) whether the lower limit of sensitivity for binding between a lysozyme and a bacteria in a biological sample would be sufficient to allow the use of a lysozyme as a diagnostic reagent; and, (ix) whether natural chitinase, lysozymes and mammalian, avian or plant materials would constitute substances capable of confounding or interfering in an assay using a lysozyme reagent. The results of these studies were remarkably encouraging, and surprisingly lysozyme, which has relatively poor catalytic activity with chitin substrates, was found to bind intact fungal cells. Certain of the results obtained in these studies, as relevant to illustrate various embodiments of the invention, are detailed in the EXAMPLES which follow. The results of these experiments show that lysozymes and catalytically inactive lysozymes and murein binding proteins are useful in preparation of diagnostic reagents.

Lysozyme and the subject D52N and E35Q mutant catalytically inactive lysozymes, produced by site-directed mutagenesis methods, are useful in preparation of diagnostics reagents, and catalytically inactive lysozymes constitute a presently preferred example of a murein binding polypeptide, as defined, supra and as possessing the requisite catalytic inactivity of an MBP. Diagnostic reagents incorporating the subject MB polypeptides into capture and detect reagents, and the like, according to the instant invention, are illustrated further below.

Malcolm et al. (45) is incorporated herein by reference for illustrative methods of measuring catalytic inactivity and association constant, e.g., from a soluble complex with a fluorigenic triose substrate. Catalytic inactivity can also, e.g., be determined by incubating a suspension of *Micrococcus lysodeikticus* (as a substrate) with a test sample of the lysozyme preparation in an assay volume of 2.6 ml and taking optical density measurements at 450 nm using a 1 cm optical path. "Inactive enzyme" shows a decrease in $A_{450}$ that is less than about 0.5 units per minute per milligram test enzyme protein. Catalytic inactivity can also e.g. be determined using an N-acetylglucosamine hexamer substrate labeled with 2-aminopyridine, e.g., using a method according to Hase et al. (48.)

Preparations #2: Mutant Catalytically Inactive Bacteriophage Lysozymes: Heinz and Matthews (46) disclose T4 lysozyme double mutant N68C/A93C in which surface residues Asn68 and Ala93 are replaced (using site-directed mutagenesis) with cysteine residues. The cysteines allow formation of dimers through disulfide exchange. N68C/A93C T4-lysozyme dimers purified by molecular sieve chromatography are catalytically inactive and retain binding activity for murein substrates.

Preparations #3A: Chemically Inactivated Lysozymes #1: Hinge-bending motion is required for catalytic activity at the lysozyme active site cleft and for cooperation between a substrate binding site in the "right hand" side of the cleft and a catalytic site in the "left hand" side of the cleft. Conformational restriction of lysozyme protein is accomplished using glutaraldehyde to react with free amino groups on the surface of the polypeptide and form intra- and intermolecular crosslinks that freeze the conformation of the protein.

Murein binding polypeptide, i.e., hen egg white lysozyme (Sigma Chemical Co., St. Louis, Mo.) is dissolved in about 2 ml of 0.1 M PBS, pH 6.8 to a final concentration of about 2–5 mg/ml. Glutaraldehyde is diluted in 0.1 M PBS, pH 6.8 from a commercial stock solution of 25% (Eastman Chemicals, Rochester, N.Y.) to a final concentration of 0.10% and 1 ml is added dropwise, with agitation to the 1 ml MBP solution. After 3 hours at room temperature the reaction mixture is placed into dialysis tubing and dialyzed against PBS, pH 6.8 overnight at 4° C. Remaining reactive glutaraldehyde sites are blocked by adding 0.5 ml of 1 M lysine in PBS, pH 6.8, and incubating for 30 minutes. Catalytically inactive glutaraldehyde-cross-linked lysozyme is purified by affinity chromatography at 30–37° C. on *Micrococcus lysodeikticus* cell wall fragments bound to cyanogen bromide-activated Sepharose. Catalytically active enzyme elutes in the wash and catalytically inactive enzyme remains bound. Bound inactive enzyme is eluted by incubation overnight at 4° C. in PBS, pH 3 containing 0.2 M N-acetylglucosamine and 2M NaCl. Inactive monomers, dimers and multimers are separated by molecular sieve chromatography on Sephacryl S-200 in PBS, pH 7.4. Inactive monomer is useful for preparations of conjugates with signal generating compounds, i.e., in 'detect reagents', while dimeric and multimeric forms are useful as 'capture reagents'. Alternatively, catalytically inactive lysozyme may be purified by ion-exchange and/or molecular sieve chromatography.

Preparations #3B: Chemically Inactivated Lysozymes #2: Active site charge distribution is also important for catalytic activity, e.g. Asp-52. Ethyl esterification with triethyloxonioum tetrafluoroborate at pH 4.5, e.g., according to Parsons et al. (47)is used to modify charge and catalytically inactivate hen egg white lysozyme, (i.e., to less than about 1% to 10% of the catalytic activity of the wild type untreated control enzyme), while retaining murein binding activity for the protein. Enzymatically inactive enzyme is separated by Bio-Rex 70 column chromatography similar to that described previously (47). Similarly, methylation was used to modify charge and catalytically inactivate hen egg white lysozyme.

Preparations #3C: Chemically Inactivated Lysozymes #3: Amidation of Asp and Glutamic acid residues through esterification and ammonolysis according to Kuroki et al. (41e) is used to chemically inactivate hen egg white lysozyme while retaining murein binding activity.

EXAMPLE 2

Murein Binding Polypeptide Signal Generating Conjugate: Esterified F-NHS-Lysozyme Conjugates consist of both a MBP and a signal generating compound (SGC; supra.) The following example discloses the preparation of a MBP-SGC conjugate, i.e., esterified-lysozyme-MBP (Preparation #3B, above) chemically linked to F-NHS as the SGC, according to the method disclosed below.

The following steps were conducted in the dark: namely, Purified esterified-lysozyme(lyophilized powder), 10 mg, was dissolved in 1 ml of 0.03 M bicarbonate buffer, pH 2.5–3.0 containing 0.15 M NaCl.

NHS-Fluorescein (F-NHS), 0.5 mg, was dissolved in 500 µl of DMSO and 50–100 µl of the resulting stock solution was added dropwise, with mixing, to the esterified-lysozyme solution. The resulting conjugation solution was placed on ice for 2 hours.

Unconjugated F-NHS was removed by chromatography on a PD-10 column (Pharmacia, Piscatawy, N.J.) that was equilibrated with 0.01 M phosphate buffered, pH 7.0–7.4, 0.15 M saline (PBS). The first 2.5 ml emerging from the column contains fluorescent peaks that were discarded (i.e. conjugated denatured aggregated polypeptides); the second 2.5 ml emerging from the column was collected (i.e., MBP-SGC conjugate); and remainder of the material on the column (i.e., free F-NHS) was discarded.

Concentration of F-NHS-esterified-lysozyme conjugate was estimated by determining optical density at 280 nm ($OD_{280}$) assuming an extinction coefficient for the conjugate equal to 1.0. For use in a diagnostic reagent the concentration of the F-NHS-conjugate was adjusted to 400–500 µg/ml with PBS, pH 7.0. Preferably the absorbance ratio of F-NHS at $OD_{590}$ to MBP at $OD_{280}$ was about 1:1, because at higher ratios there was more nonspecific precipitate in the conjugation reaction, and at lower ratios there was less efficient signal generation in diagnostic assays. EXAMPLE 3

Murein Binding Polypeptide Conjugates with Signal Generating Compounds

Preparation #1: Horse Radish Peroxidase-Catalytically Inactive-Lysozyme Conjugate (HRP-MBP-Conjugate #1).

Murein binding protein, i.e., mutant lysozyme (EXAMPLE 1, Preparation #2, supra), was conjugated to horse radish peroxidase (Grade I, Boehringer Mannheim, Indianapolis, Ind.) to achieve a mole ratio of HRP:MBP of about 2:1. Most proteins do not contain free sulfhydryls, but this is not the case for the N68C/A93C T4-lysozyme mutant described above, with free $Cys_{68}$ and $Cys_{93}$. In addition, disulfide cross-linked in inter- or intramolecular bonds in polypeptides are often susceptible to mild reduction (i.e., using 1–20 mM dithiotreitol; DTT) creating one or more reactive sulfhydryl residues, without loss of binding site affinity for a ligand. In either case, lysozyme free sulfhydryl groups are reactive with MBS (m-Maleimidobenzoyl-N-hydroxysuccinimide ester) cross-linking agent. In one example, a reactive sulfhydryl in HRP is generated by reacting free amino groups with SPDP (N-succinimidyl-3-(2-pyridyldithio)propionate). Mild reduction of SPDP removes the pyridyl group exposing a reactive sulfhydryl. Conjugation between MBS-MBP and SPDP-HRP is accomplished by reducing (i.e., with DTT) then mixing the compounds under conditions favorable for disulfide bond formation.

MBS-MBP: m-Maleimidobenzoyl-N-hydroxysuccinimide ester (MBS; Pierce Chemical Co., Rockford, Ill.) is dissolved to a concentration of 70 mM in dioxane. A 50-fold molar excess of MBS is added with stirring to a solution of N68C/A93C T4-lysozyme, and the mixture is incubated for 1 hour at 37° C. Excess reagent is removed by G-25 -chromatography. The modified MBP elutes in the void volume is ready for reaction with thiol-HRP enzyme (below).

SPDP-HRP: 3-(2-pyridyldithio)-propionic acid N-hydroxysuccinimide ester (Sigma, #P9398) contains a blocked thiol present as a 2-pyridyl disulfide group. The pyridyl is removable under conditions that leave nascent disulfide bonds intact. The resultant thiol-enzyme is then reacted with MBS-modified MBP to generate the HRP-MBP conjugate.

10 mg HRP (250 nmoles) is dissolved in 0.5 ml PBS, pH 6.8 containing 0.15 M NaCl and chromatographed on a G-25 column to remove low molecular weight contaminants that might react with SPDP. The enzyme elutes in the void volume and can then be collected by visual inspection of the column effluent (this protein has a distinct brownish color.) A fifteen-fold molar excess of SPDP was added dropwise to the enzyme solution with stirring. The reaction mixture was left at room temperature for 30 minutes and excess SPDP reagent is then removed by gel-filtration on G-25 (as above). Modified HRP elutes in the void volume and is well separated from the excess SPDP. There should be no loss of enzyme activity and the HRP-SPDP conjugate is stable for >2 weeks when stored at 4° C. as the 2-pyridyl disulfide derivative. The extent of coupling is determined by taking a 50–100 $\mu$l aliquot of SPDP-HRP, diluting to 1 ml with distilled water and measuring the absorbance at 403 nm and 343 nm against a distilled water blank. The amount of 2-pyridyl sulfone released from the test sample is used to quantify the extent of conjugation. To this end, DTT is added to a final concentration of 25 mM and the absorbance at 343 nm is read again after about 5 minutes. The difference in absorbance before and after addition of DTT represents the amount of 2-pyridyl sulfone released and is stoichiometrically related to the total amount of 2-pyridyl disulfide bound to the HRP in the test sample. The extinction coefficient for the released 2-pyridyl sulfone is $8.08 \times 10^{-3}$ M-1 cm-L and the extinction coefficient for HRP is 2.5 at 403 nm. From the data the degree of coupling of SPDP is calculated. Under the conditions described (i.e., with a molar ratio of 15–20\SPDP mole: mole HRP) an average of about 2.3 SPDP molecules are bound to each molecule of HRP.

HRP-MBP Conjugate: Enzyme-SPDP, i.e., HRP-SPDP (above), is reduced to give the corresponding protein-thiol for reaction with MBS-MBP. Suitable conditions that allow reduction of the protein-2-pyridyl derivative, with reducing intramolecular disulfides, are achieved at acidic pH, i.e., in 0.01 M Tris-buffered, pH 3.0, 0.15 M saline (TBS, pH 3), as follows. First, the SPDP-enzyme derivative is passed over a G-25 column equilibrated in TBS, pH 3, and the void volume protein peak is collected. Next, DTT is added to protein peak to a final concentration of 25 mM. After treatment for 30–40 minutes at room temperature the thiolated protein is separated from the low molecular weight reactants (i.e., 2-pyridylsulfone) by gel filtration on G-25 equilibrated in PBS, pH 7.2. Finally, the purified HRP protein-thiol is added to the MBS-MBP derivative (above) at about a 1:1 mole ratio and the mixture is allowed to stand at room temperature for 30–40 minutes. 2-mercaptoethanol is added to a final concentration of 10 mM. Purification of the HRP-MBP conjugates is accomplished on Sephacryl-S200, or on Fractogel TSK using FPLC (Fast Protein Liquid Chromatography; Pharmacia).

Preparation #2: HRP-MBP Conjugate #2:

In two separate but parallel preparative procedures, exposed amino groups on MBP, (i.e., E35Q catalytically inactive lysozyme from EXAMPLE 1—Preparation #1 supra), and on horse radish peroxidase (HRP) are maleimidated using 6-maleimido caproic acid N-hydroxylsuccinimide ester (MCS). Molecular sieve chromatography on Sephacryl-S200 (Pharmacia Fine Chemicals, N.J.) is used to separate maleimidated-HRP or -MBP monomers from aggregates and multimers in each of the respective different preparations. Purified monomers in each preparation are independently thiolated by brief treatment with N-acetyl homocysteine thiolactone (AHTL) to achieve mole ratios of about 1–2 thiol groups per mole MBP (or HRP). (Thiol mole ratios are determined using the fluorescamine fluorometric method.) Thiolated-HRP and thiolated-MBP products are each independently dialyzed against 0.2M acetic acid, lyophilized and stored at 4° C. until use. For coupling each of the lyophilized reagents is dissolved separately in an aliquot of nitrogen-saturated 0.1 M succinate buffer, pH 6.0 containing 0.04% EDTA. Coupling of the thiolated-HRP to the thiolated-MBP is accomplished under the conditions described in Preparation #2, above (i.e., HRP-MBP Conjugate, supra), by mixing the two preparations together at differing ratios of thiol-HRP to thiol-MBP (i.e., 1:1, 2:1, 3:1 and 5:1.) The HRP-MBP conjugate is purified by molecular sieve chromatography on G-25 and then Sephacryl S-200 and fractions containing HRP:MBP different mole ratios are collected separately for testing. Testing includes both a determination of HRP enzyme activity and murein binding ability. For long term storage at 4° C. or –20° C., the MBP-HRP-conjugate was stabilized by addition of: ferrous sulfate to a final concentration of $10^{-4}$ M, BSA to a final concentration of 1%; and Tween-20 to a concentration of 0.05%.

Preparation #3: Alkaline Phosphatase-Catalytically Inactive Lysozyme Conjugate:

Alkaline phosphatase (Type VII, Sigma Chemical Co., St. Louis, Mo.) is dialyzed to 100 mM Tris-HCL buffer, pH 8.0. To convert Alkaline phosphatase hydroxyl groups to chemically reactive aldehydes that form Schiff bases with amines in MBP, (i.e., mutant lysozyme from EXAMPLE 1—Preparation #1, above), 0.5 ml of the dialyzed Alkaline phosphatase enzyme is mixed with 500 $\mu$l of a periodate solution (214 mg sodium periodate in 10 ml potassium phosphate buffer, pH 8.0) and agitated for 1 hour in the dark at room temperature. Periodate is removed by centrifugation and the pH adjusted to 8.0 with potassium carbonate. MBP, 2 mg in 200 $\mu$l, is added and the mixture incubated for 1 hr. at room temperature in the dark, after which time the pH is adjusted to 6.0 with formic acid. Excess free aldehydes are reduced by adding 300 $\mu$l sodium cyanoborohydride (6 mg/ml in 500 mM sodium phosphate buffer, pH 6.0) to the reaction mixture. The resultant Alkaline phosphatase-MBP conjugate is purified by dialysis overnight to TBS, pH 8 followed by G-25 and S-200 column chromatography in TBS, pH 8.0.

Preparation #4: F-NHS-NHS Conjugates:

Fluorescein-NHS (F-NHS, Pierce Chemical Co., St. Louis, Mo.) was found to produce more stable conjugates with MBP than fluorescein (FITC), and with less precipitate formed during the conjugation procedure. A 1–3% (w/v) stock solution of F-NHS was prepared in DMSO. 50 $\mu$l to 100 $\mu$l of this stock solution was added dropwise to 1 ml of a 10 mg/ml solution of MBP protein in 50 mM bicarbonate buffer, pH 8.5, i.e., catalytically disabled or catalytically active lysozyme (supra) to achieve a final F-NHS concentration of about 1.0 to 7 mg/ml. After storage in the dark on ice at 4° C. for 2 hours (or overnight), free F-NHS was removed from conjugated F--NHS MBP by dialysis (i.e., to PBS) or molecular-sieve chromatography on G-25M (i.e., in PBS, pH 7.0; Pharmacia, Piscataway N.J.; "PD10" column). Protein concentration was determined spectrophotometrically at 280 nm assuming a molar extinction coefficient of 1.0, and the final concentration was adjusted to about 0.4–0.5 mg/ml.

EXAMPLE 4

Preparation of MBP Solid Phases

Preparation #1: Lysozyme-Nylon 6 Solid Phase:

Nylon-6 plates (or filters) are soaked in a 3N HCl solution for about 1 hour at 37° C. After rinsing with distilled water the amidated plates are thiolated using 0.05 M N-Acetyl homocysteine thiolactone (AHTL) in 1 M imidazole (in a saturated nitrogen atmosphere) and incubating at room temperature overnight. Thiolated plates (or filters) are washed 4–6 times with 0.2 M acetic acid or until no thiol is detected in the wash by Elmens reaction. The plates are stored under nitrogen until use.

MBP is maleimidated to about 1–2 maleimide groups/mole MBP using N-hydroxy succinimide ester (MCS), the product is purified by molecular sieve chromatography (Sephacryl S-200), lyophilized, and stored under nitrogen at 4° C. until use.

Thiolated Nylon-6 plates (or filters) are soaked in nitrogen saturated 0.1 M succinate buffer, pH 6.0, containing 0.04% EDTA and covalent coupling is achieved by adding maleimido-MBP (above) at about 2 mg/ml and incubating at room temperature (under nitrogen) overnight. After washing to remove unbound MBP, free sulfhydryl groups are blocked by treating with 0.15 M NaCl containing N-ethyl maleimide for about 30–45 minutes. The plates are prepared for use by washing with 0.15 M NaCl until the $OD_{280}$ of the wash solution is less than about 0.03.

Preparation #2: Lysozyme-Nitrocellulose Solid Phase:

Nitrocellulose filters (0.45$\mu$ pore size; Schleicher & Schull, #BA85) are washed in 10 mM Tris-HCL buffer, pH 8 containing 20 mM NaCl and 0.1% Triton X-100. Circles, i.e., "dots", having a diameter of about 3–4 mm are scribed onto the surface of the nitrocellulose using an indelible ink.

Murein binding polypeptide, in this case lysozyme (Sigma Chemical Co.), is dissolved in 62.5 mM Tris-HCL buffer, pH 6.8 containing 0.1% SDS, 20 mM DTT and 5% BSA. For loading onto the nitrocellulose 10 $\mu$l of the MBP solution is added to each of the dots on the filter, and adsorption is achieved by incubation at room temperature for a time sufficient to retain murein binding capacity but eliminate catalytic activity, i.e., 15–30 minutes. Unbound sites on the nitrocellulose are blocked by washing with 10 mM Tris-HCl, pH 7.4 containing 0.9% saline and 5% BSA (Tris-saline-BSA). The filter is stored in a humidified chamber on top of a Tris-saline-BSA saturated Whatman (Grade 1) filter paper until use. Coupling in the presence of 0.1% SDS and 20 mM DTT results in loss of enzyme activity but retention of murein binding activity.

Preparation #3: Coupling to Glass: Glass-arylamine Derivatives of Silanized Glass were prepared and MBP, i.e., lysozyme from EXAMPLE 1, Preparation #3, is covalently bound according to the following method.

Fine controlled pore glass beads (approximately 0.3–1 mm in diameter; Corning) were washed with 5% nitric acid and silanized by addition of 10% $\gamma$-aminopropyl-triethoxysilane in distilled water at pH 3.45. Silanized glass is reacted with p-nitrobenzoylchloride in chloroform containing 10% (v/v) triethylamine as a scavenger for hydrogen chloride. The resulting nitro group is reduced using 10% sodium dithionite in distilled water and the resulting p-aminobenzoylaminoalkyl derivatized glass is diazotized with nitrous oxide generated in situ by HCl and sodium nitrite. After washing MBP is added in Tris-HCl, 0.15 M saline, pH 8–9. Approximately 50 $\mu$g of MBP may be coupled per 50 mg glass beads. For use in a solid phase ELMBPA (below), the MBP-conjugated glass beads are filtered into the pores of a glass fiber filter (Whatman, GF/C) and non-specifically reactive sites in the glass fiber filter are blocked by washing with Tris-HCl, 0.15 M saline, pH 7.2 containing 5% BSA. The resultant surface has the advantage of having a high density of MBP capture reagent per unit area of glass bead impregnated filter.

Preparation #4. Covalent Coupling of MBP to Polystyrene Containing Beads:

Polystyrene beads, e.g., latex beads, are available commercially in a variety of sizes (e.g., 0.01$\mu$–7 mm) and with surface carboxyl-, carboxylate-modified-, sulfate-, amino-, and amidated groups available for coupling to a MBP. Covalent coupling increases the stability of bound MBP and ease of handling.

Preparation #4A: For cytometry, polystyrene beads having a diameter of about 0.5$\mu$ are collected by centrifugation and washed with 10 mM phosphate buffered pH 7.0 saline (PBS) until the optical density of the decanted PBS wash solution is less than 0.010 at 600 nm. Covalent coupling is achieved by activating about 0.2 ml of packed beads for about 30 min. in 25 ml of pentane-1,5-dial (Sigma Chemical Co., St. Louis, Mo., #6–5882) at a final concentration of 0.5% in distilled water, and with regular agitation. Following activation beads were washed with 10–15 ml distilled water and then PBS. Covalent coupling was achieved by adding a 1 mg/ml solution of MBP, i.e., F-NHS-lysozyme (supra).

Preparation #4B: For mobile latex phase dipsticks, polystyrene beads having surface carboxyl- groups and a diameter of about 0.01–0.1$\mu$ are collected by centrifugation, washed in PBS, pH 6.5. The beads are activated using water-soluble carbodiimide (i.e., 1-ethyl-3-(3-dimethyl aminopropyl)carbodiimide hydrogen chloride, 10 mg/ml distilled water, pH 4.5–4.8); washing after 30 min.; and coupling to amino groups in MBP is achieved by adding a solution of 1 mg/ml MBP, (i.e., RP-lysozyme, supra) in PBS, pH 6.5.

EXAMPLE 5

Urine Diagnostic Assays

Uses of the subjects assays according to the invention include detection of bacteria in a biological sample consisting of a sample of urine.

Sample Preparation: A normal human urine sample was collected, varying numbers of *E. coli* or *Candida albicans* cells were added to separate urine aliquots to simulate samples from an infected individual, and then to concentrate the bacterial or fungal particles the samples were either centrifuged 3000 rpm in a clinical centrifuge for 10 minutes, or filtered through a Whatman glass fiber or Millipore 0.22$\mu$ pore filter.

For samples containing bacteria, the centrifugal pellet (or filtrate) was treated to kill infectious material, i.e., by fixing and killing with 80% ethanol for 5 minutes or longer, or alternatively, by alkaline hydrolysis (as described below.) For samples containing fungi, the centrifugal pellet (or filtrate) was subject to alkaline hydrolysis to kill and denature fungi, disaggregated fungal clumps, and removed confusing and interfering substances (supra.) The conditions for alkaline treatment of the urine sediment sample were found to be crucial to obtaining uniform suspensions of killed and denatured particles, and in turn, for obtaining meaningful results in cytometric particle counting assays. Urine sediment samples contained aggregated bacterial and fungal rafts, clusters and clumps, as well as, particulate matter that bound bacteria and fungi and interfered with performing measurements in the assay. Alkaline hydrolysis and/or supplemental treatment with one or more proteases, were evaluated including treatments with 0.2 M, 1 M, 1.5 M, 2.0 M, and 5 M NaOH at 37° C., 45° C., 60° C. or 100° C. for 5 minutes, 10 minutes or 30 minutes. Treatments with the lower concentrations of NaOH, and/or for the shorter times, and/or at the lower temperatures killed and denatured all test bacteria and fungi, as determined microscopically by refractility and microbiologically by plating and culturing. Under the lesser denaturing conditions (e.g. 1 M NaOH for 2–10 minutes) some rafts and aggregates of fungal cells were observed, and these could dispersed into single particle suspension by following the alkaline treatment with a protease treatment, i.e., 0.25% w/v trypsin for 2–15 minutes. Conditions giving excessive killing and denaturation were adopted as a standard protocol to provide an extra margin of safety, i.e., treatment with 2 M NaOH at 60° C. for 30 min. and because they eliminated aggregates. (The margin of safety necessary for different types of biological samples will, of course vary.). The fixed and/or killed and denatured bacterial and fungal particles were next collected (e.g., by centrifugation or filtration, supra) and resuspended e.g., in 200 μl PBS containing a final concentration of 2.5% BSA (PBS-BSA.)

Fluorescence Microscopy: Assay #1: 50 μl of the MBP-conjugate reagent catalytically inactive F-NHS-lysozyme (Preparation #1, supra) or catalytically active F-NHS-lysozyme (Sigma) was added the urine sediment or filtrate (supra) at a final protein concentration of about 40–80 μg/ml. The binding to bacterial murein or fungal murein-like compounds in the biological sample was accomplished over about 10–30 minutes at room temperature.

counting of monomeric beads the lower detection limit of a cytometer (i.e., Coulter Instruments) is set to greater than $0.5\mu$. using $0.5\mu$ calibration beads. Next, measured dilutions of the incubation mixture containing bacteria or fungi bound in multimeric detection beads, is gently vortexed to create a uniform suspension and then introduced into the flow cytometer. Multimers having diameters greater than $0.5\mu$ are counted, and the number of such particles is an indication of the presence, or amount, of bacterial contamination in a biological sample, or the severity of infection in an animal.

Flow Fluorimetry: Assay #3:

Bacteria (*E. coli*) from in vitro culture, containing clumps and aggregates, were suspended in PBS, stained using F-NHS-lysozyme (200 μg/ml/30 minutes/37° C.), and detected using fluorescence microscopy, or fluorescence flow cytometry in a Becton Dickinson FAXSCAN system (LYSIS II, ver. 1.1, 1992.)

FIG. 1A shows background auto-fluorescence in the *E. coli* sample prior to staining with F-NHS-lysozyme.

Figure 1B:
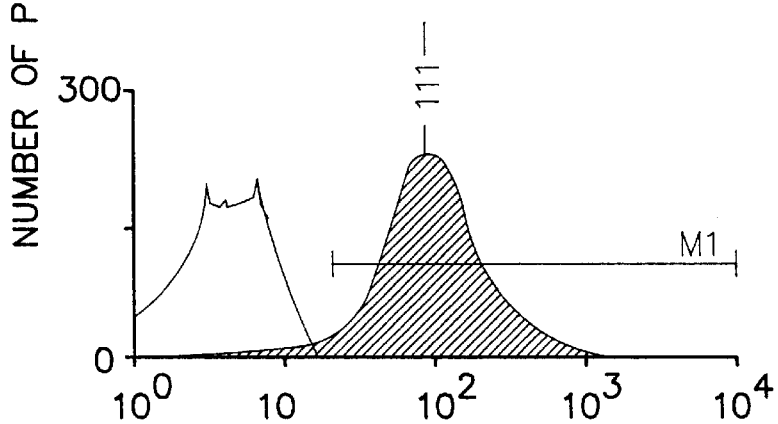
FIG. 1B shows binding of an F-NHS-conjugated murein-binding protein (MBP) to bacteria as visualized by cytofluorimetric analysis and plotting fluorescence intensity (horizontal axis) against the number of incidents (i.e., particles counted; vertical axis) to form a histogram plot as disclosed further in EXAMPLE 5, below.

FIG. 1B shows F-NHS-stained bacterial aggregates (shaded peak) separated from the superimposed peak (unshaded peak) of auto-fluorescence shown in FIG. 1A.

The numeric data recorded by the flow cytometer, i.e., corresponding with FIG. 1A and 1B, is presented in TABLE 5.

TABLE 5

Cytometry Data: *E. coli* Urine Sediment Sample

| Figure | Channel | Window[a] L | Window[a] R | Particles Counted | % Total | Peak[b] Counted | Peak Channel 1 | Mean Intensity | Median Intensity | S.D. |
|---|---|---|---|---|---|---|---|---|---|---|
| 1A | 0 | 1.00 | 9646 | 10,000 | 100 | 705 | 1 | 6 | 3.8 | 15 |
| 1A | 1 | 19.8 | 9646 | 286 | 3 | | 21 | 42 | 28 | 80 |
| 1B | 0 | 1.00 | 9646 | 10,000 | 100 | 204 | 111 | 182 | 120 | 256 |
| 1B | 1 | 19.8 | 9646 | 9548 | 96 | 204 | 114 | 190 | 129 | 259 |

[a]Window, fluorescence intensity settings for lower and upper limits;
[b]Peak Counted, number of particles counted at the peak of fluorescence intensity.

"Bound" reagent F-NHS-lysozyme (i.e., bound to any bacterial or fungal particles in the sample) was removed from "free" by centrifugation (above) and the particles were washed 2–3 times with about 100 μl each of PBS-5% BSA, pH 7.0. The final sample was resuspended in about 10 μl of PBS-5% BSA, pH 7.0 and the presence (or amount) of F-NHS-lysozyme bound to the particles in the sample was determined visually by fluorescence microscopy at a magnification of 1000×. Normal urine purposefully contaminated with known numbers of either *E. coli* or *Candida albicans* gave positive test results (i.e., visible fluorescent particles) in the assay.

Flow Cytometry: Assay #2:

Despite manufacturers claims to the contrary, bacteria and fungi are relatively difficult to detect by flow cytometry because their size falls at the lower limits for detection by ordinary (non-laser) forward light scattering methods.

Bacteria or fungi are detected by adding 50 μl of F-NHS-lysozyme covalently bound to 0.5 μ polystyrene beads (Solid Phase Preparation #4A, supra) to a treated urine sediment (prepared, supra). After incubating for about 10 min. to about 20 min. to effect binding of the F-NHS-lysozyme-beads to bacteria or fungi in the sample forming dimeric and multimeric aggregates, the number of multimers is determined by cytometry as follows. First, to exclude Flow Fluorimetry: Assay #4:

Endogenous murein binding polypeptides in bacterial cell wall were detected using an antibiotic-SGC conjugate, i.e., ampicillin chemically bonded through its free amino group to F-NHS. Briefly, ampicillin was mixed with F-NHS (Pierce Chemical Co.) according to methods described supra in regards to preparation of F-NHS-lysozyme. Since only one free amino group was available for binding, the stoicheometry of binding was 1:1. Antibiotic-SGC conjugate was separated from free F-NHS and free antibiotic on a P2 sizing column, i.e., the conjugate was about twice the size of the free antibiotic. The F-NHS-ampicillin was used to stain endogenous peptidyl transferases in the cell walls of bacteria (i.e., *E. coli*) and fungi (i.e., *Candida albicans*) and stained bacterial and fungal cells were detected using flow cytofluorimetry and microscopy. Because of its small molecular size F-NHS-ampicillin was able to stain viable bacteria and fungi, as well as killed and denatured bacteria and fungi.

EXAMPLE 6

Enzyme Linked Murein Binding Assay: ELMBA
Solid Phase Sandwich Assay

Murein binding polypeptide (MBP) capture reagent, in this case catalytically inactive hen egg white lysozyme from EXAMPLE 1 (above), is dissolved immediately before use in 0.05 M sodium carbonate buffer, pH 9.6 to achieve a final concentration of about 100 μg/ml. A solid phase (supra) is coated with MBP by adding 100 μl of the MBP-capture carbonate solution to each well in a 96 well microtiter plate (ELISA standard polystyrene; Nunc Inc. or Immulon-II, Dynatech Inc.). After coating the plates at 4° C. for 16–20 hours, unbound MBP is removed by washing 4–6 times with 0.01M sodium phosphate buffer (PBS), pH 7.0 containing 0.5% Tween20 (PBS/Tween). Unbound sites on the polystyrene are blocked by adding PBS, pH 7.0 containing 10 mg/ml of bovine serum albumin (BSA) and 0.5% Tween-20 (Blocking Buffer), and incubating for 3–4 hours at room temperature. Blocking buffer is removed by washing with PBS/Tween and the microtiter plates are covered and stored at 4° C. until use. Test samples of biological fluid, i.e., a urine sediment sample (supra), are prepared as serial dilutions in PBS, pH 7.0 and 100 μl of each dilution is added to a well of the coated microtiter plate containing the bound MBP. Binding between the MBP and any bacterial murein, or fungal murein-like, analyte in the test sample is allowed to continue for 45 minutes to 1 hour at room temperature, and then unbound materials are removed by washing 4–6 times with PBS/Tween. Bound murein, or murein-like, analyte is detected stepwise: first, by adding 100 μl/well of a detect reagent HRP-lysozyme-conjugate (EXAMPLE 3, above) dissolved in PBS, pH 7.0. The reaction between the detect reagent and the bound-analyte is allowed to continue at room temperature for 30–90 minutes and unbound detect reagent is next removed by washing with PBS/Tween, followed by PBS. Second, the bound detect reagent is visualized by adding 100 μl of a colorimetric substrate for HRP, i.e., a solution of ABTS (2,2'-azino-di(3-ethylbenzthiazoline sulfonic acid) at a concentration of 0.16 mg/ml in PBS, pH 6.0 and containing 0.0004% (freshly prepared) hydrogen peroxide. Visible color development is allowed to continue for 10–60 minutes, and absorbance is quantified spectrophotometrically at 405 nm (i.e., in an ELISA plate reader). Third, the results are quantified by comparing the absorbance recorded with the absorbance produced by measured amounts of murein ligand standards run in parallel, i.e., in other wells of the MBP-capture microtiter plate during the assay of the test substance. The absorbance produced by the standards is used to construct a standard curve, and the absorbance value for the test sample may be compared with the standard curve to determine the bacterial-equivalents of a murein, or murein-like, ligand in the sample. The results, may be used to set acceptable cut-off values of reactivity for "normal" in the assay, e.g., an "infection" may indicated if a value obtained with a test sample from an individual is more than one standard deviations greater than a mean background value recorded with a panel of sample from normal healthy individuals. Individual cut-off values may also be indicated for different clinical grades (severity's ) of infection.

EXAMPLE 7

Dot-blot Filter Assay for Biological Samples

Assay #1: A solid phase filter is coated with an MBP capture reagent, in this case a Whatman glass fiber filter (GF/C) impregnated with fine controlled pore glass beads to which lysozyme is covalently linked, i.e., EXAMPLE 4, Preparation #3.

A sample of a biological fluid, i.e., a cerebrospinal fluid (CSF) sample is collected in a sterile manner and 200 μl aliquots of neat (undiluted), and diluted samples are prepared using 10 mM Tris Buffered, pH 7.2 0.15 M saline (TBS). The aliquots are each subject to pressure filtration (e.g., applied by a syringe) through a separate portion (i.e., a "dot") of the MBP-coated-filter (supra). Reactive sites on the filter are blocked by washing "blocking buffer", i.e., TBS containing 0.5% Tween and 1 mg/ml BSA, supra, through the filter. After washing the filter with 5–10 ml blocking buffer, bacteria, fungi and/or cell wall degradative products trapped on the filter are visualized by adding 100 μl of detect reagent, i.e., lysozyme-alkaline phosphatase conjugate (EXAMPLE 3, Preparation #3, supra.) After an additional 15–45 minutes incubation at room temperature, unbound detect reagent is removed by washing with about 5–10 ml TBS. The presence or amount of bacteria or fungi in the biological sample is visualized by adding about 1 ml of an alkaline phosphatase substrate, (i.e., 1.5 mM bromo-chloro-indolyl phosphate in 1.0 M diethanolamine containing 0.5 mM magnesium chloride, pH 9.6), and incubating until color appears. Quantification of the bound bacteria or fungi is accomplished by eluting the blue product from the filter in 200–500 μl of 80% ethanol, followed by spectrophotometric analysis at 605 nm and comparison against standards.

Assay #2: Conditions for this assay are as above (i.e., Assay #1), but the MBP detect reagent is a lysozyme-HRP-conjugate, (i.e., EXAMPLE 3, Preparation #2.). Peroxidase substrate used in this assay is 4-amino-antipyrene whose product precipitates from solution as a visible red color on the glass fiber filter, and the substrate solution consists of 0.2 mM 4 amino-antipyrene in 0.01 M sodium phosphate buffer, pH 7.5 containing 0.0004% (fresh) hydrogen peroxide and 20 mM henol.

EXAMPLE 8

Diagnostic Assay for Fungal Infections

The following example illustrates the instant diagnostic methods as used to rapidly identify a bacterial or a fungal infection; or, to rapidly differentiate between a bacterial and a fungal infection in a host in need thereof; or, to quantify the severity of a fungal infection in a patient in need thereof, e.g. a urinary tract infection.

Urinary Tract Infections: Urinary tract infections (UTI) include urethritis (infection of the urethra), cystitis (bladder infection) and pyelonephritis (kidney infection.) Bacteria and fungi are common etiologic agents in UTI. Most bacterial infections are E. coli, Klebsiella or Proteus and fungal infections are yeast of the genus Candida (e.g., C. albicans, C. kruzei, C. glabrata, C. tropicalis and the like) and fungi of the genus Torulopsis (e.g., T. glabrata) and Trichosporon (e.g., T. beigelii.). There are great differences in the assay sensitivity required to detect bacterial or fungal infection. For instance, threshold for UTI for bacterial infection is considered to be greater than about $10^5$ colony forming units (CFU), as contrasted with only about 1000 CFU/ml urine to confirm a yeast infection. Most antibiotic treatment is initiated before, or without, identification of the etiologic agent because several days are usually required to culture the bacteria or fungi responsible. Widespread use of antibiotics has favored emergence of antibiotic resistant bacteria and fungi, and the growing prevalence of resistant microbes (particularly in the clinical environment) has complicated treatment of patients. Among patients with fever and pyuria unresponsive to antibiotics the mortality rate is presently greater than 30%. In addition, several patient groups are at an increased risk of developing life-threatening ascending infections capable of developing into kidney and/or systemic infections: namely, immunocompromised patients (e.g., transplant, cancer patients, AIDS patients) including patients treated with immunosupppressive drugs (e.g., patients with autoimmune diseases such as IDDM, SLE, RA); indigent, elderly and diabetic patients; and, hospitalized patients (e.g., nosocomial infection, prostate disorders, pregnant women.) As a means for reducing costs, managed healthcare will eventually mandate early diagnosis and use of methods for distinguishing at an early stage between bacterial and fungal UTI infections.

Clinical Diagnostics Laboratory Testing: Current methods of plate culture and microscopic examination are too slow (i.e., days) to provide information useful in deciding treatment, and instead are used, (after the fact), to confirm bacterial, and/or fungal, infection. Current microscopic wet mount and/or plate culture methods are used to identify yeast in urine sediments. For detection by microscopic examination, more than 1000 colony forming units of yeast per milliliter of urine may be required; and, for detection by culture, 2 or more days may be required since yeast are relatively slow growing. As a result, false-negative test results and uncertainty are common. Alternative methods such as ELISA, calcofluor and PCR are expensive, slow, not easily automated, not pan-fungal reactive, often reactive with mammalian cell elements and bacteria, and have high background non-specific reactivity with non-fungal particulate matter (e.g., cotton lint). Performing these assays also commonly requires specially trained personnel. Existing techniques also do not commonly aid the physician to identify or determine a severity of infection or provide information useful in deciding whether to treat with an aggressive course of high-dose antibiotic therapy.

Current Limitations to Flow Cytometry Methods

Flow cytometry has limitations when used for automated counting of infectious microorganisms including: high background counting of non-microbial particles; the small numbers of microorganisms present (e.g., <1000 cells/ml yeast) necessitating long counting times at the lower limits of machine counting. For a 10 ml urine sample, it is preferable to count about 7,000–10,000 cells to diagnose a yeast UTI, but using e.g. a urine sediment sample of 500 μl, counting at 20 cells per second at a flow rate of 60 μl/minute may require 6–7 minutes per sample to record this number of cells. As a further complication for cytometric counting, it was discovered that bacteria and fungi in urine tend to aggregate and form into clumps, rafts and aggregates which may be commingled with mammalian cell debris in the samples (FIG. 2A.)

Figure 2A:
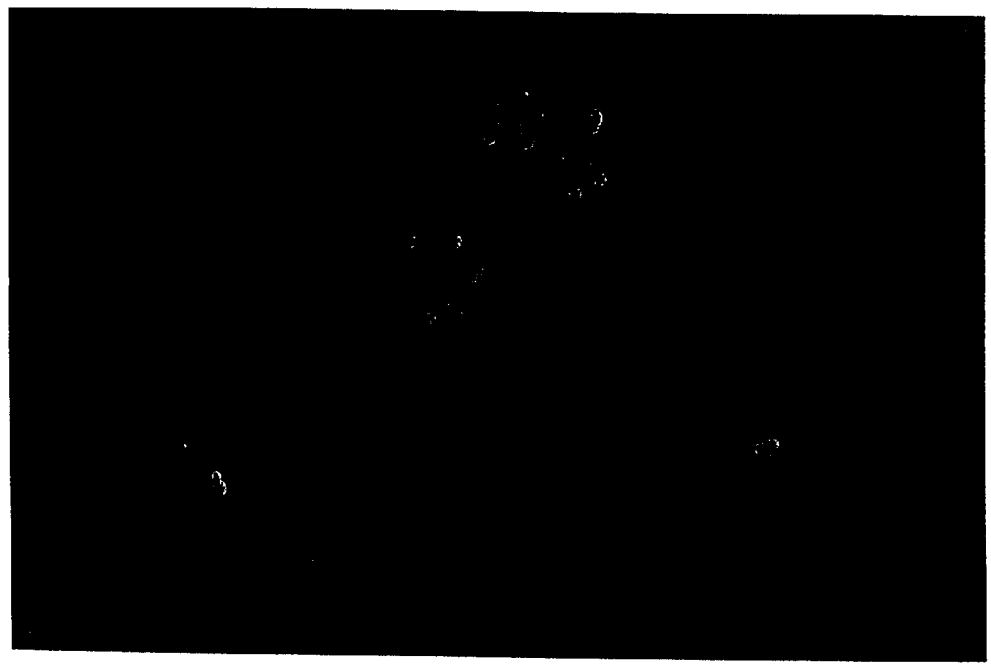
FIG. 2A shows a fluorescence photomicrograph of staining of clusters, rafts and aggregates of fungal cells in a urine sediment sample as visualized by staining with an MBP-F-NHS-conjugate, as disclosed in EXAMPLE 8, below.

FIG. 2A shows a fluorescence photomicrograph of staining of yeast clusters and aggregates observed when *Candida albicans* was added to normal urine sediment and stained with F-NHS-catalytically disabled lysozyme.

Filamentous fungi also grow in chains or hyphae that are not conducive to counting by cytometric methods. Due to these combined confounding properties, particle counting methods may often under-estimate the actual numbers of cells by more than 5–10 fold. Similarly, culture methods may under-estimate the numbers of fungi by at least 2–3 fold because many yeast colonies originate from cell clusters (Perfect, 1991.).

The Instant Assay Methods: Summary Overview

Since biological samples from infected individuals contain bacterial and fungal aggregates, as well as, 'confounding' and 'interfering' substances (supra), i.e., murein binding compounds such as endogenous chitinases and lysozymes attempts were made to produce single cell fungal and bacterial suspensions by combinations of acid and/or base hydrolysis and protease treatment.

As detect compounds, F-NHS-labeled catalytically-disabled lysozyme (i.e., Preparation #1 supra) and F-NHS-lysozyme and were prepared according to EXAMPLE 1 and comparisons were made of their effectiveness for detection of alkaline and/or protease killed and denatured bacteria and fungi by flow cytometry. Most pathogenic fungi contain chitin in their cell walls, septa and spores, both in hyphal and yeast forms. Chitin is a $\beta1\rightarrow4$ linked linear polymer of 2-deoxy-2-acetamidoglucose (N-acetyl glucosamine, GlcNAc.) Fungi do not contain bacterial murein proteoglycans and chitin is a poor substrate for lysozymes with hydrolysis of chitins proceeding at a much slower rate than mureins. Similarly, bacteria do not contain chitin and are not reactive with chitinase.

Surprisingly, using fluorescence microscopy and *Candida albicans* as a test fungi, F-NHS-labeled catalytically-disabled lysozyme and F-NHS-lysozyme both stained yeast cells, and much more brightly than the staining that could be achieved using a chitin-specific binding protein, i.e., chitin glycosyl hydrolase-F-NHS conjugate. Neither F-NHS-labeled conjugate stained mammalian or plant cells or their products. Also surprisingly, under the conditions of use, staining of bacteria in urine sediments was not as easily detectable as staining of fungi, i.e., because of their size. In other words, under the conditions of use in cytofluorimetric assays the method was able to selectively distinguish between the presence of bacteria and/or fungi in a test sample. Fluorescence labeling of Candida by both the F-NHS-catalytically disabled lysozyme and the F-NHS-lysozyme depended upon the preparative method (supra) used to prepare a biological sample for analysis. Fluorescence signal generation was markedly greater, i.e., as measured by fluorescence intensity in fluorescence cytometry, when a test Candida yeast in a urine sediment was subject to alkaline denaturation followed by N-acetylation, but not O-acetylation. While not wishing to be tied to any particular mechanism of action, but by way of possible explanation, lysozyme binding specificity for yeast cells may require the presence of murein-like compounds and lysozymes may not effectively bind chitosans in a fungal cell wall with sufficient affinity to generate a signal in the assay. Chitosan is present as a natural cell wall material in fungi, or as a possible result from deacetylation following alkaline treatment procedures (supra). Chitosan may be converted to murein-like compounds by N-acetylation (supra.) In different experiments, the conditions suitable for N-acetylation, without destroying the killed and denatured yeast particles in urine sediments, were found to be treatments at a final dilution of about 1/20–1/40 acetic anhydride (i.e., 5–10 μl for 200 μl to 300 μl total sample volume; about 1–10% acetic anhydride final concentration); using chemically pure acetic anhydride (e.g., distilled to remove acetic acid); and, in a saturated solution of $NaHCO_3$ at pH 8.0 for 15–30 minutes at room temperature. Using the combination of both alkaline hydrolysis and N-acetylation the killed and denatured yeast or bacterial particles in the treated urine sediment were fully reactive with the lysozyme F-NHS-conjugate (EXAMPLE 1, Preparation #1, supra). In the absence of an alkaline treatment the signal was dramatically reduced. Protease treatment did not increase the signal of a sample exposed to both treatments, but it did increase the signal of a sample with fungal aggregates and subject to only the alkaline treatment. However, periodate oxidation (i.e., increasing the number of free sugar residues available for acetylation) followed by acetylation did increase signal strength in certain samples.

In comparative studies, killed and denatured fungi in alkaline- and N-acetylation-treated urine samples were as reactive with F-NHS-lysozyme as with the catalytically disabled lysozyme conjugate (Preparation #1, EXAMPLE 1, above.). The mechanism responsible is at present unknown. The treatment method seems to produce killed and denatured fungal particles that contain substrates for catalytically active lysozyme conjugates, but, substrate turnover in the particles seems to be at a reduced rate, or turnover may not result in release of substantial free enzyme following the catalytic reaction.

Figure 2B:
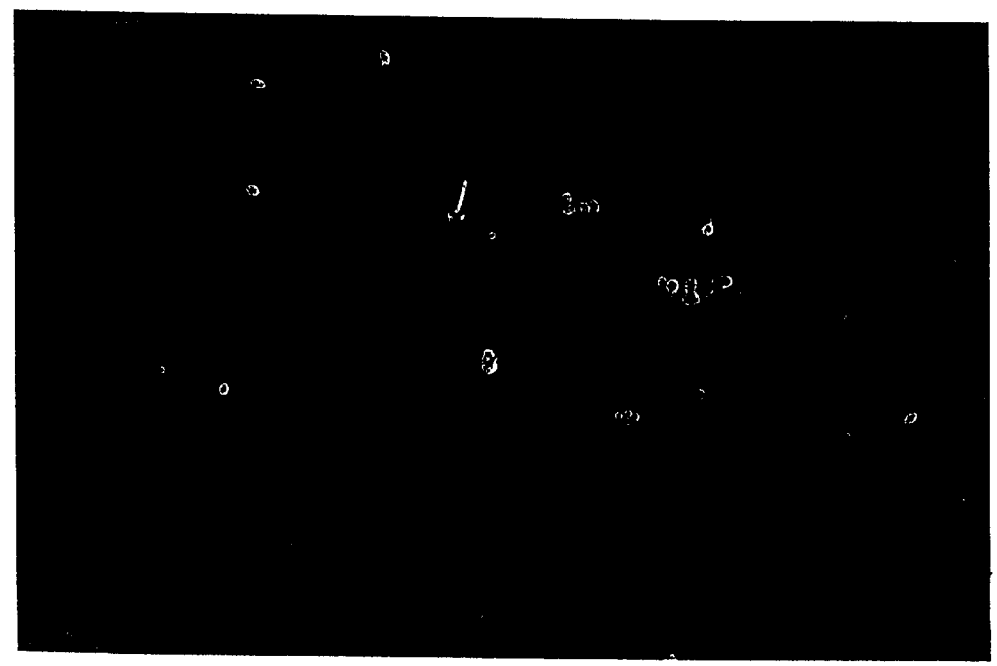
FIG. 2B shows a photomicrograph of fluorescence staining of killed and denatured fungal particles after treatments and staining according to the methods of the invention, as illustrated in EXAMPLE 8, below.

Illustrative Urine Sediment Sample Treatment Protocol:

One to ten milliliters of urine was centrifuged at 3000 rpm in a clinical centrifuge at room temperature (i.e., 22° C.) for 10 minutes. The urine sediment was resuspended in 100 $\mu$l 2N NaOH and subject to hydrolysis for about 15–30 minutes at 60° C. to kill bacteria and fungi; to hydrolyze and denature polypeptides and cell wall fragments; to expose murein- and murein-like-compounds in the particles; to alkylate cell surface charged residues involved in aggregation; and, to disaggregate bacterial or fungal rafts, aggregates and cell clumps without lysing cells. Following alkaline treatment, the killed and denatured particulate suspension was brought to neutrality by adding 30 $\mu$l of 6N HCl and setting it aside at room temperature for minutes. If aggregates, rafts or clumps of particles remained, the denatured cellular proteins in the particles were subject to an optional step of enzymatic hydrolysis, i.e., protease treatment with 0.25% trypsin for 30 minutes at 37° C. in a volume of about 100 $\mu$l PBS, pH 7.0. The chemical treatment alone was usually sufficient to hydrolyze bacterial and fungal intracellular adhesins; degrade potentially confusing polypeptides (e.g., endogenous chitinases, lysozymes and the like); degrade most potentially interfering substances (e.g., mammalian cells, bacterial cells, bacterial cell wall fragments, fungal cell wall fragments and the like); degrade fungal casts (e.g., releasing cells from hyphae); and release individual fungal cells from rafts, clumps, aggregates and the like. To increase the reactivity of murein- and murein-like compounds with MBP, i.e. lysozyme, the killed and denatured particles were subject to N-acetylation by adding 100 $\mu$l saturated NaHCO$_3$, pH 8, followed by 5–10 $\mu$l of pure (redistilled) acetic anhydride, i.e., final concentration in the assay of about 2–5% (v/v.) (N-acetylation was used to convert chitosan and other fungal compounds into more murein-like compounds reactive with MBP.) After 2–10 minutes at room temperature 100 $\mu$l of PBS, pH 7.0 was added, followed by 100 $\mu$l of PBS-5% BSA, pH 7.0, i.e., bringing the total volume to about 400–500 $\mu$l. The particles were detected by adding 30–40 $\mu$l of a solution of F-NHS-lysozyme (4–8 mg/ml), and by incubating for 15–30 minutes to effect binding of the MBP to the particles before microscopic examination in a fluorescence microscope or counting in a cytofluorimeter (i.e., FAXSCAN, Becton Dickinson Inc.) Cytofluorimetric counting was at a rate of about 5,000–9,000 killed and denatured particles per second and requiring about 2–30 seconds to count a total of 10,000–20,000 particles. The uniformity of the dispersed cells following this sample treatment protocol is illustrated in the fluorescence photomicrograph presented in FIG. 2B, which was prepared from a normal urine sediment sample to which a suspension of *Candida albicans* had been added. As illustrated in FIG. 2B, most yeast forms were present either in single or budding double cell forms, with only about one visible aggregate, clump or raft of cells per 10 visual fields.

FIG. 2B shows a photomicrograph of fluorescence staining of *Candida albicans* grown for 48 hrs./37° C. on Sabouraud dextrose agar and then added to normal urine sediment, treated with alkaline treatments (supra), stained with F-NHS-labeled catalytically-disabled lysozyme prepared according to EXAMPLE 1, above (i.e., Preparation #1), and examined as a wet mount using fluorescence microscopy. Most yeast forms stained were either single cell or budding double cell organisms with aggregates reduced to only one in every 10 microscopic visual fields.

For rapid cytometric analysis, this chemical sample pretreatment protocol was found to be crucial. In FIG. 2C, is shown a plot of fluorescence intensity (x axis; FSC-H/FSC-Height) against particle size (y axis; SSC-H/SSC-Height) for a urine sediment collected from a normal (healthy) subject, (i.e., without bacteria or yeast particles), and subject to the chemical treatment protocol disclosed above. The circle labeled "YG" in FIGS. 2C and 2F indicates the region where fluorescent yeast particles, if present, would appear, i.e., referred to herein as the "yeast gate". After cytometry counting, the data was subject to computerized selection and sorting process using *Candida albicans* as a positive control and normal human urine sediment particles as a negative control. The selection process involved sorting the data for those data points having a particle size and a fluorescence intensity that corresponded visually (i.e., by screen display) with the size and fluorescence intensity for the positive yeast particle control while excluding the majority of the negative control urine sediment particles. In FIG. 2D, is shown an aliquot of the same urine sediment without the chemical treatment, i.e., urine sediment particles populate the yeast gate, and if yeast were present in the latter situation, they would not be distinguishable from the urine residue particles based on size and fluorescence intensity, as shown from the data presented in FIG. 2E. In FIG. 2E, is shown another aliquot of the same urine sediment to which a suspension of *Candida albicans* was added. The sample was not subjected to chemical treatment and the added yeast and urine particles have similar size distribution and both populate the 'yeast gate'. In FIG. 2F, is shown an aliquot of the same urine sample, with *Candida albicans* added, and after the instant chemical treatment, i.e., yeast populate the 'yeast gate' and are separated from other urine sediment particles.

Figure 2G:
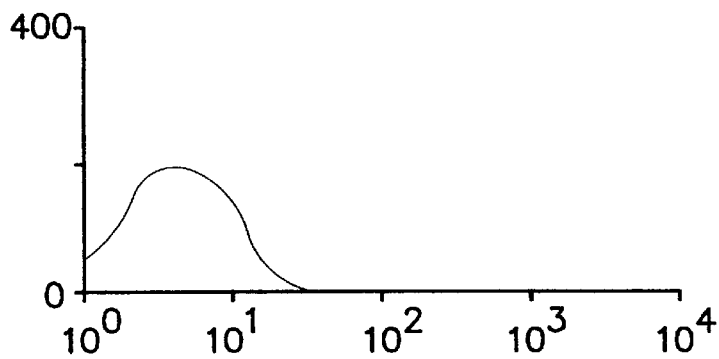
FIG. 2G shows a plot of the number of fungal particles (y axis) against fluorescence intensity (x axis) before chemically treating or staining a negative control biological sample, as disclosed further in EXAMPLE 8, below.
Figure 2H:
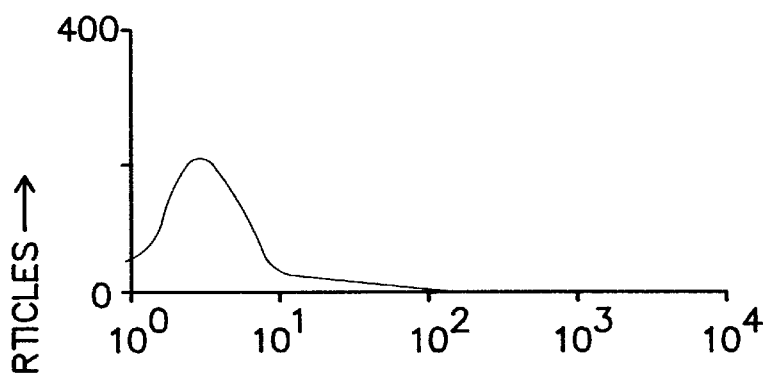
FIG. 2H shows a plot of the number of fungal particles (y axis) against fluorescence intensity (x axis) before chemical treatment or staining a negative control fungal sample in buffer; as disclosed further in EXAMPLE 8, below.
Figure 2I:
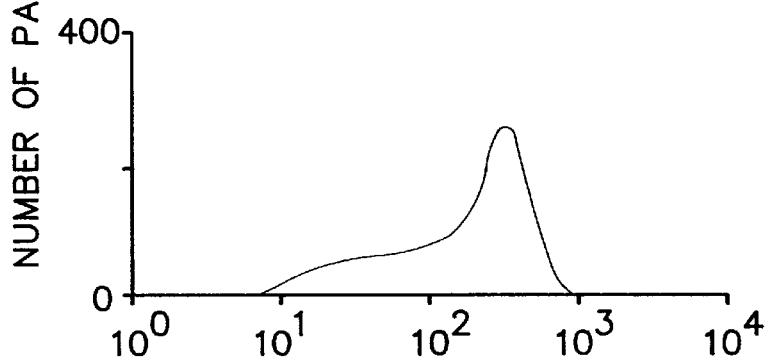
FIG. 2I shows a plot of the number of killed and denatured fungal particles (y axis) against fluorescence intensity (x axis) after alkaline treatment and then staining a biological sample with MBP-conjugate, as disclosed further in EXAMPLE 8, below.
Figure 2J:
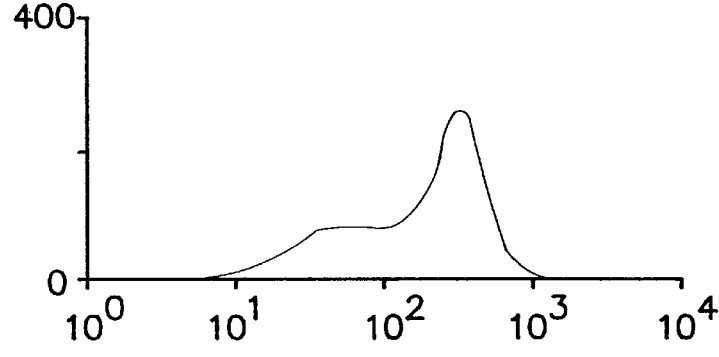
FIG. 2J shows a plot of the number of killed and denatured fungal particles (y axis) against fluorescence intensity (x axis) after alkaline treatment and then staining a positive control fungal sample in buffer with MBP-conjugate, as disclosed further in EXAMPLE 8, below.
Figure 2K:
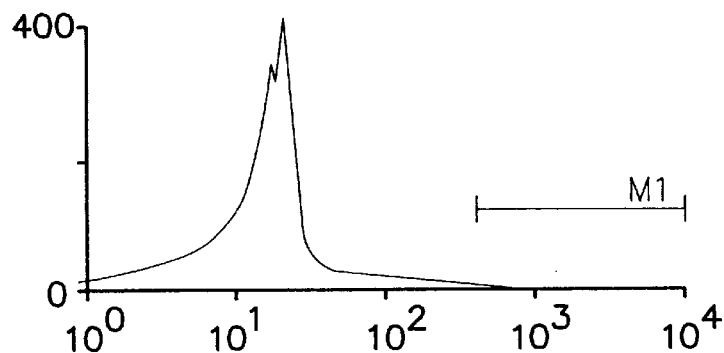
FIG. 2K shows a plot of the number of killed and denatured fungal particles (y axis) against fluorescence intensity (x axis) after alkaline- and acetylation-treatments, but before staining a first positive control fungal biological urine sample, as disclosed further in EXAMPLE 8, below.

In FIGS. 2G–J is presented a plot of the selected yeast gate-data (y axis; number of particles) for fluorescence intensity (x axis; FSC-H/FSC-Height) of killed and denatured *Candida albicans* particles. The experiment was designed to evaluate only the steps of alkaline treatment and F-NHS-lysozyme staining, i.e., without N-acetylation and/or protease treatments. FIG. 2G shows the background in a control sample from unstained and untreated yeast particles (i.e., the sample background without chemical treatment.) FIG. 2H depicts the control data collected with unstained untreated aggregated yeast particles in buffer, rather than with urine sediment (i.e., the yeast background). FIG. 2I depicts a plot of the fluorescence data obtained for an alkaline-treated yeast urine sediment sample stained with F-NHS-lysozyme. The F-NHS-lysozyme stained sample shows two relatively poorly resolved peaks of fluorescence staining, perhaps relating to the presence of doublet and singlet yeast forms in the sample. FIG. 2J depicts data obtained for an alkaline-treated yeast-buffer sample parallel to that of FIG. 2H, above, but stained with F-NHS-lysozyme. The two peaks of fluorescence coincide with those in FIG. 2I indicating that the observed properties are independent of any possible urine/urea effects on the killed and denatured yeast particles.

Figure 2L:
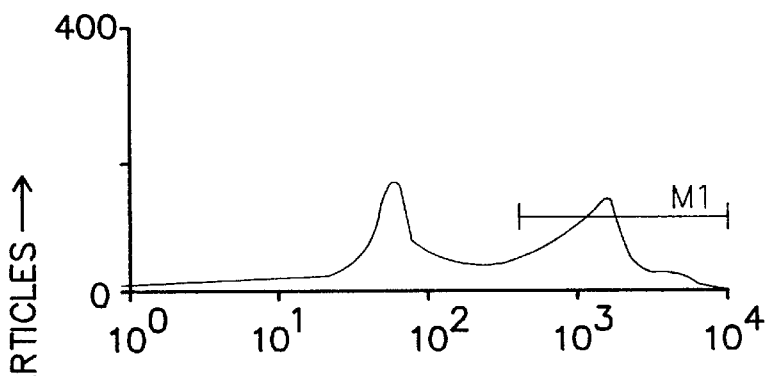
FIG. 2L shows a plot of the number of killed and denatured fungal particles (y axis) against fluorescence intensity (x axis) after alkaline- and acetylation-treatments and staining a first positive control fungal biological urine sample with MBP-conjugate, as disclosed further in EXAMPLE 8, below.
Figure 2M:
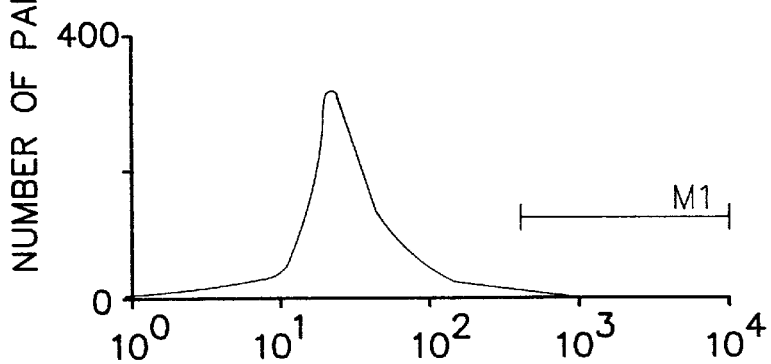
FIG. 2M shows a plot of the number of killed and denatured fungal particles (y axis) against fluorescence intensity (x axis) after alkaline- and acetylation-treatments, but before staining a second positive control fungal biological urine sample, as disclosed further in EXAMPLE 8, below.
Figure 2N:
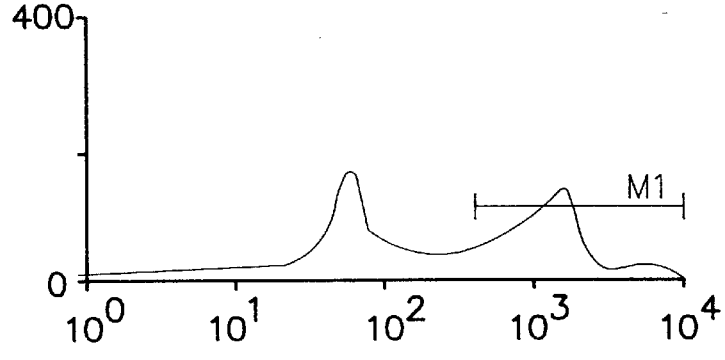
FIG. 2N shows a plot of the number of killed and denatured fungal particles (y axis) against fluorescence intensity (x axis) after alkaline- and acetylation-treatments and staining a second positive control fungal biological urine sample with MBP-conjugate, as disclosed further in EXAMPLE 8, below.

FIGS. 2K–2N present unsorted data showing the clear peak separation achieved between urine sediment particles and killed and denatured yeast particles when alkaline treatment was followed by a step of N-acetylation. In particular, data are shown from experiments in which suspensions of Candida albicans cells were added to 1 ml aliquots of normal urine. The aliquot samples were subjected to alkaline treatment (supra); followed by neutralization with 6 N HCl; and N-acetylation with 5 μl (FIG. 2L) or 10 μl (FIG. 2N) of acetic anhydride at pH 8.0 in 400 μl saturated bicarbonate buffer. The control results presented in FIG. 2J and FIG. 2L show the yeast negative control background (unstained, i.e., "sample background", supra.) In FIGS. 2L and 2N are shown peaks of yeast particles having fluorescence intensities, (i.e., "M1" channel peak at about 1200–3000 FSC-H in FIGS. 2K and 2M), that are well separated from stained residual particles in the urine sediment (i.e., at about 300–800 FSC-H.). The quantitative data collected in these experiments is summarized in TABLE 6.

TABLE 6

Cytofluorimetry Data: Quantitative Aspects of the Data Presented in FIGS. 2K–2N

| Figure | Channel | Window[a] L | Window[a] R | Particles Counted | % Total | Peak[b] Counted | Peak Channel 1 | Mean Intensity | Median Intensity |
|---|---|---|---|---|---|---|---|---|---|
| 2K | 0 | 1.00 | 9646 | 10,000 | 100 | 383 | 17 | 38 | 15 |
| 2L | M1 | 254 | 9646 | 135 | 1.4 | 8 | 2654 | 1368 | 505 |
| 2M | 0 | 1.00 | 9646 | 10,000 | 100 | 289 | 19 | 52 | 21 |
| 2N | M1 | 254 | 9646 | 245 | 2.5 | 18 | 274 | 958 | 392 |

[a]Window, fluorescence intensity settings for lower and upper limits;
[b]Peak Counted, number of particles counted at the peak of fluorescence intensity.

To evaluate the combined advantages of alkaline treatment, acetylation and sorting data for particles conforming with a 'yeast gate' (supra), Candida albicans was again used as a test fungi. Different numbers of yeast cells, in suspension, were added to aliquots samples of normal human urine, and the samples subject to sedimentation and alkaline and acetylation treatments (supra.) Urine samples were stained by reacting for 10, 15, 20 and minutes at 37° C. with 0.01–1 mg/ml of F-disabled lysozyme (Preparation #1, above) or of F-NHS-lysozyme (i.e., wild-type enzyme conjugate, supra) and then aliquots were subject to analysis by flow cytometric analysis in a fluorescence cytometer (Beckton Dickinson Model LSYS II) at a flow rate of 1.0 μl/second and sufficient particles were commonly present so that counting could be concluded in about 3–4 seconds. After counting, a software-controlled gate setting was applied to the data and used to visually select the 'yeast gate' from a plot of particle size (i.e., SSC) vs. fluorescence intensity. The resultant window excluded most of the fluorescence attributable to urine residue particles as bacteria. The results presented in TABLE 7, below, show the effects of the visual gate selection procedure on the particles counted and peak flourescence of control samples of urine spiked with Candida utilis (i.e., having small bacterial sized cells), Micrococcus lesodeikticus, and urine samples from three patient with UTI of unknown etiology and one with a bacterial UTI. All urine sediment samples were subjected to just alkaline treatment followed by N-acetylation (supra.)

TABLE 7

Effect of Size Gating on Counting of Low Signal Fluorescence Particles in Urine Sediment Samples

| Sample No. | Sample | Yeast Gated | Particles Counted | Peak Fluorescence |
|---|---|---|---|---|
| 1 | Urine sediment + C. utilis | NO YES | 10,000 83 | 300 3 |
| 2 | Urine sediment + M. lesodeikticus | NO YES | 10,000 19 | 379 2 |
| 3 | Patient A, UTI Bacterial | NO YES | 10,000 522 | 294 17 |
| 4 | Patient B, UTI Unknown | NO YES | 10,000 8,670 | 278 277 |

TABLE 7-continued

Effect of Size Gating on Counting of Low Signal Fluorescence Particles in Urine Sediment Samples

| Sample No. | Sample | Yeast Gated | Particles Counted | Peak Fluorescence |
|---|---|---|---|---|
| 5 | Patient C, UTI Unknown | NO YES | 10,000 1,614 | 200 47 |
| 6 | Patient D, UTI Unknown | NO YES | 10,000 5,185 | 223 221 |

The results show that 99% of all small bacteria-sized particles, i.e., C. utilis and M. lesodeikticus, are removed from counting by the comparative method of visually selecting a 'yeast gate' with F-NHS-lysozyme stained Candida albicans positive control sample. The results also seem to confirm the known bacterial UTI infection in Patient #A, i.e., all of the particles counted fall outside of the range appropriate for yeast particles; and, in favor yeast infections in patients #B and #C, since 87% and 52%, respectively, of the particles counted fell within the range appropriate for yeast particles. Patient #C, may represent primarily a bacterial infection and/or a yeast secondary infection since 16% particles counted fall within the region selected for yeast.

Figure 3A:
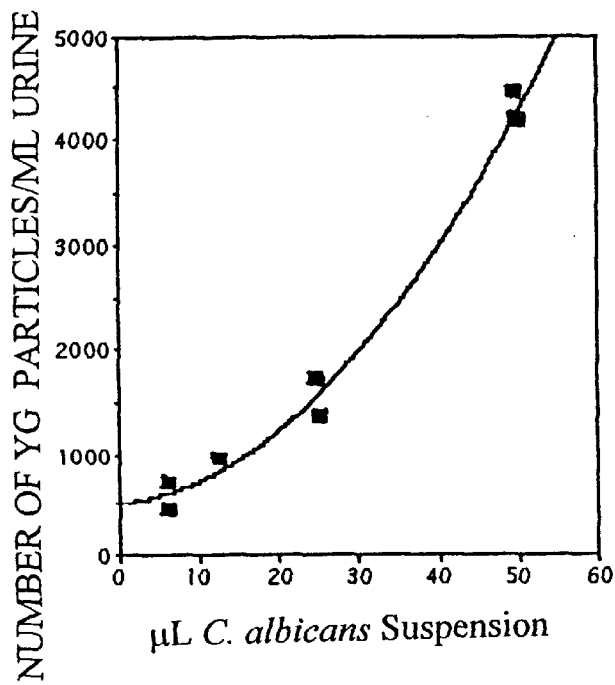
FIG. 3A depicts graphically the results of an experiment in which differing volumes ($\mu$l) of a fungal cell suspension were added to aliquots of a normal human urine sediment sample to achieve cell concentrations in the range of about 1,000–5,000 cells/ml urine. The individual aliquot samples were then prepared according to the alkaline- and protease-treatments and stained with MBP-conjugate according to the methods of the invention, as disclosed further below and illustrated in EXAMPLE 8.
Figure 3B:
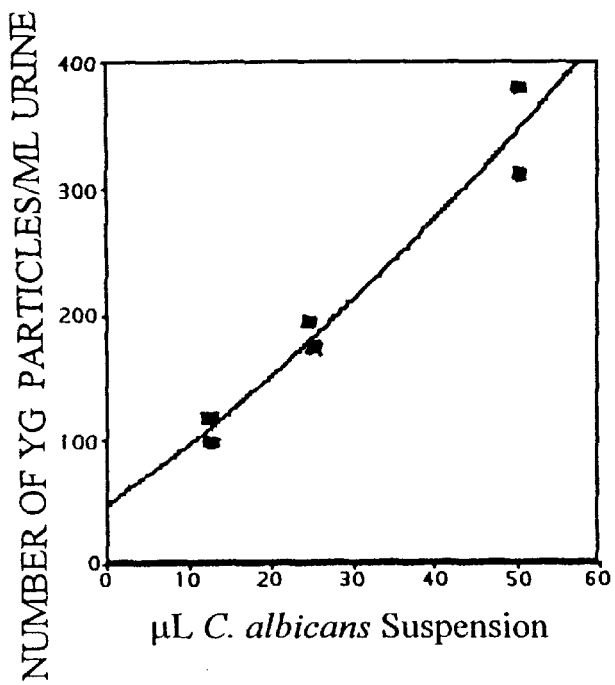
FIG. 3B depicts graphically the results of an experiment in which differing volumes ($\mu$l) of a fungal cell suspension were added to aliquots of a normal human urine sediment sample to achieve cell concentrations in the range of about 5,000–20,000 cells/ml urine. The individual aliquot samples were then prepared according to the alkaline- and protease-treatments and stained with MBP-conjugate according to the methods of the invention, as disclosed further below and illustrated in EXAMPLE 8.

In control experiments designed to investigate the sensitivity of the assay, known numbers of Candida albicans cells were added to normal urine sediment samples and the results were calculated and expressed graphically as either the total number of YG particles counted per milliliter of urine (FIG. 3A), or the number of YG particles counted per second (FIG. 3B.) The results presented in FIG. 3A show low-end sensitivity of the assay while those presented in FIG. 3B show high-end linearity for signal production.

FIG. 3A depicts graphically the results of an experiment in which differing volumes of a Candida albicans suspension (cells/ml) were added to a normal human urine sediment, (i.e., 10 ml normal urine centrifuged, treated under just alkaline conditions and with protease treatment (supra.) The urine sediment was resuspended in 500 µl=20-fold concentrated sample, and yeast cells were added to achieve yeast concentrations in the range of about 1000–5000 cells/ml of urine. Fungi in the sample were stained by incubating for 30 minutes with F-NHS-lysozyme at a final concentration of 80 µg/ml. The number of YG particles was quantified by cytofluorimetry using forward light scatter and flow cytometric counting. The x-axis expresses the microliters (µl) of yeast suspension added to the urine sediment and the y-axis the number of fluorescent stained YG particles detected per milliliter of the urine sedimented. (Curve fitting algorithm agreement, R2, was 0.994.)

A scatter plot representing the size of particles (y axis; SSC-H counted at each fluorescence intensity (x-axis; FFC-H) in FIG. 3A showed that the majority of the particles counted in the treated and F-NHS-MBP stained urine sediment sample (according to the methods described in regard to FIG. 3A, supra) were either single cell or double-cell yeast particles. However, the data also showed that a few aggregates still existed in alkaline and protease treated samples, accounting for a few particle counts lying outside the main YG fluorescence cluster.

FIG. 3B depicts graphically the results of an experiment in which differing volumes of *Candida albicans* suspension (cells/ml) were added to 10 ml of normal human urine. Following centrifugation the urine was resuspended in 500 µl (urine sediment sample), and subject to preparative treatments, staining and cytofluorimetric analysis as described in regards to FIG. 3A, above. The yeast were added to the whole urine to achieve yeast concentrations in the range of about 5,000–20,000 cells/ml urine, in this case, corresponding to 100–400 cells/second in the urine sediment sample at a cytometer flow rate of 1.0 µl/second.

The results presented in FIG. 3B show a linear second order polynomial relationship between the number of particles counted per second and the number of microliters of yeast input (cells/ml) into the assay over the range of about 1,000 to 5,000 cells/ml urine; and, without evidence that the assay was compromised in any way at the higher yeast inputs. The results presented in FIG. 3A show low-end assay sensitivity in the range of about 100 YG particles per milliliter of a urine sample, i.e., 1000 particles total in a 10 ml urine sample. Additional experiments were conducted in an attempt to determine the high-end limits of the assay (FIGS. 4 and 5), and to confirm linearity of signal generation at lower input analyte concentrations (FIG. 5) and in these experiments data are expressed as YG particles counted per second at a cytometer flow rate of 1 µl/sec. unless otherwise indicated.

Figure 4:
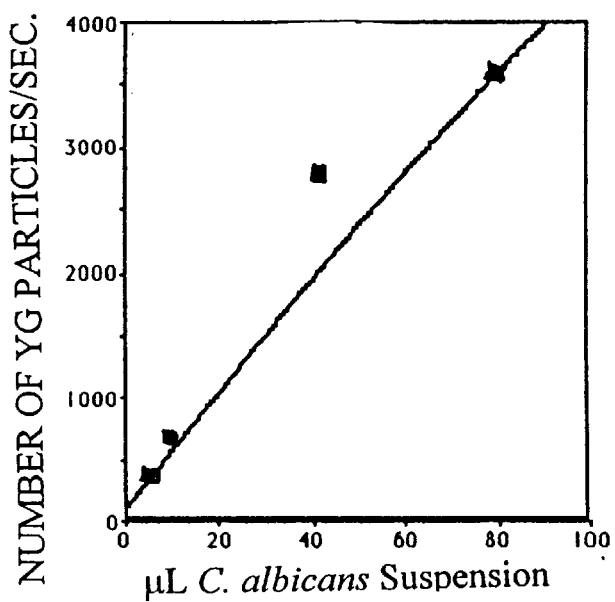
FIG. 4 depicts graphically the results of an experiment in which differing volumes ($\mu$l) of a fungal cell suspension were added to aliquots of a normal human urine sediment sample to achieve cell concentrations in the range of about 5,000–200,000 cells/ml urine. The individual aliquot samples were then prepared according to the alkaline- and protease-treatments and stained with MBP-conjugate according to the methods of the invention, as disclosed further below and illustrated in EXAMPLE 8.

FIG. 4 depicts graphically the results of an experiment in which differing volumes of *Candida albicans* suspension (cells/ml) were added to 10 ml of normal urine. Following centrifugation the urine was resuspended in 500 µl (urine sediment sample), and subjected to preparative treatments, staining and cytofluorimetric analysis as described above in regard to FIG. 3A. The yeast were added to the whole urine to achieve yeast concentrations in the range of about 50,000–200,000 cells/ml urine, i.e., 1,000–4,000 cells/second in the urine sediment sample at a cytometer flow rate of 1.0 µl/second. (Curve fitting algorithm agreement, R2, was 0.999.)

Figure 5:
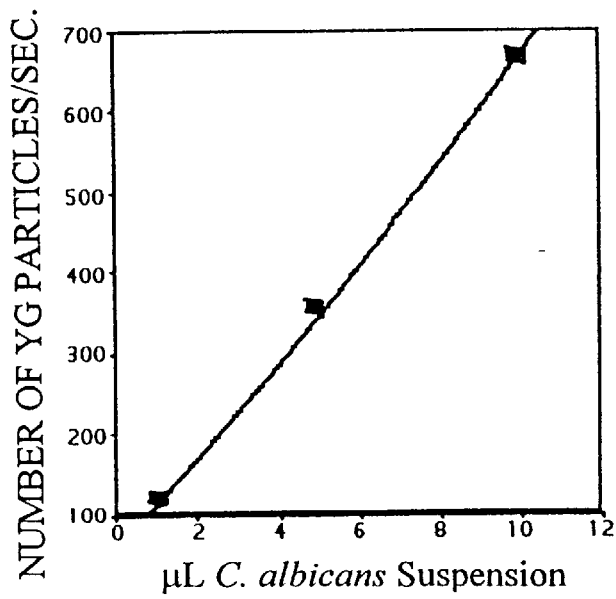
FIG. 5 depicts graphically the results of an experiment in which differing volumes ($\mu$L) of a suspension of fungal cells were added to urine to achieve cell concentrations in the range of about 5,000–35,000 cells/ml urine; treated with alkaline and protease treatments as in FIG. 3A, above; and then fungi in the sample were detected by staining with an MBP-conjugate as disclosed in EXAMPLE 8, below.

FIG. 5 depicts graphically the results of an experiment in which differing volumes of *Candida albicans* suspension (cells/ml) were added to 10 ml of normal urine. Following centrifugation the urine was resuspended in 500 µl (urine sediment sample), and subject to preparative treatments, staining and cytofluorimetric analysis as in described in regards to FIG. 3A, above. The yeast were added to the whole urine to achieve yeast concentrations in the range of about 5,000–35,000 cells/ml urine, i.e., 100–700 cells/second in the urine sediment at a flow rate of 1.0 µl/second. (Curve fitting algorithm agreement, R2, was 1.0.)

Figure 6:
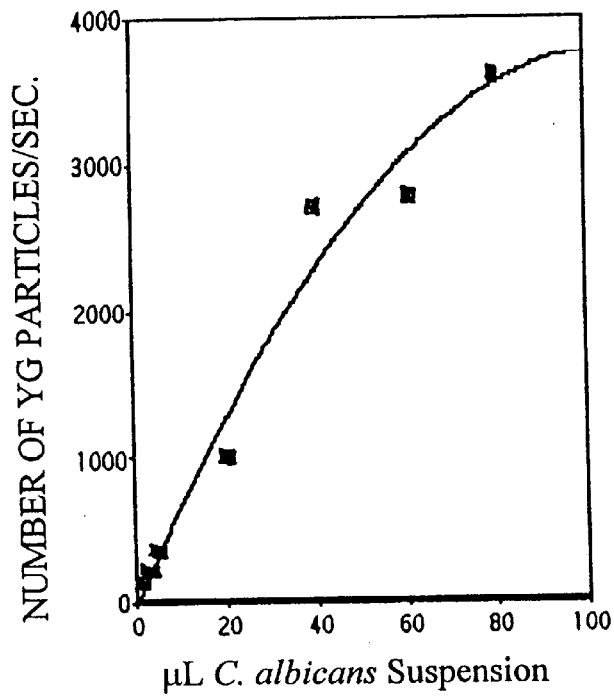
FIG. 6 depicts graphically the results of an experiment in which differing volumes of a fungal cell suspension were added to 10 ml of normal urine to achieve cell concentrations in the range of about 50,000–200,000 cells/ml urine; treated with alkaline and protease treatments as in FIG. 3A, above; and then fungi in the sample were detected by staining with an MBP-conjugate as disclosed in EXAMPLE 8, below.

FIG. 6 depicts graphically the results of an experiment in which differing volumes of *Candida albicans* suspension (cells/ml) were added to 10 ml of normal urine. Following centrifugation the urine was resuspended in 500 µl (urine sediment sample), and subject to preparative treatments, staining and cytofluorimetric analysis as described in regards to FIG. 3A, above. The yeast were added to the whole urine to achieve yeast concentrations in the range of about 50,000–200,000 cells/ml urine, i.e., 1,000–4,000 cells/second in the urine sediment at a flow rate of 1.0 µl/second. (Curve fitting algorithm agreement, R2, was 0.977.)

The combined results presented in FIGS. 3A, 3B, 4, 5 and 6 indicate a near linear relationship between signal generated and amount of analyte input (i.e., yeast cells) into the assay with a dynamic range for the assay over about 2.3-logs of analyte concentration (i.e., 500–150,000 cell/ml in urine), but with some fall-off in performance at 200,000 cells/ml. The results show a low-end sensitivity of about 50–100 cells/ml in urine (i.e., 5000 cells in a 10 ml urine sample, concentrated to 500 µl in a urine sediment, giving about 10 particles/µl/second through the cytometry detector.) The lower limit for linearity of detection, quantification, in this particular assay was in the range of about 1,500 to about 3,000 cells/ml of a urine sample: a number that may correspond to about 500–1000 cells. An acceptable signal-noise ratio was achieved through the alkaline and N-acetylation sample treatments, and use of an F-NHS-MBP yeast positive control to select a yeast gate setting for sorting and accepting data points.

To test stability of the killed and denatured disaggregated and stained particles (i.e., just alkaline and/or protease treated and stained) prepared and F-NHS-MBP stained urine sediment sample, samples stained with F-NHS-lysozyme according to FIGS. 2 and 3A, supra, were stored at 4° C. for 3 days and then assayed by flow cytometry. The results presented in FIG. 7 show that the signal generation by the sample was stable to storage at 4° C.

Figure 7:
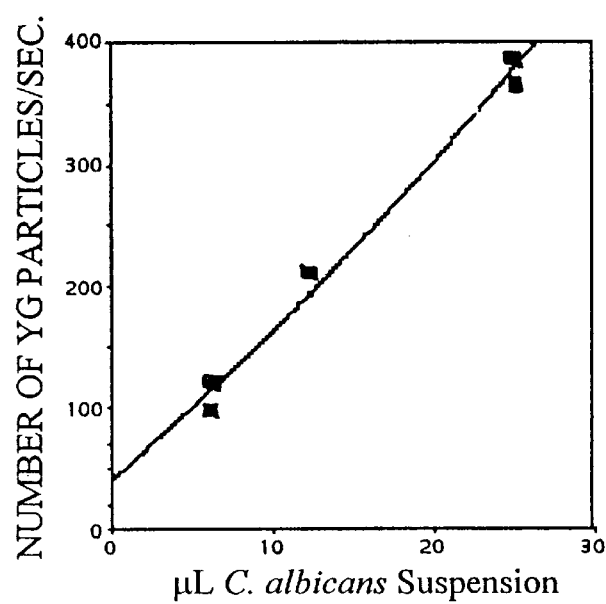
FIG. 7 depicts graphically the results of an experiment in which differing volumes of a fungal cell suspension were added to a normal urine sediment to achieve cell concentrations in the range of about 2,500–20,000 cells/ml of urine; treated with alkaline and protease treatments as in FIG. 3A, above; fungi were stained with an MBP-conjugate, and then stored at 4° C. for 3 days prior to analysis. The number of killed and denatured fungal particles was quantified as disclosed in EXAMPLE 8, below.

FIG. 7 depicts graphically the results of an experiment in which differing volumes of a *Candida albicans* suspension (cells/ml) were added to a normal urine sediment, (i.e., 10 ml normal urine centrifuged, treated under alkaline conditions and with protease-supra, and then resuspended in 500 µl=20-fold concentrated sample), to achieve yeast concentrations in the range of about 2,500–20,000 cells/ml of urine. Yeast were stained with F-NHS-labeled MBP, as described in FIG. 3A, and then stored at 4° C. for 3 days prior to analysis. The number of fungal particles was quantified by cytofluorimetry using forward light scatter and flow cytometric counting. The x-axis expresses the microliters of yeast suspension added to the urine sediment and the y-axis the number of fluorescent stained particles detected per milliliter of the urine sediment. (Curve fitting algorithm, R2, was 0.994.)

Figure 8:
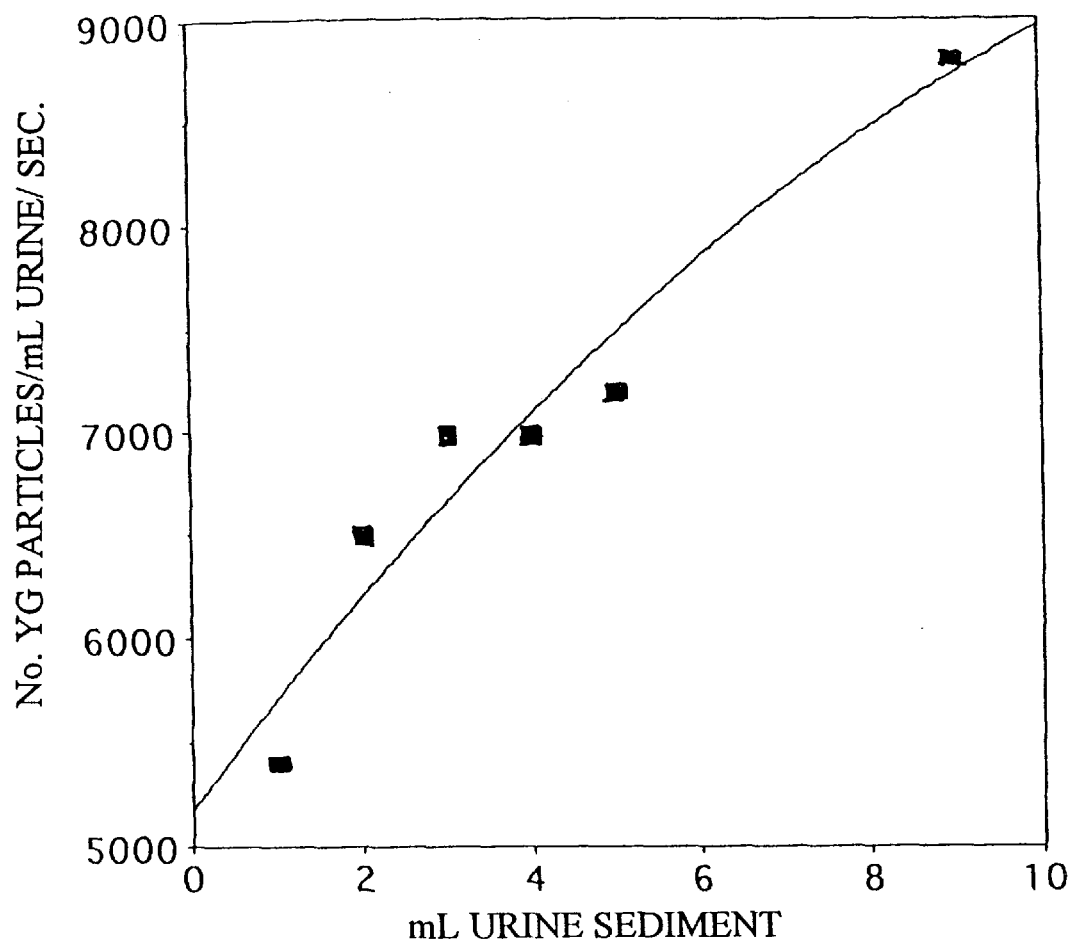
FIG. 8 depicts graphically the results recorded in chemically treating, MBP-staining and cytofluorimetrically assaying aliquots of a urine sample from a patient with a urinary tract infection. The data are plotted as the number of killed and denatured fluorescent fungal particles ("YG") counted per milliliter (mL) of urine per second against the different volumes of urine (mL) that were sedimented to obtain each of the different respective samples, as disclosed further in EXAMPLE 8, below.

Additional experiments were conducted to verify that the alkaline treatment conditions were effective for treatment of clinical samples containing differing numbers of cells; that the assay was functional within the range of analyte (yeast cells/ml) concentrations encountered in clinical practice;

and that linearity was preserved when using clinical samples. For these experiments a urine sample was collected from patient #1201 with UTI confirmed by culture. The biological sample was subject to treatment as follows: namely, 1, 2, 3, 4, 5, or 9 ml of urine were centrifuged in a clinical centrifuge (3000 rpm/10 minutes at 4° C.) to prepare a urine sediment. Each respective urine sediment was then treated under alkaline conditions only, i.e., 500 $\mu$l/1 N NaOH, and, since some visual aggregates still remained the sample was next treated with 0.25% trypsin for 30 minutes (supra) to disaggregate remaining urine sediment particles. The respective killed and denatured urine residue sediments were resuspended in 500 $\mu$l of PBS and then stained with F-NHS-labeled catalytically disabled-lysozyme (Preparation #1, Method 1.) The respective sediments were washed with PBS and resuspending in 500 $\mu$l PBS for flow fluorimetry, and stained for 30 minutes at 37° C. with 80 $\mu$g/ml of the catalytically inactive F-NHS-lysozyme. Cytometric methods were as described in regard to FIG. 3A, above, with sampling was at 60 $\mu$l/minute using the undiluted treated 500 $\mu$l urine sediment sample (supra.) Sample counting was complete (i.e., 97–99% confidence interval) at 4 seconds for the 1 ml urine sample (i.e., 5,400 fungal cells/sec.) and at 3 seconds for the 2–9 ml urine samples (i.e., 6,500 cells/sec.–8,800 cells/sec.) The results presented in FIG. 8 show that patient #1201 had about 5,400–8,800 cells/$\mu$l/second in the respective different urine sediments (corresponding to 54,000–2,700,000 yeast/ml in urine), i.e., at the high operating range of the assay. The slope of the curve in FIG. 8, as well as, the y-intercept value, each defining a parameter for the severity of the UTI infection in patient #1201. The results presented in FIG. 8 show that sufficient particles are present in certain clinical samples to allow for collection of only small urine volumes and/or dilution of urine sediment samples prior to analysis. Thus, titration curves may be constructed using differing amounts of urine samples (e.g., as in FIG. 7), or alternatively, by preparing a dilution series from a freshly prepared and stained (or 4° C. stored) urine sediment. The dilution series can be constructed to bring the number of particles counted/$\mu$l of urine sediment sample/second within the range of about 1500–3000. The data collected in the assay may be plotted as cell counts per microliter urine sediment per second versus the dilution of urine sediment input to the assay, (i.e., as in FIG. 8), and the plotted data defines a slope of a curve with a y-intercept. Both the value for thee for the slope and for the y-intercept relate to the severity of an infection in the patient from which the urine sample was obtained. Quantitative aspects of the data obtained in this experiment are summarized in TABLE 8 below.

TABLE 8

| Sample Volume (ml) | MBP-conjugate* | Particles Counted | Mean Fluorescence Intensity | YG Particles/sec. |
|---|---|---|---|---|
| 1 | + | 20,000 | 515 | 5,400 |
| 2 | + | 20,000 | 828 | 6,500 |
| 3 | + | 20,000 | 813 | 7,000 |
| 4 | + | 20,000 | 1199 | 7,000 |
| 5 | + | 20,000 | 1586 | 7,200 |
| 9 | + | 20,000 | 1854 | 8,800 |
| Negative Control | – | 20,000 | 6 | — |

*MBP-conjugate, murein binding polypeptide-conjugate, i.e., catalytically inactive F-NHS-lysozyme; 500 $\mu$l total final volume; window setting for fluorescence intensity L, 1.00 and R 9646.

The results show that the assay and alkaline treatment method, are capable of quantifying fungal particles in a killed and denatured urine sediment residue in the absence of a step of N-acetylation. N-acetylation, however, is effect to increase the signal strength in the assay, improve low end sensitivity and reproducibility.

The results presented in FIGS. 9A, 9B, 10A, 10B and 11A–D show performance of the assay with clinical urine samples collected from patients with urinary tract infections. All samples were subject to sedimentation (3000 rpm in a clinical centrifuge, supra); alkaline-(2N NaOH/30 minutes/60° C., supra) followed by neutralization-(6N HCl, supra), and acetylation-(10 $\mu$l acetic anhydride, pH 8 bicarbonate buffer, supra) treatments; staining with F-NHS-lysozyme (80 $\mu$g/ml, supra); and, fluorocytometric particle counting (1 $\mu$l/sec.) as described in regard to FIG. 3A, above (i.e., without protease treatment). Fluorescence data points in FIGS. 9A, 10A, 11A and 11C were ungated while those presented in FIGS. 9B, 10B, 11B and 11D were sorted and selected for YG particles falling with a 'yeast gate' (supra.) (The number of YG particles counted during sample analysis in regards to FIGS. 11C and 11D, i.e., 1800 YG particles/sec., allowed shorter counting times.)

Figure 9A:
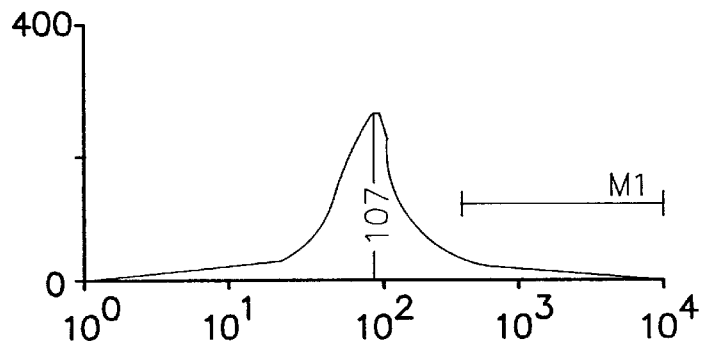
FIGS. 9A and 9B depicts graphically the results recorded in chemically treating, MBP-staining and cytofluorimetrically assaying a 1 mL aliquot of a urine sample from a patient with a bacterial urinary tract infection. The data are plotted as the number of killed and denatured fluorescent fungal particles against the fluorescence intensity (FSC-H/FSC-Height) of each particle.
Figure 9B:
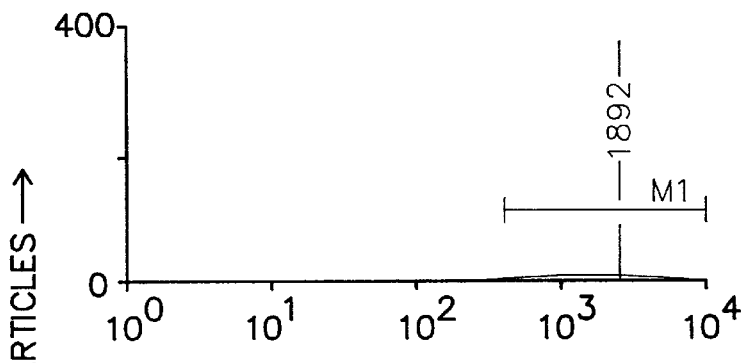

The data presented in FIGS. 9A and 9B was recorded after analysis of a urine sample from a patient having a confirmed (by culture) bacterial UTI and most killed and denatured particles were clustered into a single peak having a fluorescence intensity of about 107 (i.e., FSC-H.) Analysis of the data collected in the instant assay supports diagnosis of a bacterial urinary tract infection. Interestingly, after sorting the data to remove most urinary sediment particles and bacterial particles (i.e., the peak in FIG. 9A), a small residual broad peak of YG particles was observed with a mean fluorescence intensity at about 1892 FSC-H. It is theoretically possible that this patient had developed a low-level secondary yeast infection.

Figure 10A:
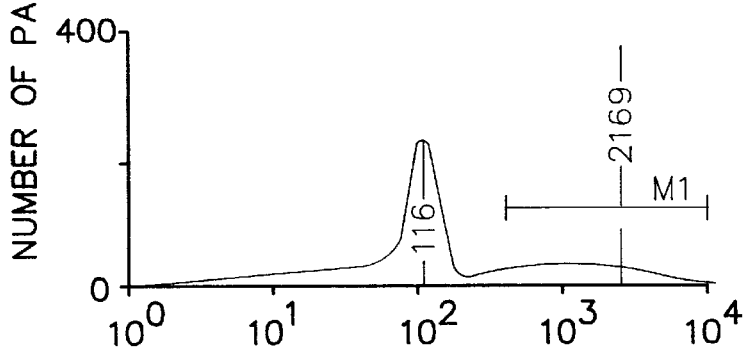
FIGS. 10A and 10B depicts graphically the results recorded in chemically treating, MBP-staining and cytofluorimetrically assaying a 1 mL aliquot of a urine sample from a patient with a yeast urinary tract infection. The data are plotted as the number of killed and denatured fluorescent fungal particles against the fluorescence intensity (FSC-H/FSC-Height) of each particle.
Figure 10B:
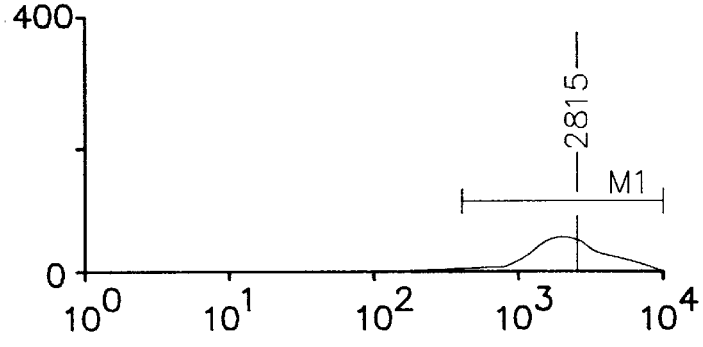
Figure 11A:
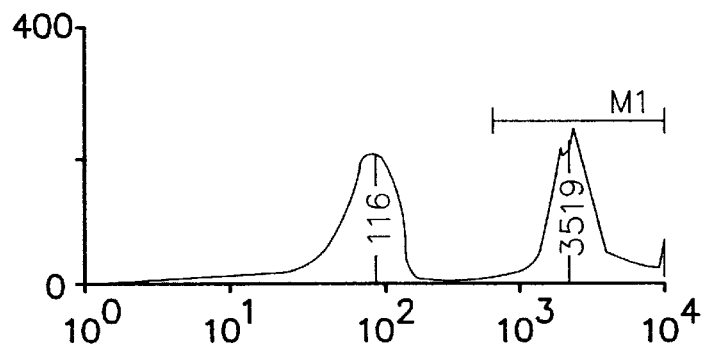
FIGS. 11A–D depicts graphically the results recorded in chemically treating, MBP-staining and cytofluorimetrically assaying a 1 mL aliquot of a urine sample from a patient with an unknown urinary tract infection. The samples assayed in FIGS. 11A and 11B were collected from the patient one day prior to those assayed in FIGS. 11C and 11D (i.e., day 1 and day 2). The data are plotted as the number of killed and denatured fluorescent fungal particles against the fluorescence intensity (FSC-H/FSC-Height) of each particle.
Figure 11B:
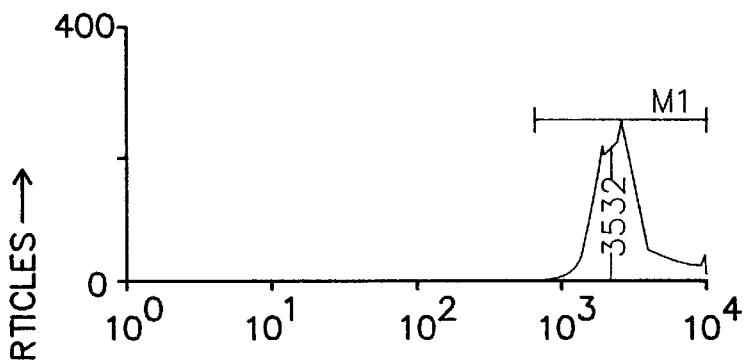
Figure 11C:
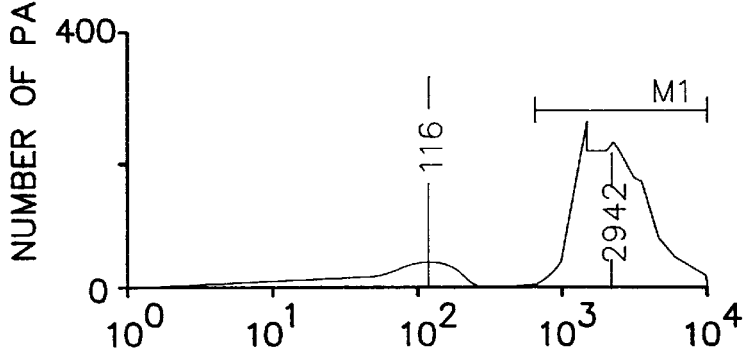
Figure 11D:
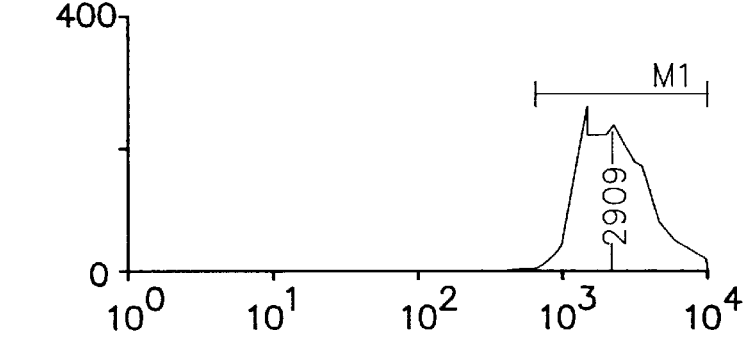

The data presented in FIGS. 10A, 10B, was recorded after analysis of a urine sample from a patient with a confirmed yeast UTI, and similarly, and data presented in FIGS. 11A, 11B, 11C and 11D was recorded after analysis of urine sediment samples collected one day apart (i.e., FIGS. 11A–B, day 1; FIG. 11C–D, day 2) from a patient with a UTI of unknown etiology. The results presented in FIGS. 10A[\N]B and 11A–D show YG particles in the samples, and support a diagnosis of a yeast UTI. Importantly, the fluorescence intensity data presented in FIGS. 11C–D was recorded over a much shorter sampling time (i.e., at a counting rate of 1800 cells/second) than that recorded in FIGS. 11A–B and the total YG particles counted in FIGS. 11C–D were nearly three times greater than those recorded in FIGS. 11A–B. The results presented in FIGS. 11A–D would suggest that if anti-bacterial therapy was administered to this particular patient, it was not effective in eliminating the yeast infection.

MATERIALS

Protein assay reagents, ion exchange resins (e.g., BioRex-70), and gel filtration resins were from Bio-Rad Laboratories (Richmond, Calif.). Chitin, chitosan, buffer salts, and electrophoresis standards were from Sigma Chemical Co. (St. Louis, Mo.). Acrylamide: bisacrylamide solution (37.5:1) was from Amresco (Solon, ohio.). Sepharose 4B and Sephadex 4B, 6B and Sephadex G75 were from Pharmacia Fine Chemicals (Uppsala, Sweden.) Calibration beads having a diameter of 0.5$\mu$ were from Becton-Dickinson.

CITATIONS

1. Garrner, D. L. et al. 1995. *Biol. of Reprod.* 53: 276–284.

2. Dijkstra, B. W.; Thunnissen, A. M. 1994. *Curr. Opin. Struct. Biol.* 4(6): 810–3.
3. Chipman, D. M., Grisaro, V. and Sharon, N. 1967. *J. Biol. Chemistry* 242: 4388–4394. Chipman, D. M. and Sharon, N. 1969. *Science* 165: 454–465.
4. Kuroki, R., Yamada, H., Moriyama, T., and Imoto, T. 1986. Chemical mutations of the catalytic groups in lysozyme to the corresponding amides. *J. Biol. Chem.* 261: 13571–74.
5. Eschdat, Y., Dunn, A. and Sharon, N. 1974. Chemical conversion of Aspartic acid 52, a catalytic residue in hen egg-white lysozyme, to homoserine. *Proc. Natl. Acad. Sci. (USA)* 71: 1658–1662.
6. Macossay, J. 1994. Neolectin-like protein with aggultinating activity of wheat germ agglutinin. *Biochmica et Biophysica Acta* 1200: 331–333.
7. Escott, G. M. and Adams, D. J. 1995. Chitinase activity in human serum and leukocytes. *Inf. Imm.* 63: 4770–4773.
8. Chamberland et al. Chitinase-gold complex used to localize chitin ultrastructurally in tomato root cells. *Histochem. J.* 17: 313–321.
9. Benjaminson, M. A. 1969. Conjugates of chitinase with fluorescein isothiocyanate or lissamine rhodamine as specific stains for chitin in situ. *Stain Technology* 44: 27–31.
11. Ohno, N. and Morrison, D. C. 1989. Lipopolysaccharide interation with lysozyme. *J. Biol. Chemistry* 264: 4434–44.
12. Chou and Fasman. 1978. *Adv. Enzymol.* 47: 45–148.
13. O'Neil and DeGrado. *Science* 250: 646–51.
14. Kadurugamuwa, J. L. and Beveridge, T. J. 1996. Bacteriolytic effect of membrane vesicles from Pseudomonas aeruginosa on other bacteria including pathogens: conceptually new antibiotics. *J. Bacteriol.* 178 (10): 2767–74.
15. Pares, S., Mouz, N., Petillot, Y., Hakenbeck, R., Dideberg, O. 1996. X-ray structure of Streptococcus pneumoniae PBP2x, a primary penicillin target enzyme. *Nat. Struct. Biol.* 3(3): 284–9.
16. Park, J. T. 1995. Why does Eschericia coli recycle its cell wall products? *Mol. Microbiol.* 17(3): 421–426.
17. Lu, M. J., Henning, U. 1992. Lysis protein T of bacteriophage T4. *Mol. Gen. Genet.* 235(2–3): 253–8.
18. Ehlert, K., Holtje, J. V., Templin, M. F. 1995. Cloning and expression of a murein hydrolase lipoprotein from *Eschericia coli*. *Mol. Microbiol.* 16(4): 761–8.
19. Dijkstra, B. W., Thunnissen, A. M. 1994. 'Holy' proteins.II: The soluble lytic transglycosylase. *Curr. Opin. Struct. Biol.* 4(6): 810–3.
20. Villanueva, M. S., Fischer, P., Feen, K., Pamer, E. G. 1994. Efficiency of MHC class I antigen processing: a quantitative analysis. *Immunity* 1(6): 479–89.
21. Romeis T., Holtje, J. V. 1994. Penicillin-binding protein 7/8 of *Eschericia coli* is a DD-endopeptidase. *Eur. J Biochem.* 224 (2): 597–604.
22. Ursinus, A., Holtje, J. V. 1994. Purification and properties of a membrane-bound lytic transglycosylase from *Eschericia coli*. *J. Bacteriol.* 176(2): 338–43.
23. Gan, K., Gupta, S. D., Sankaran, K., Schmid, M. B., Wu, H. C. 1993. Isolation and characterization of a temperature-sensitive mutant of Salmonella typhimurium defective in prolipoprotein modification. *J. Biol. Chem.* 268 (22): 16544–50.
24. Lu, M. J., Henning, U. 1992. Lysis protein T of bacteriophage T4. *Mol. Gen. Genet.* 235 (2–3): 253–8.
25. Templin, M. F., Edwards, D. H., Holtje, J. V. 1992. A murein hydrolase is the specific target of bulgecini in *Eschericia coli*. *J. Biol. Chem.* 267 (28): 20039–43.
26. Bishop, R. E., Weiner, J. H. 1992. Coordinate regulation of murein peptidase activity in AmpC beta-lactamase synthesis in *Eschericia coli*. *FEBS Lett.* 304 (2–3): 103–8.
27. Ursinus, A., Steinhaus, H., Holtje, J. V. 1992. Purification of a nocardicin A-sensitive LD-carboxypeptidase from *Eschericia coli* by affinity chromatography. *J. Bacteriol.* 174 (2): 20 441–6.
28. Engel, H., Kazemier, B., Keck, W. 1991. Murein-metabolizing enzymes from *Eschericia coli*: sequence analysis and controlled overexpression of the slt gene, which encodes the soluble lytic transglycosylase. *J. Bacteriol.* 173 (21): 6773–82.
29. Mottl, H., Terpstra, P., Keck, W. 1991. Penicillin-binding protein 4 of *Eschericia coli* shows a novel type of primary structure among penicillin-interacting proteins. *FEMS Microbiol. Lett.* 62 (2–3): 213–20.
30. Keck, W., van Leeuwen, A. M., Huber, M., Goodell, E. W. 1990. Cloning and characterization of mepA, the structural gene of the penicillin-insensitive murein endopeptidase from *Eschericia coli*. *Mol. Microbiol.* 4(2): 209–219.
31. Romero, A., Lopez, R., Garcia, P. 1990. Characterization of the pneumococcal bacteriophage HB-3 amidase: cloning and expression in *Eschericia coli*. *J. Virol.* 64 (1): 137–42.
32. Garcia, P., Garcia, E., Ronda, C., Lopez, R. 1985. [Phenotypical curing of Streptococcus pneumoniae treated with amidase produced by the Dp-1 bacteriophage] *Microbiologia* (Spain) 1 (1–2): 35–41.
33. Brito, N., Falcon, M. A., Carnicero, A., Gutierrex-Navarro, A. M., Mansito, T.B. Purification and peptidase activity of a bacteriolytic extracellular enzyme from Pseudomonas aeruginosa. *Res. Microbiol.* 140 (2): 125–37.
34. Hayashi, S., Hara, H., Hirota, Y. 1988. Lipid modification of *Eschericia coli* penicillin-binding protein 3. *J. Bacteriol.* 170 (11): 5392–5.
35. Vanderwinkel, E., de Vlieghere, M., Charles, P., Baptist, V. 1987. Nature of the interactions involved in the lipid-protein complexes of the *Eschericia coli* N-acetylmuramoyl-L-alanine amidase. *Biochim. Biophys. Acta* 913 (2): 238–44.
36. Kuroki, R., Weaver, L. H., Matthews, B. W. 1995. Structure-based design of a lysozyme with altered catalytic activity. *Nat. Struct. Biol.* 2 (11): 1007–11.
37. Pjura, P., Matthews, B. W. 1993. Structure of randomly generated mutants of T4 lysozyme show that protein stability can be enhanced by relaxation of strain and improved hydrogen bonding via bound solvent. *Protein Sci.* 2 (12): 2226–32.
38. Kuroki, R., Weaver, L. H., Matthews, B. W. 1993. A covalent enzyme-substrate intermediate with saccharide distortion in a mutant T4 lysozyme. *Science* 262 (5142): 2030–3.
39. Kam-Morgan, L. N., Smith-Gill, S. J., Taylor, M. G., Zhang, L, Wilson, A. C., Kirsch, J. F. 1993. High resolution mapping of the HyHEL-10 epitope of chicken lysozyme by site directed mutagenesis. *Proc. Natl. Acad. Sci. USA* 90 (9): 3958–62.
40. Inoue, M., Yamada, H., Yasukochi, T., Miki, T., Horiuchi, T., Imoto, T. 1992. Left-sided substrate binding of lysozyme: evidence for the involvement of asparagine-46 in the initial binding of substrate to chicken lysozyme. *Biochemistry* 31 (42): 10322–30.
41. Kamagai, I., Sundada, F., Takeda, S., Miura, K. 1992. Redesign of the substrate-binding site of hen egg white lysozyme based on the molecular evolution of C-type lysozymes. *J. Biol. Chem.* 267 (7): 4608–12.
42. Lumb, K. J., Aplin, R. T., Radford, S. E., Archer, D. B., Jeenes, D. J., Lambert, N., MacKenzie, D. A., Dobson, C.

M., Lowe, G. 1992. A study of D52S hen lysozyme-GlcNac oligosaccharide complexes by NMR spectroscopy and electospray mass spectrometry. *FEBS Lett.* 296 (2): 153–7.
43. Poteete, A. R., Sun, D. P., Nicholson, H., Matthews, B. W. Second-site revertants of an inactive T4 lysozyme mutant restore activity by restructing the active site cleft. *Biochemistry* (5): 1425–32.
44. Faber, H. R., Matthews, B. W. 1990. A mutant T4 lysozyme displays five different crystal conformations. *Nature* 348 (6298): 198–9.
45. Malcolm, B. A., Rosenberg, S., Corey, M. J., Allen, J. S., de Baetselier, A., Kirsch, J. F. 1989. Site directed mutagenesis of the catalytic residues Asp-52 and Glu-35 of chicken egg white lysozyme. *Proc. Natl. Acad. Sci. USA* 86 (1): 133–7.
46. Heinz DW; Matthews B W. 1994. Rapid crystalization of T4 lysozyme by intermolecular disulfide cross-linking. *Protein Eng.* 7(3): 301–7.
47. Parsons, S. M. and M. A. Raftery. 1969. Methylation of Asp 52 destroys catalytic activity of chicken egg white lysozyme. *Biochemistry* 8: 4199–4205.
48. Hase, S., Ikenaka, T. and Mastushima, Y. 19789. *Biochem. Biophys. Res. Comm.* 85: 257–263.

While the preferred embodiment of the invention has been illustrated and described, it will be appreciated that various changes can be made therein without departing from the spirit and scope of the invention.

We claim:

1. A method for first detecting the presence or amount of a eubacteria or a fungus in a biological sample and for then determining the antibiotic sensitivity or antibiotic resistance of said eubacteria or a fungus comprising the steps of:
collecting the biological sample;
incubating a first aliquot of the cultured biological sample with a murein binding polypeptide under conditions suitable for binding of the murein binding polypeptide to the eubacteria or fungus;
detecting the bound murein binding polypeptide thereby detecting the presence or amount of the eubacteria or fungus in the biological sample;
then if said eubacteria or said fungus are detected, determining said antibiotic sensitivity by the steps of:
culturing a second and a third aliquot of the biological sample for a period of time and under conditions suitable for growth of the eubacteria or the fungus, wherein said second aliquot is cultured in the presence of said antibiotic and said third aliquot is cultured in the absence of said antibiotic; and,
incubating a portion of the second and the third aliquots with a murein binding polypeptide under conditions suitable for binding of the murein binding polypeptide to the eubacteria or fungus;
detecting the bound murein binding polypeptide thereby detecting the amount of the eubacteria or fungus in the biological sample;
determining the eubacteria or the fungus to be antibiotic sensitive if the amount of eubacteria or fungus in the third aliquot is greater than in the second;
wherein said murein binding polypeptide comprises a catalytically inactive enzyme capable of binding but not cleaving a peptidoglycan comprising NAc-muramic acid in said eubacteria or fungus.

2. The method of claim 1, wherein said murein binding polypeptide is conjugated to a signal generating compound.

3. The method of claim 2, wherein said catalytically inactive enzyme polypeptide has a binding site capable of binding to said peptidoglycan with a binding affinity of about $5 \times 10^{-7}$ L/mol to about $5 \times 10^{-9}$ L/mol and wherein said conjugate is effective when bound to said eubacteria to produce a detectable signal in a diagnostic assay format.

4. The method of claim 2, wherein said signal generating compound is selected from the group consisting of an enzyme, a fluorophore, a phycobilin, a biotin, an avidin, a streptavidin, a bioluminescent compound, a chemiluminescent compound, a hitochemical dye and a radiolabeled compound.

5. The method of claim 4, wherein said signal generating enzyme is selected from among a horse radish peroxidase, an alkaline phosphatase, a glucose oxidase, a catalase, a glucuronidase and a urease.

6. The method of claim 1 wherein said murein binding polypeptide further comprises a signal generating compound selected from the group consisting of an enzyme, a fluorophore, a phycobilin, a biotin, an avidin, a streptavidin, a bioluminescent compound, a chemiluminescent compound, a hitochemical dye, a magnetic particle and a radioactive compound.

7. The method of claim 6, wherein said signal generating enzyme is selected from the group consisting of a horse radish peroxidase, an alkaline phosphatase, a glucose oxidase, a catalase, a glucuronidase and a urease.

8. The method of claim 6, wherein said fluorophore is selected from the group consisting of a succinyl fluorescein, a fluorescein isothiocyanate, a rhodamine and a lissamine.

9. The method of claim 1, wherein said incubating step suitable conditions comprise the addition of an additive selected from the group consisting of a stabilizer, a buffer, an emulsifier, an agent inactivating a catalytically active enzyme to produce said catalytically inactive enzyme and an agent for promoting interactions between said murein binding polypeptide and said murein.

10. The method of claim 9, wherein said catalytically inactive enzyme is selected from the group consisting of a mutant enzyme, a recombinant enzyme and a chemically inactivated enzyme.

11. The method of claim 1, further comprising a chemical alkaline hydrolysis of the collected biological sample effective to hydrolyze a peptide bond in said eubacterial peptidoglycan before the incubation of the collected biological sample with the murein binding protein.

12. The method of claim 11, wherein said conditions suitable for binding of the murein binding polypeptide to the eubacteria comprise a fluid phase.

13. The method of claim 12, wherein said fluid phase comprises a cytometric fluid and said method for detecting comprises a cytometric method.

14. The method of claim 11, wherein said chemical alkaline hydrolysis comprises incubating the biological sample in a chemical base at a pH of greater than about 8, at a temperature of about 22° C. to about 70° C. for about 10 minutes to about 30 minutes.

15. The method of claim 14, wherein said chemical base is selected from the group consisting of sodium hydroxide, potassium hydroxide, ammonium hydroxide, barium hydroxide, calcium hydroxide, potassium carbonate, sodium carbonate, potassium acetate and sodium barbital.

16. The method of claim 11, wherein said collected biological sample is brought to about chemical neutrality after said chemical alkaline hydrolysis step and before said incubating step.

17. The method of claim 15, further comprising a chemical acetylation step after said neutralization step and before said incubation step, wherein said chemical acetylation step is effective to N-acetylate a eubacterial sugar residue in a eubacterial cell wall.

18. The method of claim 17, further wherein said chemical acetylation step comprises adding an acetylation reagent and incubating said chemically hydrolyzed and neutralized collected biological sample for about 2 minutes to about minutes at about 22° C.

19. The method of claim 18, wherein said acetylation reagent comprises acetic anhydride or acetic chloride.

20. The method of claim 1, wherein said catalytically inactive enzyme is selected from the group consisting of an acetyl-muramoyl-D,L- alanyl amidase, a bacterial cell wall enzyme binding penicillin, an alanyl D,D- or D,L-endopeptidase, a D,D- or D,L-carboxypeptidase, a transglycosyl transferase, a peptidyl transferase, a muramoyl isomerase, a muramoyl transglycosylase, a murein autolysin, a murein hydrolase and a lysozyme.

21. The method of claim 1, wherein said conditions suitable for binding of the murein binding polypeptide to the eubacteria or the fungus comprise both a fluid phase and a solid phase capture surface.

22. The method of claim 21, wherein said solid phase capture surface is selected from the group consisting of a 96-well microtiter plate, a polymeric plastic bead, a glass bead, a dipstick and a latex bead.

23. The method of claim 1, wherein said biological sample is selected from the group consisting of a sample collected from a human from a domestic animal and from food.

24. The method of claim 1, wherein said time for culturing said eubacteria comprises about 2 to about 6 hours.

25. The method of claim 24, wherein said time further comprises about 2 to about 4 hours.

26. The method of claim 25, wherein said time further comprises about 2 hours.

27. The method of claim 1, wherein said time for culturing said fungus comprises about 2 hours to about 20 hours.

28. The method of claim 27, wherein said time comprises about 2 hours to about 8 hours.

29. The method of claim 27, wherein said time comprises about 3 hours to about 6 hours.

30. The method of claim 1, wherein said eubacteria is selected from among a chlamydia, a toxoplasma, a staphylococci, a streptococci, a gonococci, a pneumococci, a mycobacteria and a bacillus.

31. The metod of claim 1, wherein said eubacteria is selected from among a Legionella, an Eschericia, a Clostridium, a Staphylococcus, a Streptococcus, a Pneumococcus.

32. The method of claim 1, wherein said fungus is selected from among an Aspergillus, a Candida, a Cryptococcus, a Histoplasma, a Coccidiomycosis, a Sacchromyces, a Blastomyces and an Actinomycetes.

33. The method of claim 1, wherein said antibiotic is selected from among a penicillin, an ampicillin, an amoxycillin, a vancomycin, a streptomycin, an erythromycin, a bacitracin, a tetracycline, a polymyxin, a novobiocin, a colistin, a kanamycin, a neomycin, a ristocetin, a gramicidin, a spiramycin, a cephalosporin, a capreomycin, a rifamycin and a gentamycin.

34. A method for determining the antibiotic sensitivity or antibiotic resistance of a eubacteria or a fungus in a biological sample comprising the steps of:

collecting the biological sample;

culturing a first and a second aliquot of the biological sample for a period of time and under conditions suitable for growth of the eubacteria or the fungus, wherein said first aliquot is cultured in the presence of said antibiotic and said second aliquot is cultured in the absence of said antibiotic;

separately incubating a portion of both the first and the second aliquot with a murein binding polypeptide under conditions suitable for binding of the murein binding polypeptide to the eubacteria or the fungus;

detecting the bound murein binding polypeptide thereby detecting the amount of the eubacteria or fungus in the first and the second aliquot;

determining that the eubacteria or the fungus is antibiotic sensitive if the amount of eubacteria or fungus in the second aliquot is greater than in the first; and, determining that the eubacteria or the fungus is antibiotic resistant if the amount of eubacteria or fungus in the first and the second aliquot are about the same, wherein said murein binding polypeptide comprises a catalytically inactive enzyme capable of binding but not cleaving a peptidoglycan comprising NAc-muramic acid in said eubacteria or fungus.

* * * * *